US010828354B2

(12) United States Patent
Braun et al.

(10) Patent No.: US 10,828,354 B2
(45) Date of Patent: Nov. 10, 2020

(54) LASER-ASSISTED INTRADERMAL ADMINISTRATION OF ACTIVE SUBSTANCES

(71) Applicant: PANTEC BIOSOLUTIONS AG, Ruggell (LI)

(72) Inventors: Reinhard Braun, Lustenau (AT); Dorothea Terhorst, Marseilles (FR); Sandrine Henri, Marseilles (FR); Bernard Malissen, Marseilles (FR); Yoan J. Machado, Salzburg (AT); Mellissa Mayr, Salzburg (AT); Theresa Thalhamer, Salzburg (AT); Veronika Höpflinger, Salzburg (AT); Josef Thalhamer, Salzburg (AT); Richard Weiss, Salzburg (AT)

(73) Assignee: PANTEC BIOSOLUTIONS AG, Ruggell (LI)

( * ) Notice: Subject to any disclaimer, the term of this patent is extended or adjusted under 35 U.S.C. 154(b) by 0 days.

(21) Appl. No.: 15/568,124

(22) PCT Filed: Apr. 20, 2016

(86) PCT No.: PCT/EP2016/058733
§ 371 (c)(1),
(2) Date: Oct. 20, 2017

(87) PCT Pub. No.: WO2016/169971
PCT Pub. Date: Oct. 27, 2016

(65) Prior Publication Data
US 2018/0140690 A1   May 24, 2018

(30) Foreign Application Priority Data

Apr. 20, 2015   (EP) .................................. 15164306
May 11, 2015   (EP) .................................. 15167225

(51) Int. Cl.
| *A61K 39/00* | (2006.01) |
| *A61K 39/38* | (2006.01) |
| *A61K 39/385* | (2006.01) |
| *C07K 14/77* | (2006.01) |
| *C07K 14/52* | (2006.01) |
| *A61P 37/02* | (2006.01) |
| *A61P 31/00* | (2006.01) |
| *A61P 37/08* | (2006.01) |
| *A61P 35/00* | (2006.01) |
| *A61B 18/20* | (2006.01) |
| *A61K 45/06* | (2006.01) |
| *C07K 16/28* | (2006.01) |
| *A61B 18/00* | (2006.01) |

(52) U.S. Cl.
CPC ........ *A61K 39/0011* (2013.01); *A61B 18/203* (2013.01); *A61K 45/06* (2013.01); *A61P 31/00* (2018.01); *A61P 35/00* (2018.01); *A61P 37/02* (2018.01); *A61P 37/08* (2018.01); *C07K 14/521* (2013.01); *C07K 14/77* (2013.01); *C07K 16/2866* (2013.01); *A61B 2018/00577* (2013.01); *A61K 2039/54* (2013.01); *A61K 2039/6056* (2013.01); *C07K 2319/00* (2013.01); *C07K 2319/33* (2013.01)

(58) Field of Classification Search
CPC ................ A61K 38/00; A61K 39/0011; A61K 2039/6037
See application file for complete search history.

(56) References Cited

U.S. PATENT DOCUMENTS

| 6,148,232 A | 11/2000 | Avrahami | |
| 2003/0170236 A1* | 9/2003 | Matzinger | .......... C07K 16/2812 424/144.1 |

FOREIGN PATENT DOCUMENTS

| WO | 2004/076489 A1 | 9/2004 |
| WO | 2009/044272 A2 | 4/2009 |
| WO | 2013/033496 A2 | 3/2013 |
| WO | 2014/151403 A1 | 9/2014 |

OTHER PUBLICATIONS

Chen et al., PLoS One, 2010; 5(10): 1-11 (Year: 2010).*
Terhorst et al., The Journal of Immunology, Apr. 15, 2015; 194: 5895-5902 (Year: 2015).*
Weiss et al., J Control Release, 2012; 162: 391-399 (Year: 2012).*
Preissig et al., Semin Plast. Surg., 2012; 26: 109-116 (Year: 2012).*
International Preliminary Report on Patentability and the Written Opinion of the International Searching Authority dated Oct. 24, 2017, in connection with corresponding International Application No. PCT/EP2016/058733 (7 pgs.).
International Search Report dated Jun. 23, 2016, in connection with corresponding International Application No. PCT/EP2016/058733 (4 pgs.).
William W. Agace, "Tissue-tropic effector T cells: generation and targeting opportunities", in Nature Reviews Immunology, vol. 6, Sep. 2006, pp. 682-692 (12 pgs.).
Susan Ahrens, et al., "F-Actin is an Evolutionarily Conserved Damage-Associated Molecular Pattern Recognized by DNGR-1, a Receptor for Dead Cells", in Immunity, vol. 36, Apr. 20, 2012, pp. 635-645 (11 pgs.).

(Continued)

*Primary Examiner* — Gary B Nickol
*Assistant Examiner* — Lakia J Jackson-Tongue
(74) *Attorney, Agent, or Firm* — Maier & Maier, PLLC

(57) ABSTRACT

A vaccine preparation comprising an antigen for use in the prophylactic or therapeutic treatment of a subject by intradermal administration through laser-generated micropores, wherein the antigen is linked to a binder of a dermal migratory antigen-presenting cell (APC); and a pharmaceutical preparation comprising an active substance for use in the prophylactic or therapeutic treatment of a subject by intradermal administration through laser-generated micropores, for regional delivery to a target location. The invention further relates to the laser-assisted intradermal administration of antigens accompanied by repeated chemotherapy.

13 Claims, 18 Drawing Sheets

(56) References Cited

OTHER PUBLICATIONS

Figure 1:
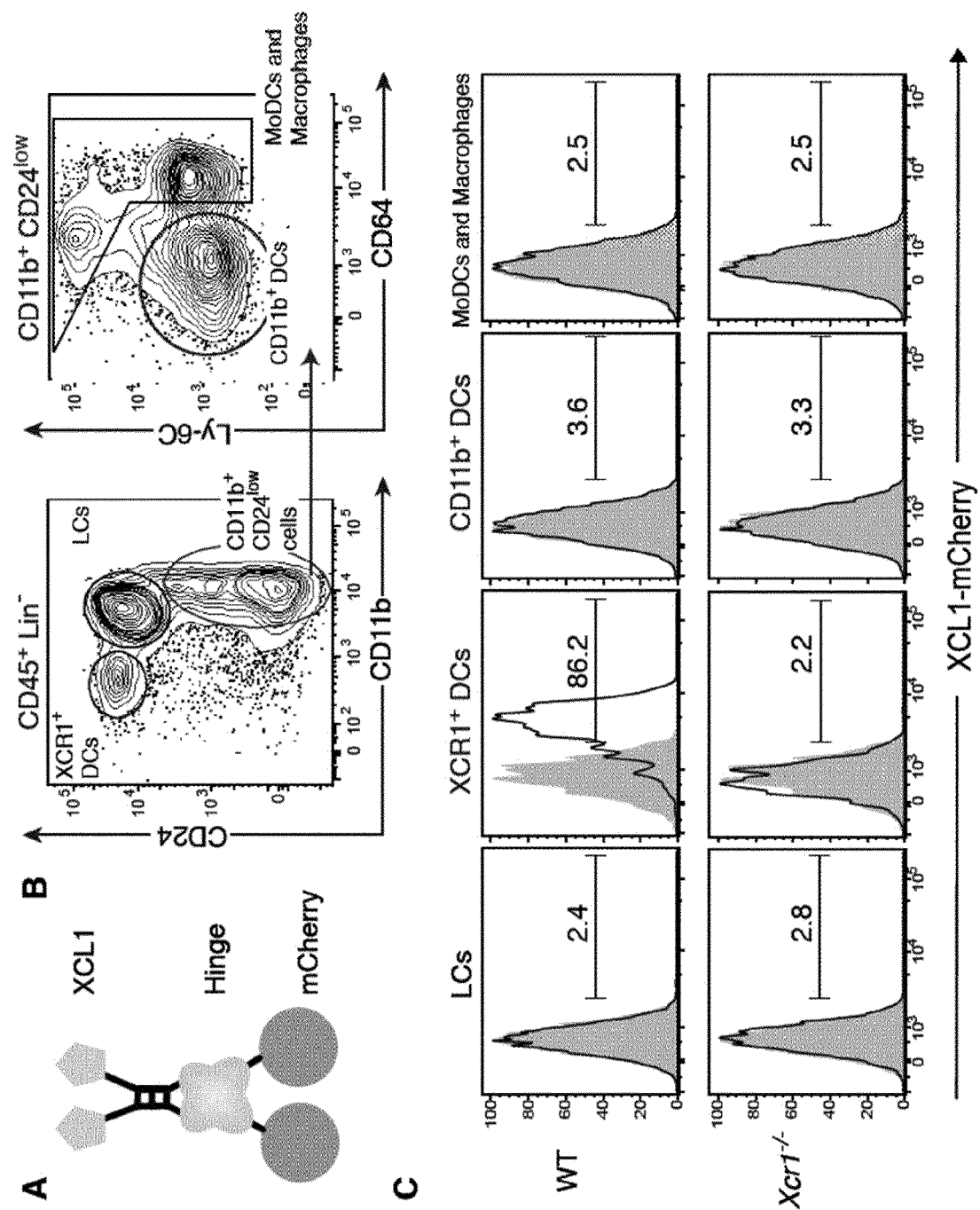

D. Bach, et al., "Transcutaneous immunotherapy via laser-generated micropores efficiently alleviates allergic asthmas in Phl p 5-sensitized mice", in Allergy, vol. 67, 2012, pp. 1365-1374 (10 pgs.).
Annabell Bachem, et al., "Superior antigen cross-presentation and XCR1 expression define human CD11c+CD141+ cells as homologues of mouse CD8+ dendritic cells", in the Journal of Experimental Medicine, vol. 207, No. 6, 2010, pp. 1273-1281 (9 pgs.).
Annabell Bachem, et al., "Expressoin of XCR1 characterizes the Batf3-dependent lineage of dendritic cells capable of antigen cross-presentation", in Frontier in Immunology, vol. 3, Jul. 2012, pp. 1-12 (12 pgs.).
Martin F. Bachmann, et al., "Vaccine delivery: a matter of size, geometry, kinetics and molecular patterns", in Nature Reviews Immunology, vol. 10, Nov. 2010, pp. 787-796 (10 pgs.).
Veronique Bachy, et al., "Langerin negative dendritic cells promote potent CD8+ T-cell priming by skin delivery of live adenovirus vaccine microneedle arrays", in Proc Natl Acad Sci (PNAS), Feb. 19, 2013, vol. 110, No. 8, pp. 3041-3046 (6 pgs.).
Megan J. Bamden, et al., "Defective TCR expression in transgenic mice constructed using cDNA-based α- and β-chain genes under the control of heterologous regulatory elements", in Immunology and Cell Biology, vol. 76, 1998, pp. 34-40 (7 pgs.).
Sammy Bedoui, et al., "Cross-presentation of viral and self antigens by skin-derived CD103+ dendritic cells", in Nature Immunology, vol. 10, No. 5, May 2009, pp. 488-495 (8 pgs.).
D. M. Brown, et al., "Tumours can act as adjuvants for humoral immunity", in Immunology, vol. 102, 2001, pp. 486-497 (12 pgs.).
Miranda Broz, et al., "Dissecting the Tumor Myeloid Compartment Reveals Rare Activating Antigen Presenting Cells, Critical for T cell Immunity", in Cancer Cell (NIH Public Access—Author Manuscript), vol. 26, No. 5, Nov. 10, 2014, pp. 638-652 (28 pgs.).
Irina Caminschi, et al., "The dendritic cell subtype-restricted C-type lectin Clec9A is a target for vaccine enhancement", in Blood, vol. 112, No. 8, Oct. 2008, pp. 3264-3273 (11 pgs.).
Xinyuan Chen, et al., "An update on the use of laser technology in skin vaccination", in Expert Rev Vaccines (HHS Public Access—Author manuscript), vol. 12, No. 11, Nov. 2013, pp. 1-20 (20 pgs.).
Xinyuan Chen, et al., "Improved efficacy of dendritic cell-based immunotherapy by cutaneous laser illumination", in Clin Cancer Res. (NIH Public Access—Author Manuscript), vol. 18, No. 8, Apr. 15, 2012, pp. 1-18 (18 pgs.).
Xinyuan Chen, et al., "A Novel Laser Vaccine Adjuvant Increases the Motility of Antigen Presenting Cells", in PLOS One, vol. 5, Issue 10, Oct. 2010, 11 pgs.
Karine Crozat, et al., "The XC chemokine receptor 1 is a conserved selective marker of mammalian cells homologous to mouse CD8α+ dendritic cells", J. Exp. Med., vol. 207, No. 6, 2010, pp. 1283-1292 (10 pgs.).
Karine Crozat, et al, "Cutting Edge: Expression of XCR1 Defines Mouse Lymphoid-Tissue Resident and Migratory Dendritic Cells of the CD860 + Type", in the Journal of Immunology, vol. 187, 2011, pp. 4411-4415 (6 pgs.).
Marc Dalod, et al., "Dendritic cell maturation: functional specialization through signaling specificity and transcriptional programming", in the EMBO Journal, vol. 33, No. 10, 2014, pp. 1104-1116 (13 pgs.).
Liufu Deng, et al., "STING-dependent Cytosolic DNA Sensing Promotes Radiation-inducted Type I interferon-dependent Antitumor Immunity in Immunogenic Tumors", in Immunity (HHS Public Access—Author manuscript), vol. 41, No. 5, Nov. 20, 2014, pp. 1-22 (22 pgs.).
Madhav V. Dhodapkar, et al., "Induction of Antigen-Specific Immunity with a Vaccine Targeting NY-ESO-1- to the Dendritic Cell Receptor DEC-205", in Science Translational Medicine, vol. 6, Issue 232 232ra51, Apr. 16, 2014, 15 pgs.

Brigitte G. Dorner, et al., "Selective Expression of the Chemokine Receptor XCR1 on Cross-presenting Dendritic Cells Determines Cooperation with DC8+ T Cells", in Immunity, vol. 31, Nov. 20, 2009, pp. 823-833 (11 pgs.).
Vincent Flacher, et al., "Murine Langerin+ dermal dendritic cells prime CD8+ T cells while Langerhans cells induce cross-tolerance", in EMBO Molecular Medicine, vol. 6, No. 9, 2014, pp. 1191-1124 (14 pgs.).
Reinhold Forster, et al., "CCR7 Coordinates the Primary Immune Response by Establishing Functional Microenvironments in Secondary Lymphoid Organs", in Cell, vol. 99, 1999, pp. 23-33 (12 pgs.).
Even Fossum, et al., "Vaccine molecules targeting Xcr1 on cross-presenting DCs induce protective CD8+ T-cell responses against influenza virus", in Eur. J. Immunol., vol. 45, 2015, pp. 624-635 (12 pgs.).
Michael Y. Gerner, et al., "Strategically Localized Dendritic Cells Promote Rapid T Cell Responses to Lymph-Borne Particular Antigens", in Immunity, vol. 42, pp. 172-185 (15 pgs.).
Josh Gregorio, et al., "Plasmacytoid dendritic cells sense skin injury and promote wound healing through type I interferons", in the Journal of Experimental Medicine, vol. 207, No. 13, pp. 2921-230 (10 pgs.).
Marin Guilliams, et al., "Skin-draining lymph nodes contain dermis-derived CD103-dendritic cells that constitutively produce retinoic acid and induce Foxp3+ regulatory T cells", in Blood, vol. 115, No. 10, Mar. 11, 2010, pp. 1958-1968 (12 pgs.).
Muzlifah Haniffa, et al., "Ontogeny and Functional Specialization of Dendritic Cells in Human and Mouse", in Advances in Immunology, vol. 120, 2013, pp. 1-49 (49 pgs.).
Evelyn Hartung, et al., "Induction of Potent CD8 T Cell Cytotoxicity by Specific Targeting of Antigen to Cross-Presenting Dendritic Cells in Vivo via Murine or Human XCR1", in J. Immunol., vol. 194, 2015, pp. 1069-1079 (12 pgs.).
Sandrine Henri, et al., "CD207+ CD103+ dermal dendritic cells cross-present keratinocyte-derived antigens irrespective of the presence of Langerhans cells", in the Journal of Experimental Medicine, vol. 207, No. 1, 2010, pp. 189-206 (18 pgs.).
Kristin A. Hogquist, et al., "Pillars Article: T Cell Receptor Antagonist Peptides Induce Positive Selection", Cell, vol. 76, 1994, pp. 17-27 (12 pgs.).
Andrea A. Itano, et al., "Distinct Dendritic Cell Populations Sequentially Present Antigen to CD4 T Cells and Stimulate Different Aspects of Cell-Mediated Immunity", in Immunity, vol. 19, Jul. 2003, pp. 47-57 (11 pgs.).
Olivier P. Joffre, et al., "Efficient and versatile manipulation of the peripheral CD4+ T-cell compartment by antigen targeting to DNGR-1/CLEC9A", Eur. J. Immunol., vol. 40, 2010, pp. 1255-1265 (11 pgs.).
Sarah L. Jongbloed, et al., "Human CD141+ (BDCA-3)+ dendritic cells (DCs) represent a unique myeloid DC subset that cross-presents necrotic cell antigens", in the Journal of Experimental Medicine, vol. 207, No. 6, pp. 1247-1260 (14 pgs.).
Wolfgang Kastenmüller, et al., "Dendritic cell-targeted vaccine3-hope or hype?", in Nature Reviews Immunology, vol. 14, Oct. 2014, pp. 705-711 (7 pgs.).
Adrien Kissenpfennig, et al., "Dynamics and Function of Langerhans Cells in Vivo: Dermal Dendritic Cells Colonize Lymph Node Areas Distinct from Slower Migrating Langerhans Cells", in Immunity, vol. 22, May 2005, pp. 643-654 (12 pgs.).
Jared Klarquist, et al., "STING-mediated DNA sensing promotes antitumor and autoimmune responses to dying cells", in J. Immunol. vol. 193, No. 12, Dec. 15, 2014, 26 pgs.
Martin Kreutz, et al., "Targetign dendritic cells—why bother?", in Blood, vol. 121, No. 15, Apr. 2013, pp. 2836-2844 (10 pgs.).
Jessica Li, et al., "Antibodies targeting Clec9A promote strong humoral immunity without adjuvant in mice and non-human primates", in Eur. J. Immunol., vol. 45, 2015, pp. 854-864 (11 pgs.).
Bernard Malissen, et al., "The origins and functions of dendritic cells and macrophages in the skin", in Nature Reviews Immunology, vol. 14, Jun. 2014, pp. 417-428 (12 pgs.).

(56) References Cited

OTHER PUBLICATIONS

Manolis Pasparakis, et al., "Mechanisms regulating skin immunity and inflammation", in Nature Reviews Immunology, vol. 14, May 2014, pp. 289-301 (13 pgs.).
David Sancho, et al., "Tumor therapy in mice via antigen targeting to a novel, DC-restricted C-type lectin", in the Journal of Clinical Investigation, vol. 118, No. 6, Jun. 2008, pp. 2098-2110 (13 pgs.).
Sandra Scheiblhofer, et al., "Laser microporation of the skin: prospects for painless application of protective and terapeutic vaccines", in Expert Opinion Drug Delivery, vol. 10, No. 6, 2013, pp. 761-773 (13 pgs.).
Andreas Schlitzer, et al., "IRF4 Transcription Factor-Dependent CD11b+ Dendritic Cells in Human and Mouse Control Mucosal IL-17 Cytokine Responses", in Immunity, vol. 38, May 23, 2013, pp. 970-983 (14 pgs.).
Elena Shklovskaya, et al., "Epidermal and Dermal Dendritic Cells Display Differential Activation and Migratory Behavior While Sharing the Ability to Stimulate CD4+ T Cell Proliferation in Vivo", in the Journal of Immunology, vol. 181, 2008, pp. 418-430 (14 pgs.).
Sean P. Sullivan, et al., "Dissolving Polymer Microneedle Patches for Influenza Vaccination", in Nat. Med., vol. 16, No. 8, Aug. 2010, pp. 1-16 (16 pgs.).
Samira Tamoutounour, et al, "Origins and Functional Specialization of Macrophages and of Conventional and Monocyte-Derived Dendritic Cells in Mouse Skin", in Immunity, vol. 39, Nov. 14, 2013, pp. 925-938 (14 pgs.).
Dorothea Terhorst, et al., "Abstract A54: Laser-assisted intradermal delivery of Xcl1-specific fusion vaccines induces potent antitumor response", in Cancer Immunology Research, Oct. 2015, 1 pg.
Dorothea Terhorst, et al, "Laser-Assisted Intradermal Delivery of Adjuvant-Free Vaccines Targeting XCR1+ Dendritic Cells Induces Potent Antitumoral Responses", in the Journal of Immunology, vol. 194, 2015, pp. 5894-5902 (9 pgs.).
Esther E. Weinberger, et al., "Generation of hypoallergenic neoglycoconjugates for dendritic cell targeted vaccination: A novel tool for specific immunotherapy", in Journal of Controlled Release, vol. 165, 2013, pp. 101-109 (9 pgs.).
Richard Weiss, et al., "Transcutaneous vaccination via laser microporation", in Journal of Controlled Release, vol. 162, 2012, pp. 391-399 (9 pgs).
Richard Weiss, et al., "New approaches to transcutaneous immunotherapy: targeting dendritic cells with novel allergen conjugates", in J. Curr. Opin. Allergy Clin. Immunol., vol. 13, No. 6, Dec. 2013, pp. 669-676 (8 pgs.).
Seng-Ryong Woo, et al., "STING-Dependent Cytosolic DNA Sensing Mediates Innate Immune Recognition of Immunogenic Tumors", in Immunity, vol. 41, No. 5, Nov. 20, 2014, pp. 1-24 (24 pgs.).
Jian-Guo Zhang, et al., "The Dendritic Cell Receptor Clec9A Binds Damaged Cells via Exposed Actin Filaments", in Immunity, vol. 36, Apr. 20, 2012, pp. 646-657 (12 pgs.).
Heng Sheng Sow et al.; "Combining low-dose or metronomic chemotherapy with anticancer vaccines A therapeutic opportunity for lymphomas"; OncoImmunology; vol. 2; Issue 12; Dec. 2013; pp. e27058-1-e27058-9.
Maria Tagliamonle et al.; "Novel metronomic chemotherapy and cancer vaccine combinatorial strategy for hepatocellular carcinoma in a mouse model"; Cancer Immunol Immunother, 2015; vol. 64, pp. 1305-1314; DOI 10.1007/s00262-015-1698-0.
Douglas Hanahan et al.; "Less is more, regularly: metronomic dosing of cytotoxic drugs can target tumor angiogenesis in mice"; the Journal of Clinical Investigation; vol. 105; No. 8; Apr. 2000; pp. 1045-1047.
Nicolas Penel et al.; "Cyclophosphamide-based metronomic chemotherapy: After 10 years of experience, where do we stand and where are we going?"; Critical Reviews in Oncology/Hematology; vol. 82; 2012; pp. 40-50.

\* cited by examiner

A

Pattern of CD4+ T cells in PBMCs during the immunization protocol

B

Pattern of CD8+ T cells in PBMCs during the immunization protocol

A

B

A

B

LASER-ASSISTED INTRADERMAL ADMINISTRATION OF ACTIVE SUBSTANCES

The invention relates to the laser-assisted intradermal administration of a pharmaceutical preparation and in particular a vaccine preparation. The invention further relates to the laser-assisted intradermal administration of antigens accompanied by repeated chemotherapy.

BACKGROUND

The unique immunological features of skin make it an attractive organ for vaccination and immunotherapy. Accessibility, high abundance of immune cells and efficient draining via lymphatics are considered main features of successful drug delivery and vaccination.

Dendritic cells (DCs) capture antigens in body barriers and migrate to lymph nodes (LNs), where they trigger the differentiation of antigen-specific, naive T cells into effector T cells. Recent studies identified a small number of DC subsets in the mouse that can be aligned with functionally equivalent human subsets (Haniffa et al, 2013, Adv Immunol 120: 1-49; Malissen et al, 2014, Nat Rev Immunol 14: 417-428). The XC-chemokine receptor 1 (XCR1) binds to a single ligand known as XCL1 and is expressed by a DC subset that has been previously characterized by the expression of CD8alpha, CD207 or CD103 (Bachem et al, 2012, Front Immunol 3: 214; Crozat et al, 2011, J Immunol 187: 4411-4415, Dorner et al, 2009, Immunity 31: 823-833). Mouse XCR1+ DCs excel in cross-presentation of self antigens (Bedoui et al, 2009, Nat Immunol 10: 488-495; Henri et al, 2010, J Exp Med 207: 189-206) and of dead tumor cell-associated antigens, a feature that is probably owing to their expression of the C-type lectin CLEC9A (also known as DNGR1)—a receptor for damaged and dead cell materials (Ahrens et al, 2012, Immunity 36: 635-645; Zhang et al, 2012, Immunity 36: 646-657). Targeting antigens to DCs has been successfully used to generate strong immune responses and entered clinical trials (Dhodapkar et al, 2014, DEC-205. Sci Trans) Med 6: 232ra251). For instance, when delivered intravenously in the presence of adjuvant, antigens chemically or genetically conjugated to CLEC9A antibody or to XCL1 elicit potent cytotoxic CD8+ T cell responses capable of destroying tumors (Caminschi et al, 2008, Blood 112: 3264-3273; Hartung et al, 2015, J Immunol 194: 1069-1079; Joffre et al, 2010, Eur J Immunol 40: 1255-1265; Li et al, 2014, Antibodies targeting Clec9A promote strong humoral immunity without adjuvant in mice and non-human primates. Eur J Immunol; Sancho et al, 2008, J Clin Invest 118: 2098-2110).

Owing to its high content of DCs, the skin is a particularly attractive site for vaccine administration. Efficacy of vaccines is highly dependent on the efficient delivery to professional antigen presenting cells, such as DCs. In particular, Langerhans cells (LC) are members of the dendritic cells family in the basal and suprabasal layers of the epidermis. LCs have strong immunogenic properties, encounter and uptake antigens in the peripheral tissues, transport them to regional lymph nodes, present to naïve T cells and initiate adaptive immune response. However, for ease of application, most vaccines that are used in mass vaccination programmes are not delivered into the epidermis or the dermis but into the hypodermis, which is a layer of fat and connective tissue just below the dermis with poorly characterized APCs. Such subcutaneous delivery bypasses the rich network of DCs that is found in the epidermis and dermis.

Several delivery systems have recently been developed to exploit the potential of skin DCs. For example, vaccination with microneedles—made from a biocompatible polymer—has been used to introduce influenza virus vaccine (Sullivan et al, 2010, Nat Med 16: 915-920) or live recombinant human adenovirus type 5 (Bachy et al, 2013, Proc Natl Acad Sci USA 110: 3041-3046) into the dermis, and those approaches have generated robust humoral and cellular immune responses. A portable laser, the Precise Laser Epidermal System (P.L.E.A.S.E), has been used to create micropores in the stratum corneum—the superficial impermeable layer of the skin—and the epidermis, allowing topically applied antigens to diffuse into the dermis and to induce potent immune responses (Weiss et al, 2012, J Control Release 162: 391-399). Vaccibodies are homodimeric chimeric proteins consisting of XCL1 chemokine, a hinge and an antigen moiety (Fossum et al, 2014, Vaccine molecules targeting Xcr1 on cross-presenting DCs induce protective CD8 T-cell responses against influenza virus. Eur J Immunol). They are intended to target antigens to cross-presenting XCR1+ DCs, and when used in a DNA format, flu hemagglutinin-containing vaccibodies protected mice against a lethal challenge with influenza A virus (Fossum et al. 2014).

Further, allergen-specific or pathogen-specific immunotherapy has been described via the transcutaneous route. Skin-resident antigen presenting cells (APCs) are responsible for mounting immune responses against invading pathogens. They sample the antigens at the skin and transport them into the secondary lymphoid organs where the adaptive immune response is initiated. APCs sense the antigen by pathogen recognition receptors such as Toll like receptors, NOD like receptors, and C-type lectin receptors (CLRs). CLRs are a group of receptors expressed by APCs that bind sugar structures commonly present in pathogens. Each APC cell population has a particular CLR expression pattern according to their function. Therefore, these molecules are considered as candidates for targeted antigen delivery and immune modulation. Recently, it was demonstrated that protein neoglycoconjugates can target APCs (Weinberger et al. J. Control Release 2013, 165(2)).

WO2009/044272A2 discloses vaccines co-administered with adjuvants, HSP70, for laser-based vaccination.

Hessenberger M. et al. report CpG-adjuvanted pollen allergen via laser-generated micropores (2013, Vaccine 31, 3427-3434).

WO2013/033496A2 discloses antigen administration after radiation.

WO2014/151403A1 describes a system for delivering an electromagnetic radiation to a target zone and a system for delivering a vaccine to said target zone.

Therapeutic vaccination is regarded also as promising strategy against various cancers like hematological malignancies including lymphoma or liver cancer due to hepatocellular carcinoma (Sow and Mattarollo, 2013, Oncoimmunology 2-12, e27058; Tagliamonte M et al., 2015, Cancer Immunol. Immunother., epub).

To avoid the problems of chemotherapeutic regimens based on maximum tolerated doses, metronomic chemotherapy is increasingly established making reference to the chronic, equally spaced administration of generally low doses of various chemotherapeutic drugs without extended rest periods. The treatment lies not only in its antitumor efficacy with very low toxicity, but also in a cell target switch, now aiming at tumor endothelial cells (Hanahan D et al., J. Clin. Invest. 2000, 105, 1045-7). The concept of metronomic chemotherapy includes the possibility of treating tumors that no longer respond to traditional chemotherapy.

Combinations of anticancer vaccines and low-dose or metronomic chemotherapy has been described and it has been evaluated whether said treatment regimens induce enhanced specific T cell response.

SUMMARY OF THE INVENTION

It is the object of the invention to provide an improved treatment of subjects in need of a therapy with pharmaceutical preparations, in particular immunotherapies to effectively induce an immune response. It is also the object of the invention to provide an improved treatment of subjects in need of an immunochemotherapy.

The object is solved by the claimed subject matter.

According to the invention, there is provided a vaccine preparation comprising an antigen linked to a binder of a dermal migratory antigen-presenting cell (APC) for use in the prophylactic or therapeutic treatment of a subject by intradermal administration through laser-generated micropores.

According to a further embodiment of the invention, there is provided an antigen linked to a binder of a dermal migratory antigen-presenting cell (APC) or a mixture of antigens wherein at least one of the antigens is linked to a binder of a dermal migratory APC for use in the prophylactic or therapeutic treatment of a subject by intradermal administration through laser-generated micropores.

According to an alternative embodiment of the invention, the use of an antigen linked to a binder of a dermal migratory antigen-presenting cell (APC) or a mixture of antigens wherein at least one of the antigens is linked to a binder of a dermal migratory APC for the preparation of a medicament for the prophylactic or therapeutic treatment of a subject is provided which medicament is administered by intradermal administration through laser-generated micropores.

In a specific embodiment, the vaccine preparation comprises an antigen moiety, an XCL1 chemokine and a dimerization unit made of the hinge and CH3 domain of human IgG3.

It was also shown that a combination of antigens administered by laser-assisted epidermal delivery with a repeated dose of a chemotherapeutic agent promote highly beneficial immunomodulatory effects and abrogate tumor-induced immune-suppression, thereby boosting vaccine-induced immune response and achieving therapeutically increased antineoplastic effect in cancer treatment compared to known combination therapies by administering the vaccine antigen by conventional means.

For chemotherapy, there are also provided antigens or a mixture of antigens, i.e. an antigen preparation, for use in the prophylactic or therapeutic treatment of a subject by intradermal administration through laser-generated micropores in combination with a chemotherapeutic agent which is administered parenterally or enterally at a dosage below its maximum tolerated dose (MTD).

Specifically, the chemotherapeutic agent can be provided via low-dose or high-dose metronomic administration.

Specifically, there is also provided a vaccine preparation comprising an antigen linked to a binder of a dermal migratory antigen-presenting cell (APC) or mixtures of antigens linked to binders of a dermal migratory APC for use in the prophylactic or therapeutic treatment of a subject by intradermal administration through laser-generated micropores. Administration of said vaccine preparation is specifically not accompanied by administration of a chemotherapeutic agent.

According to a specific aspect, the binder specifically recognizes a surface receptor of an APC, e.g. which is a human ligand or a fragment thereof with affinity to bind the human surface receptor.

In particular, the binder is a ligand which specifically recognises an APC expressing chemokine (C motif) receptor 1 (XCR1) and/or C—C chemokine receptor type 7 (CCR7). Specifically, any of the following may be used as a target specifically recognized by the ligand: C-type lectin receptors, CLECs including CLEC1A, CLEC1B, CLEC2A, CLEC2B, CD69 (CLEC2C), CLEC2D, CLEC2L, CLEC3A, CLEC3B, CLEC4A, CLEC4C, CLEC4D, CLEC4E, CLEC4F, CLEC4G, ASGR1, ASGR2 (CLEC4H2), FCER2 (CLEC4J), CD207 (CLEC4K), CD209 (CLEC4L), CLEC4M, CLEC5A, CLEC6A, CLEC7A (DNGR1), OLR1 (CLEC8A), CLEC9A (DNGR1), CLEC10A, CLEC11A, CLEC12A, CLEC12B, CD302 (CLEC13A), LY75 (CLEC13B), PLA2R1 (CLEC13C), MRC1 (CLEC13D), MRC2 (CLEC13E), CLEC14A, CLEC16A, CLEC17A; Myeloid C type lectin like receptor (MICL); XCR-1; DEC-205; Dectin like Dectin-2; Dectin-1; SIGNR-1; MMR; Langerin; TLR-4; TLR-2; AGC1; ATRNL1, BCAN, CD248; CD72; CD93; CHODL; CL-K1-Ia; CL-K1-Ib; CL-K1-Ic; CLECSF5; COLEC10; COLEC11; COLEC12; CSPG3FCER2; FREM1; HBXBP, LAYN; LOC348174; LOC728276, MAFA; MBL2; MGC34761; MICL; MRC1L1, OLR1, PKD1; PKD1L2; PLA2R1; PRG2; PRG3, REG1A; REG1B; REG3A; REG3G; REG4, SELE; SELL; SELP; SFTPA1; SFTPA2; SFTPA2B; SFTPD; SRCL, THBD, VCAN. According to a specific embodiment, the ligand specifically recognises an APC expressing a C-type lectin receptor.

Specifically, the vaccine preparation comprises the antigen in the form of a composite immunogen comprising the antigen and the ligand in the form of a molecule or a molecule complex, wherein the components are linked by chemical bonds or fusion, or also bound by electrostatic or affinity binding. According to a specific embodiment, a linker may be used for connecting the antigen with the ligand/binder, such as a hinge region, e.g. a hinge region of an immunoglobulin. A specific embodiment employs at least one of the following components:
  a. a ligand to the targeted APC surface receptor
  b. a hinge
  c. an immunogen, whereas such immunogen consists of at least one of the following:
    i. a cancer antigen
    ii. a bacterial, viral or parasitic antigen
    iii. an allergen
    iv. an auto-antigen
  or at least an immunorelevant epitope of any immunogen of the foregoing.

According to a specific embodiment, the invention provides for a method of treating a subject in need of prophylactic or therapeutic treatment with a vaccine preparation, comprising administering such vaccine preparation in an effective amount with or without an exogenous adjuvant.

According to a further specific embodiment, the invention provides for a method of treating a subject in need of prophylactic or therapeutic treatment with an antigen or mixture of antigens, comprising administering such antigens in an effective amount with or without an exogenous adjuvant together with a chemotherapeutic agent that is given by metronomic enteral or parenteral administration.

The exogeneous adjuvant is herein understood as a heterologous chemical or biological material or substance which is commonly used to enhance the active immune response following vaccination or administration with an antigen. Typically, an exogenous adjuvant would be alum, e.g. as phosphate or hydroxide, TLR agonists, such as CpG or monophosphoryl lipid A or montanide.

By such intradermal route, the immune response can be effectively primed without such exogenous adjuvant. Still, the vaccine preparation comprising an antigen linked to a binder or antigens or a mixture of antigens may be used together with adjuvants to further improve the immune response and efficacy.

According to a specific embodiment, a physical adjuvant may be used, e.g. adjuvantation by physical means conferred by the laser-assisted administration.

Specifically, the antigen is selected from the group consisting of a tumor-associated antigen, a self-antigen (e.g. an auto-antigen), a microbial antigen (e.g. a bacterial, viral or parasitic antigen), an allergen, or an antigen comprising an immunorelevant epitope of any of the foregoing.

Specifically, the antigen is administered in an effective amount to elicit local T-cell response at the draining lymph node, and optionally systemic T-cell response.

Specifically, the preparation, i.e the vaccine preparation or the antigen preparation or a pharmaceutical preparation comprising an antigen preparation or vaccine preparation, is repeatedly administered. The repeated administration may be within the same priming area or within different priming areas. For example, the repeated administration can be at different locations within the same priming area to boost the immune response. According to another example, the repeated administration can be at different locations within the two or more priming areas to spread the immune response throughout the body.

In particular, for repeated administration of a vaccine preparation comprising an antigen linked to a binder of a dermal migratory APC, an antigen preparation comprising an antigen or a mixture of antigens for combined administration with chemotherapeutic agents or an immune modulator, it may be preferred to repeatedly administer the preparation within the same priming area, yet at different locations.

The priming area is typically a predetermined area, wherein the permeation surface over time is determined according to the patient's personal characteristics. In a parallel, serial or repeated administration setting, typically at least one preparation is administered at a first location, and a further preparation (or the same preparation at a different time point) is administered at a different location.

Specifically, the priming area is in close proximity to a target location to regionally deliver the antigen to the target location. Typically, the main area of priming is a regional lymph node. For example, the priming area is within 30 cm distance to the draining lymph node which is closest to the target location, or within 25 cm or within 20 cm. This provides for a regional administration near a lymph node at the target location. The target location may be a site of affection, e.g. a site of a primary tumor or metastasis, or a site of infection or inflammation, or a site of allergic disease condition. On the other hand, the target location may be distant to the site of affection, e.g. where an immune response is intended offsite, so to enhance or stimulate a T cell response with a certain degree of anergy, or absent an anergic phenotype.

According to a specific embodiment for chemotherapy, an antigen preparation is provided which comprises at least one antigenic peptide, specifically 2, 3, 4, 5, or more different peptides.

Specifically, the preparation is a cancer vaccine comprising antigens. More particularly said antigenic peptides can be selected from Hepatitis antigens, specifically HCV.

According to an embodiment of the invention, the antigen preparation is a multi-peptide cocktail including at least one viral antigen peptide, specifically selected from the group of HCV antigens, and/or at least one universal tumor antigen, specifically selected from hTERT epitopes.

According to a further embodiment of the invention, the chemotherapeutic agent is a multi-drug cocktail of 2, 3, 4, 5 or more agents.

Specifically, the chemotherapeutic cocktail comprises at least one alkylating agent and/or at least one taxane.

According to a specific treatment regimen, a) a microporated surface comprising a plurality of micropores is produced at a predetermined permeation surface of the subject's skin by laser poration; and
b) the vaccine preparation comprising an antigen linked to the binder is topically applied onto the microporated surface.

Specifically, the antigen is administered in an effective amount to elicit local and/or systemic T-cell response.

According to a specific chemotherapy treatment regimen, a) a microporated surface comprising a plurality of micropores is produced at a predetermined permeation surface of the subject's skin by laser poration,
b) an antigen or a mixture of antigens or antigen containing preparations are topically applied onto the microporated surface, and
c) a chemotherapeutic agent is administered repeatedly in conjunction with the vaccine agent via enteral or parenteral application.

Specifically, the microporated surface is about 2- to 10-times smaller than a total inner surface of pores created by the laser poration.

Specifically, the vaccine preparation comprising an antigen linked to a binder of a dermal migratory APC or the antigen preparation comprising an antigen or mixture of antigens is applied in the form of an antigen-rich solution or emulsion or dispersion, preferably by a patch (skin patch), gel, cream, aqeuous solution, powder, tape, or spray. The invention further provides for a pharmaceutical preparation further comprising an active substance, for use in the prophylactic or therapeutic treatment of a subject by intradermal administration through laser-generated micropores, for regional delivery to a target location.

Said pharmaceutical preparation can also be administered in combination with a chemotherapeutic agent.

Specifically, the invention provides for a method of treating a subject in need of prophylactic or therapeutic treatment with such pharmaceutical preparation by intradermal administration through laser-generated micropores in an effective amount for regional delivery to a target location.

Optionally, a chemotherapeutic agent is repeatedly administered in combination with the pharmaceutical preparation. More specifically, a method is provided for inducing epitope-specific T lymphocyte response to an antigenic epitope by administering a combination of an antigen preparation via intra-dermal laser assisted administration and a chemotherapeutic agent which is metronomically administered at a dosage below its maximum tolerated dose.

Specifically, the subject is at risk of or suffering from an infectious disease or an immune disorder, such as selected from the group consisting of cancer, autoimmune disease or allergy, and the active substance is an immune modulator used in the treatment of such infectious disease or immune disorder.

Specifically, the active substance is an immune modulator, such as a substance priming the immune response, which is selected from the group consisting of an antigen, an antibody or antigen-binding fragment thereof, molecules of high or low molecular weight, a small molecule, peptide or protein (including derivatives of proteins, such as fusion proteins or complexes of proteins with non-proteinaceous substances), or combinations of any of the foregoing.

Specifically, the active substance is an immune modulator which is downmodulating the coinhibitory receptor CTLA-4, or the coinhibitory receptor, PD-1, or its ligand, PD-L1.

Specifically, the active substance is an antigen, wherein the antigen is selected from the group consisting of a tumor-associated antigen, a self-antigen, a microbial antigen, an allergen, or an antigen comprising an immunorelevant epitope of any of the foregoing.

More specifically, the active substance is linked to a binder of a dermal migratory APC.

According to the embodiment of the invention, the chemotherapeutic agent can be any agent that can be used for anti-tumor or anti-cancer treatment. Specifically, it has cytotoxic or anti-angiogenic effect. More specifically, the chemotherapeutic agent can be selected from alkylating agents, antimetabolites, anti-microtubule agents, topoisomerase inhibitors or cytotoxic antibiotics or any combinations or mixtures thereof.

More specifically, the chemotherapeutic agents are selected from mechlorethamine, cyclophosphamide, melphalan, chlorambucil, ifosfamide and busulfan, N-Nitroso-N-methylurea (MNU), carmustine (BCNU), lomustine (CCNU), semustine (MeCCNU), fotemustine, streptozotocin, dacarbazine, mitozolomide and temozolomide; aziridines including thiotepa, mytomycin and diaziquone, cisplatin, carboplatin and oxaliplatin, procarbazine hexamethylmelamine, methotrexate, pemetrexed, capecitabine, fluorouracil, alkaloids, taxanes like paclitaxel, docetaxel, irinotecan, topotecan, anthracyclines, actinomycin, bleomycin, plicamycin, mitomycin, doxorubicin and daunorubicin or any mixtures thereof.

The chemotherapeutic agent can be administered enterally or parenterally, for example but not limited to oral, intravenous, intradermal or subcutaneous route.

Specifically, the antigen is administered in an effective amount to elicit local T-cell response at the draining lymph node, and optionally systemic T-cell response.

Specifically, the inventive treatment can induce long-lasting memory T-cell responses resulting in resistancy to repeated tumor development. It can also be used to eradicate tumors that recur after a period of regression following the initial vaccination.

Moreover, a treatment or prevention regime of a subject with a therapeutically effective amount of a compound, the antigen or mixtures thereof or the antigen linked to a binder of a dermal migratory APC or mixtures thereof, as described herein may consist of a single administration, or preferably comprise a series of applications. For example, a compound may be administered at least once a year, at least once a half-year or at least once a month, or at least twice a month, or at least weekly. According to specific embodiments, the compounds may be administered to the subject from about one time per week to a daily administration for a given treatment.

The chemotherapeutic agent administered in combination with the antigen or mixtures of antigens can be administered at least once per week, specifically at least twice per week, specifically every two days, more specifically at least once per day.

The length of the treatment period depends on a variety of factors, such as the severity of the disease, either acute or chronic disease, the age of the patient, the concentration and the activity of the antigen or antibody format. It will also be appreciated that the effective dosage used for the therapy or prophylaxis may increase or decrease over the course of a particular treatment or prophylaxis regime. Changes in dosage may result and become apparent by standard diagnostic assays known in the art. In some instances, chronic administration may be required.

An effective amount of an antigen or an antigen linked to a binder of a dermal migratory APC as described herein may specifically be in the range of 0.01 µg-10 mg per dose, specifically 1-100 µg.

Though the vaccine preparation or the antigen preparation for combined treatment with chemotherapy may be administered by a single administration to achieve an immune response, specific embodiments refer to repeated administration. For example, the vaccine preparation or antigen preparation may be administered as a first dose followed by one or more booster dose(s), within a certain timeframe, according to a prime-boost immunization scheme to induce a long-lasting, efficacious immune response by the antigen. A preferred vaccination or administration schedule would encompass administration of three doses, e.g. a first dose on day 0, a second dose on day 5-40, and a third dose on day 10-100, preferably on days 0, 28 and 90. According to a preferred accelerated schedule the administration may be on days 0, 7 and 14.

Though the pharmaceutical preparation comprising the antigen linked to a binder of a dermal migratory APC antigen or mixtures thereof may be administered by a single administration to achieve immediate response or a bolus, specific embodiments refer to repeated administration, e.g. according to a long-term treatment regimen. Specifically, the pharmaceutical preparation is repeatedly administered. The repeated administration may be within the same priming (delivery) area or within different priming (delivery) areas. For example, the repeated administration can be at different locations within the same delivery area for local treatment. According to another example, the repeated administration can be at different locations within two or more delivery areas to deliver the active substance to two or more sites for local treatment, or to deliver the active substance throughout the body.

Specifically, the preparation is repeatedly administered within a priming or delivery area, preferably wherein the repeated administration is at different locations.

Specifically, the priming area is in close proximity to a target location to regionally (or locally) deliver the antigen to the target location.

According to a specific embodiment,
a) a microporated surface comprising a plurality of micropores is produced at a predetermined permeation surface of the subject's skin by laser poration; and
b) the pharmaceutical preparation is topically applied onto the microporated surface.

According to a specific embodiment,
a) a microporated surface comprising a plurality of micropores is produced at a predetermined permeation surface of the subject's skin by laser poration;

b) the pharmaceutical preparation comprising the antigen or mixtures of antigens is topically applied onto the microporated surface, and c) a chemotherapeutic agent is administered repeatedly, specifically by metronomic administration.

Specifically, the microporated surface is about two to ten times smaller than a total inner surface of pores created by the laser poration.

Specifically, the preparation is applied in the form of an antigen-rich solution or emulsion or dispersion, preferably by a patch, specifically a transdermal patch, gel, cream, adequous solution, powder, tape, or spray.

The transdermal patch offers a variety of significant clinical benefits over other dosage forms. Because transdermal drug delivery offers controlled release of the substance into the patient, it enables a defined blood-level profile, resulting in reduced systemic side effects and, sometimes, improved efficacy over other dosage forms. In addition, transdermal patches are user-friendly, convenient, painless, and offer multi-day dosing. Transdermal patches therefore offer improved patient compliance.

The present invention also provides a kit of parts comprising a set of administration units for intradermal administration through laser-generated micropores, each containing an antigen preparation, and a set of administration units for parenteral administration, each containing a chemotherapeutic agent, optionally together with a leaflet containing information on dosage and administration details.

FIGURES

FIG. 1. XCL1-mCherry vaccibodies specifically target XCR1$^+$ dermal DCs in vitro.

A Vaccibodies are homodimeric chimeric proteins consisting of the XCL1 chemokine, a dimerization unit made of the hinge and CH3 domain of human IgG3, and an antigen moiety such as OVA. To determine whether XCL1-based vaccibodies specifically bind to XCR1$^+$ dermal DCs, the antigenic moiety was replaced by mCherry, a red monomeric fluorescent protein.

B Among skin CD45$^+$MHCII$^+$ cells, LCs (CD11b$^+$CD24$^+$), XCR1$^+$ (CD11b$^-$CD24$^+$) DCs and CD11b$^+$ (CD11b$^+$CD24$^{low}$Ly-6C$^-$CD64$^-$) DCs and moDCs and macrophages were identified using the expression of CD24 and CD11b and of Ly-6C and CD64 (n=3).

C Single-cell suspensions prepared from the ear skin of B6 (WT) and Xcr1$^{-/-}$ mice were incubated with XCL1-mCherry vaccibodies and analyzed by flow cytometry as described in B. Shaded histograms correspond to control, XCL1-mCherry-unstained cell samples. Numbers in histograms indicate the percentage of XCL1-mCherry$^+$ cells (n=3).

Figure 2:
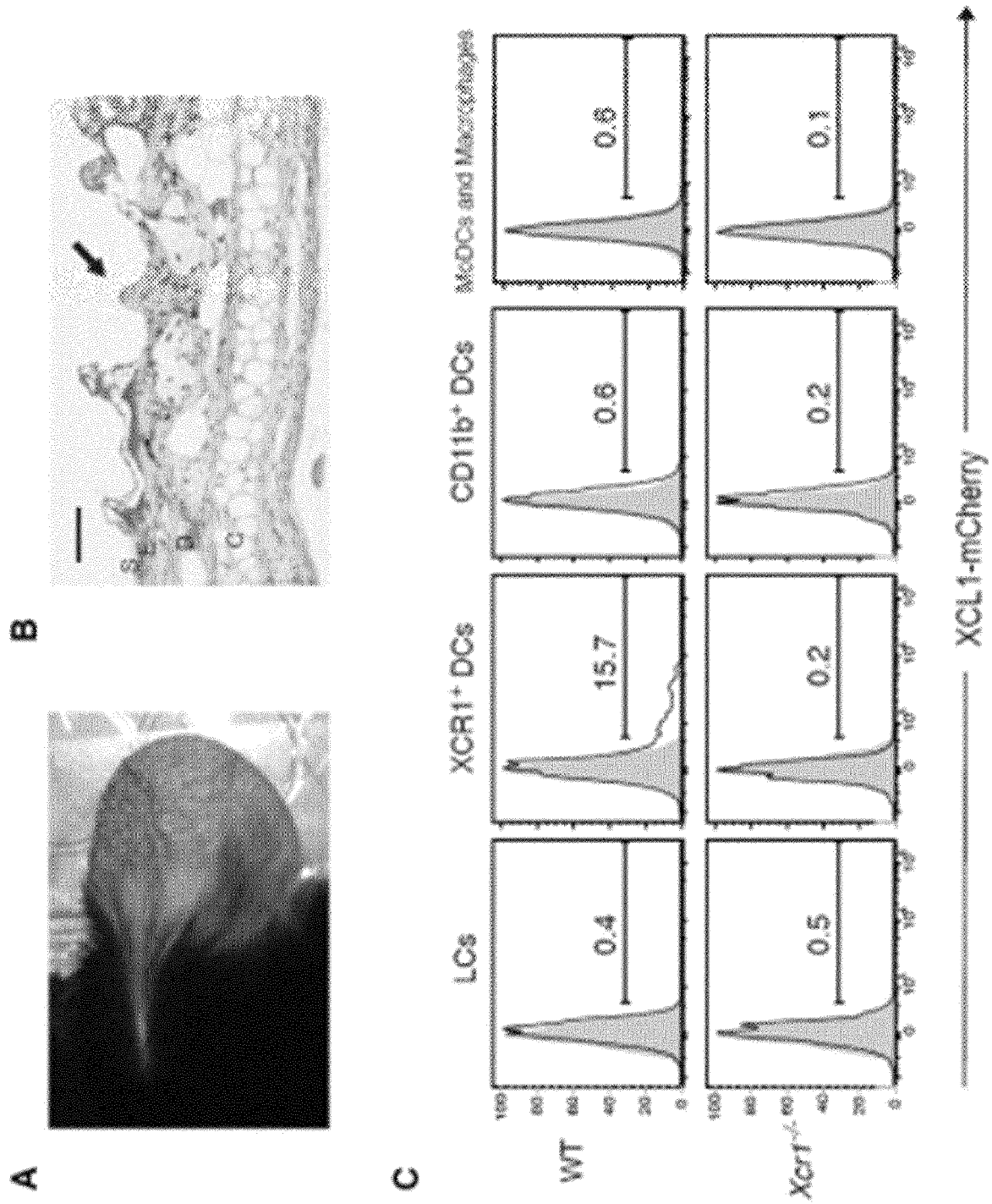

FIG. 2. Laser-assisted, dermal delivery of XCL1-mCherry vaccibodies permits the specific targeting of XCR1$^+$ dermal DCs.

A Macroscopic view of a mouse ear microporated with the P.L.E.A.S.E. portable laser at a power of 11.9 J/cm$^2$ (n=3).

B H&E staining of a representative ear section after laser microporation at a power of 11.9 J/cm$^2$. Stratum corneum (S), epidermis (E), dermis (D), and cartilage (C) regions of the ear are indicated. A micropore is denoted by an arrow. Scale bar: 100 μm (n=3).

C 24 h after application of XCL1-mCherry vaccibodies (3.8 μg in 20 μl of PBS) on laser microporated ear skin of B6 (WT) and Xcr1$^{-/-}$ mice, single-cell suspensions were prepared from the ear skin and the binding of XCL1-mCherry to LCs, XCR1$^+$ DCs, CD11b$^+$ DCs, moDCs and macrophages was analyzed by flow cytometry. Shaded histograms correspond to control, XCL1-mCherry-unstained cell samples. Numbers in histograms indicate the percentage of XCL1-mCherry$^+$ cells (n=3).

Figure 3:
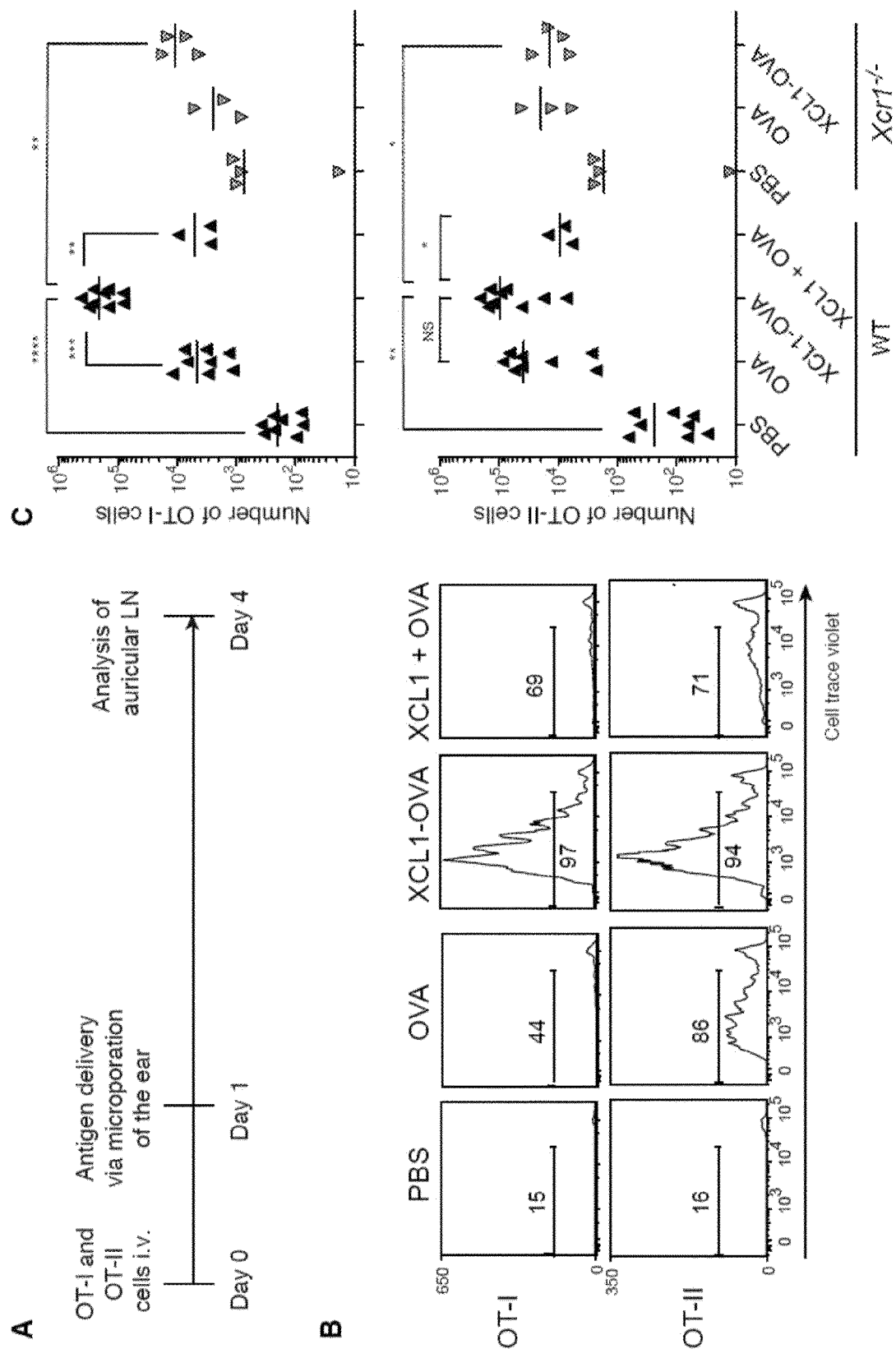

FIG. 3. Laser-assisted, dermal delivery of XCL1-OVA vaccibodies triggers potent OVA-specific CD4$^+$ and CD8$^+$ T cell proliferative responses.

A Time line of adoptive transfer of CTV-labeled OT-I and OT-II T cells, laser-assisted, dermal antigen delivery and analysis of OT-I and OT-II T cell proliferation within auricular, ear-draining LNs.

B Single-cell suspension were prepared from ear-draining, auricular LNs from B6 mice that received OT-I and OT-II T cells and were immunized by applying on laser-microporated ear 20 μl of PBS containing OVA (3.1 μg), XCL1-OVA vaccibodies (5 μg), XCL1 (1.8 μg) plus OVA (3.1 μg), or PBS alone as a control. CTV dilution of OT-I and OT-II T cells was measured 72 h after antigen delivery. Numbers in histograms indicate the percentage of divided T cells (n=3).

C Single-cell suspension were prepared from ear-draining, auricular LN from B6 (WT) and Xcr1$^{-/-}$ mice that were treated as in B. Absolute numbers of proliferating OT-I and OT-II T cells recovered per auricular LNs are shown for each individual mouse and the mean (horizontal bar) is indicated for each condition. *, p<0.001; , p<0.01; *, p<0.05 and NS: non significant.

Figure 4:
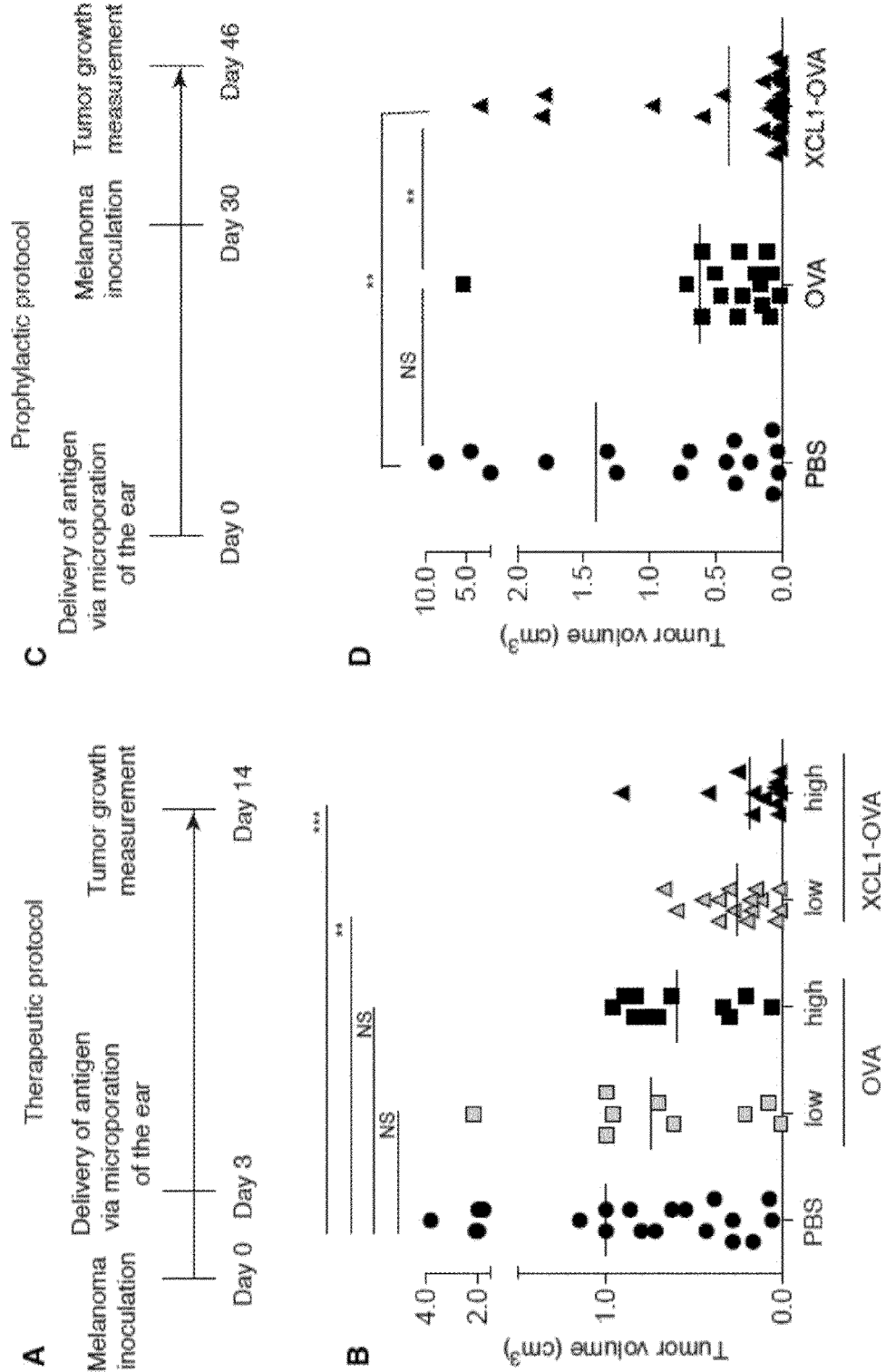

FIG. 4. Laser-assisted, dermal delivery of XCL1-OVA vaccibodies protects mice against melanoma tumor growth in therapeutic and prophylactic settings.

A Time line of the therapeutic setting involving subcutaneaous inoculation of the B16-OVA melanoma, laser-assisted, dermal delivery of OVA or XCL1-OVA vaccibodies, and tumor volume measurement.

B Cohort of mice treated as specified in A with 20 μl of PBS containing OVA (low dose: 1.5 μg or high dose: 3.1 μg), or XCL1-OVA vaccibodies (low dose 2.5 μg or high dose 5.0 μg) were analyzed for tumor volume. Control mice were treated with 20 μl of PBS. Tumor volume is shown for each individual mouse and the mean (horizontal bar) is indicated for each condition.*, p<0.001; , p<0.01; *, p<0.05 and NS: non significant.

C Time line of the prophylactic setting involving laser-assisted, dermal delivery of 20 μl of PBS containing OVA (1.5 μg) or XCL1-OVA vaccibodies (2.5 μg), subcutaneaous inoculation of the B16-OVA melanoma, and tumor volume measurement.

D Cohort of mice treated as specified in C with OVA or XCL1-OVA were analyzed for tumor volume. Control mice were treated with 20 μl of PBS. Tumor volume is shown for each individual mouse and the mean (horizontal bar) is indicated for each condition. *, p<0.001; , p<0.01; *, p<0.05 and NS: non significant.

Figure 5:
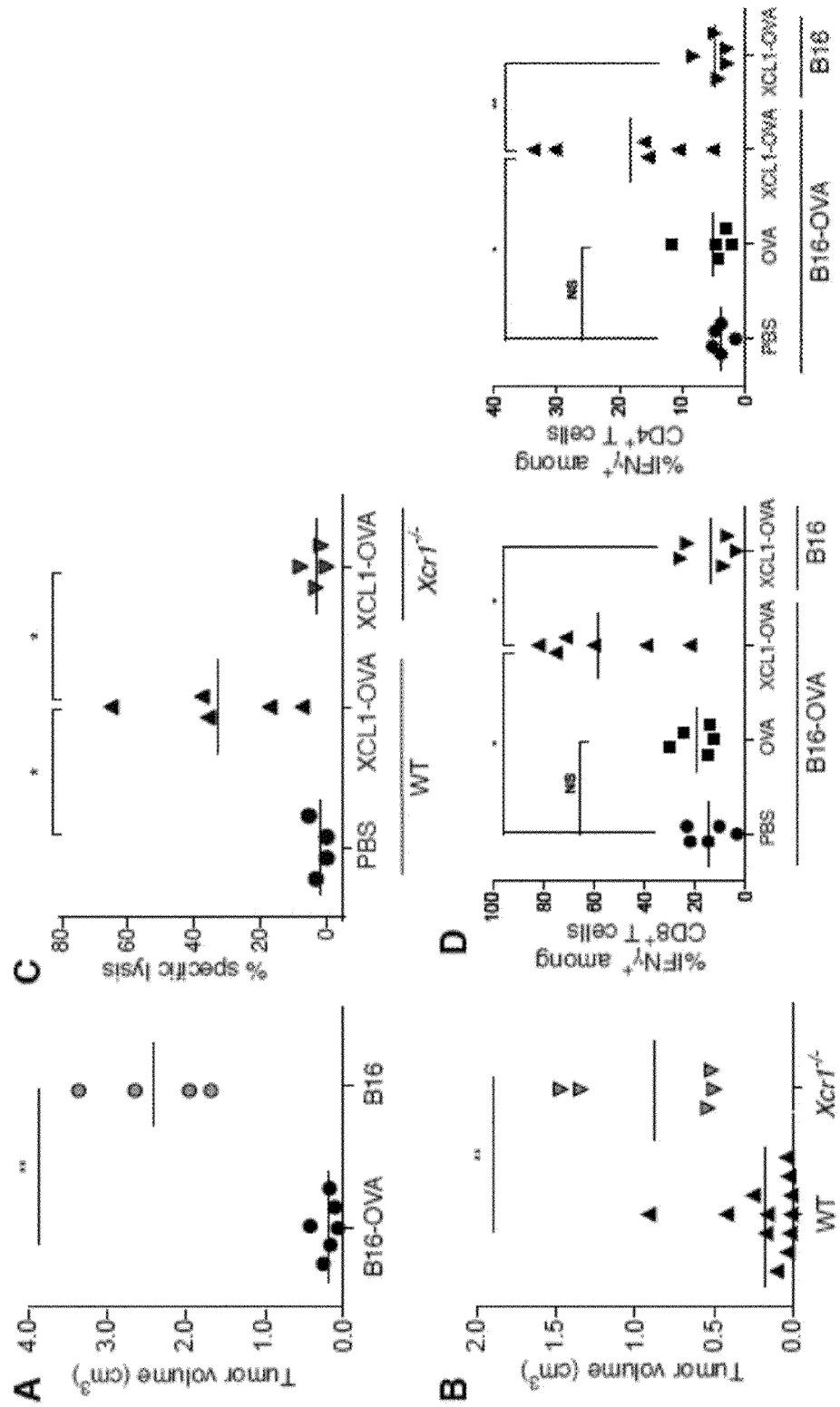

FIG. 5. Laser-assisted, dermal delivery of XCL1-OVA vaccibodies induces potent OVA-specific effector T cells in a XCR1-dependent manner.

A B6 mice were subcutaneously inoculated with B16-OVA or B16 melanoma, and immunized 3 days later with XCL1-OVA vaccibodies using laser-assisted, dermal delivery. On day 11 after immunization, the volume of the tumor developing in each mouse was determined. Data are shown for each individual mouse and the mean (horizontal bar) is indicated for each condition. **, p<0.01.

B B6 (WT) and Xcr1$^{-/-}$ mice treated as in A. On day 11 after immunization, the tumor volume was determined for each mice. Volumes are shown for each individual mice and the mean (horizontal bar) is indicated for each condition. **, p<0.01.

C B6 (WT) and Xcr1$^{-/-}$ mice were subjected to laser-assisted, dermal delivery of 20 µl of PBS containing OVA (1.5 µg) or XCL1-OVA (2.5 µg) vaccibodies or of 20 µl of PBS (control), or. On day 6, mice were injected with CFSE-labeled target cells to quantitate the induced OVA-specific cytotoxicity in vivo (see Materials and Methods). The percent specific lysis is shown for each individual mouse and the mean (horizontal bar) is indicated for each condition. *, p<0.05.

D B6 mice were subcutaneously inoculated with B16-OVA or B16 and immunized 3 days later with 20 µl of PBS containing OVA (1.5 µg) or XCL1-OVA (2.5 µg) vaccibodies using laser-assisted, dermal delivery. On day 11 after immunization, the tumor mass of each mouse was excised and the percentage of IFNγ$^+$ cells determined among tumor infiltrating CD8$^+$ and CD4$^+$ T cells. Data are shown for each individual mouse and the mean (horizontal bar) is indicated for each condition. **, p<0.01; *, p<0.05 and NS for non significant.

Figure 6:
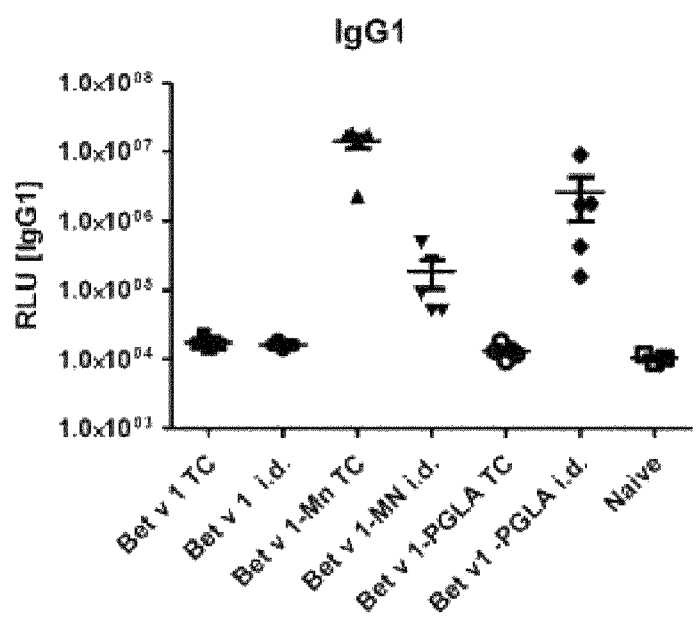

FIG. 6. IgG1 antibody titers of mice immunized intradermally (i.d.) or transcutaneously via laser-poration (TC) with Betv1 protein, Betv1-mannan glycoconjugates (Betv1-MN). Antibody titers were determined by ELISA using a chemiluminescence detection system. No antibody response was detected for Betv1 alone. Betv1-mannan transcutaneously showed antibody titers significantly higher than intradermal immunization with Betv1-mannan (p<0.001). Groups were compared using one way ANOVA and Tukey's multiple comparison tests. Statistical analysis was performed using Graphpad software.

Figure 7:
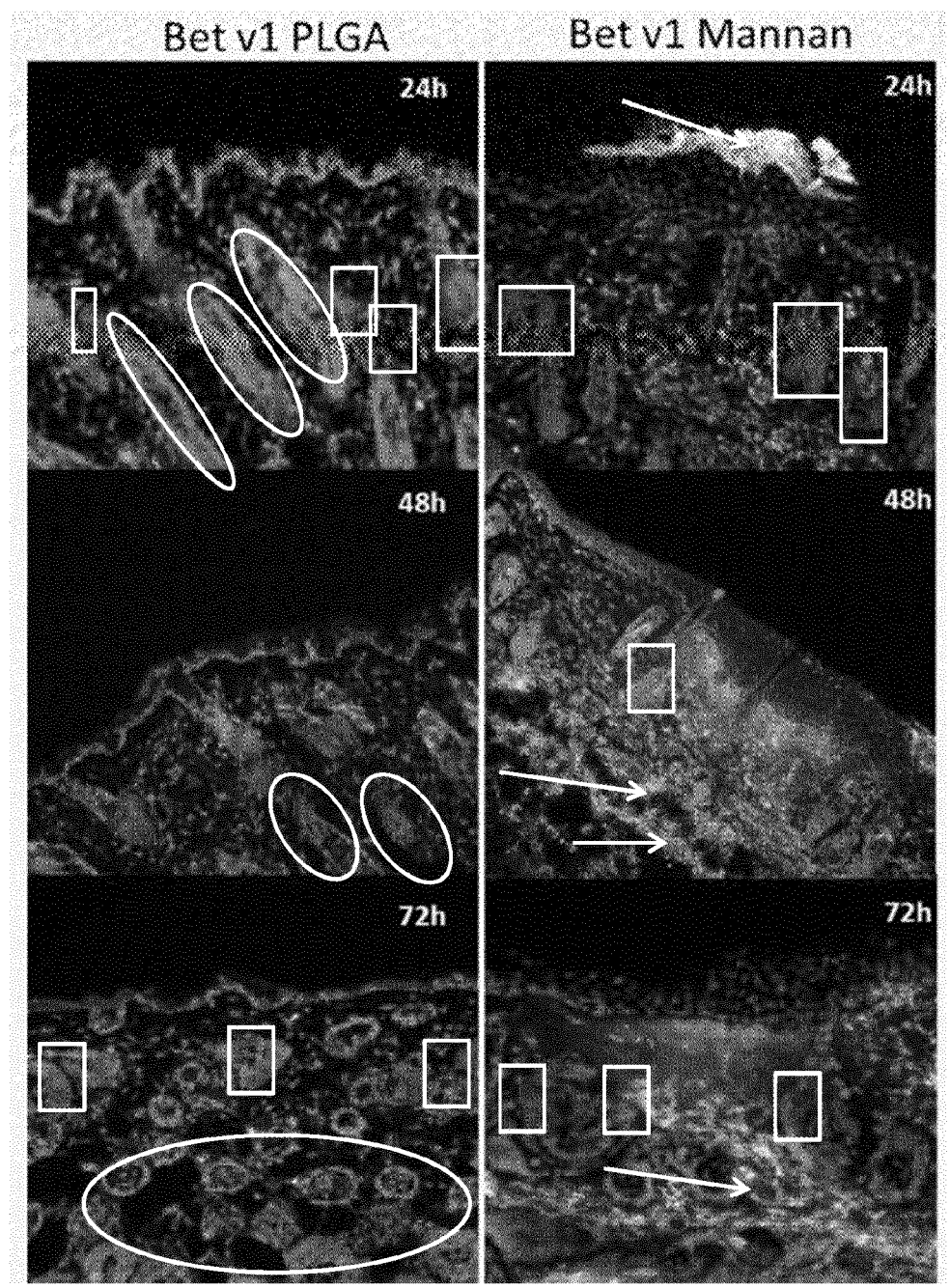

FIG. 7. Fluorescence microscopy of skin sections from mice immunized via laser-porated skin with FITC labelled Betv1-mannan or Betv1-PLGA. Skin sections were additionally stained with DAPI (white circles), CD11b-APC (white arrows) and CD11c-Cy3 (white rectangles). 72 hours after immunization, the epidermis is totally re-established and the antigen remains in the dermal compartment. PLGA nanoparticles showed a reduced antigen delivery and no cell infiltrate was induced.

Figure 8:
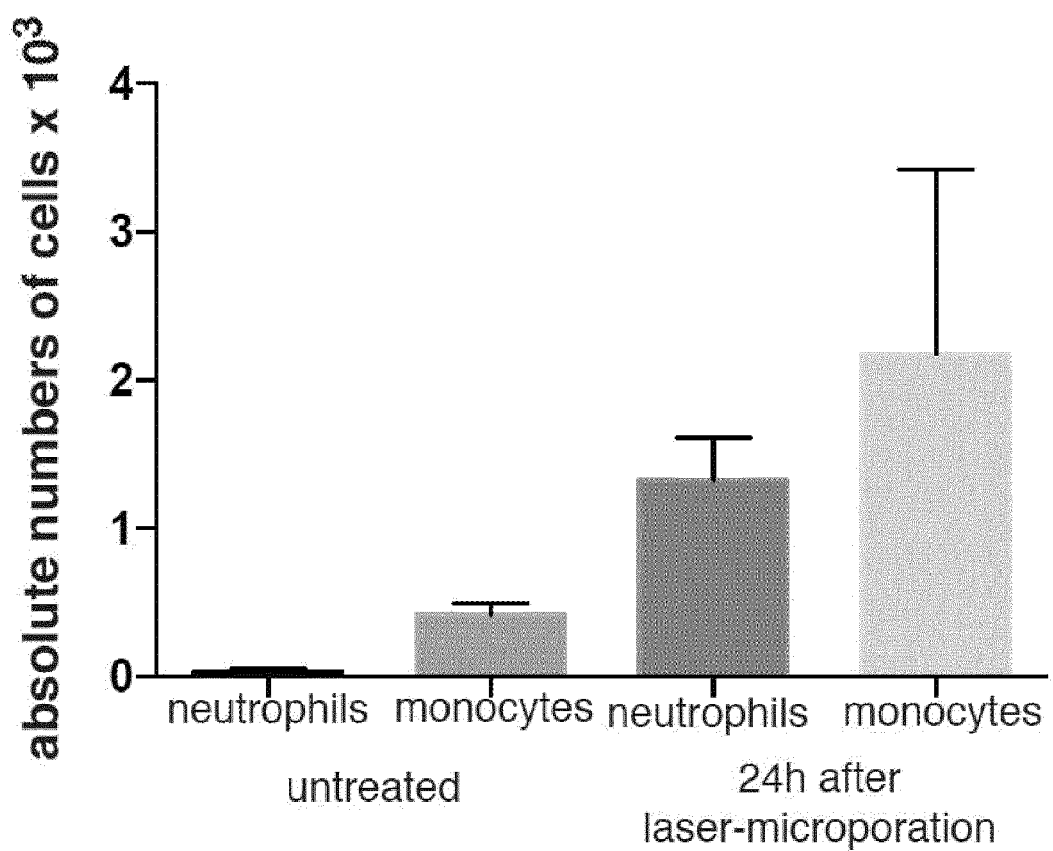

FIG. 8. Neutrophils and monocytes infiltrate the ears 24 hours after laser microporation.

A The ears of B6 (WT) mice were left untreated or laser-microporated as specified in Materials and Methods and no antigen was applied. 24 hours later, single cell suspensions were prepared from the ears and the absolute numbers of neutrophils and monocytes were assessed by flow cytometry. Neutrophils and monocytes were identified as described (Gregorio et al, 2010; Tamoutounour et al, 2013) (n=3).

Figure 9:
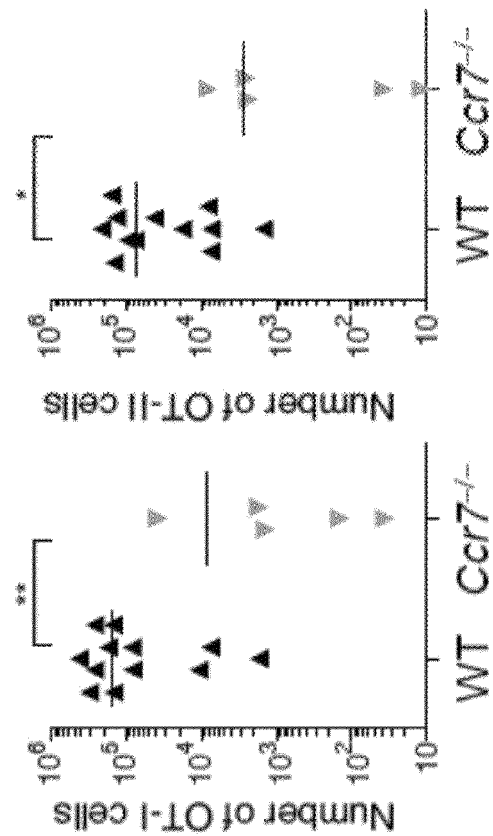
Figure 9:
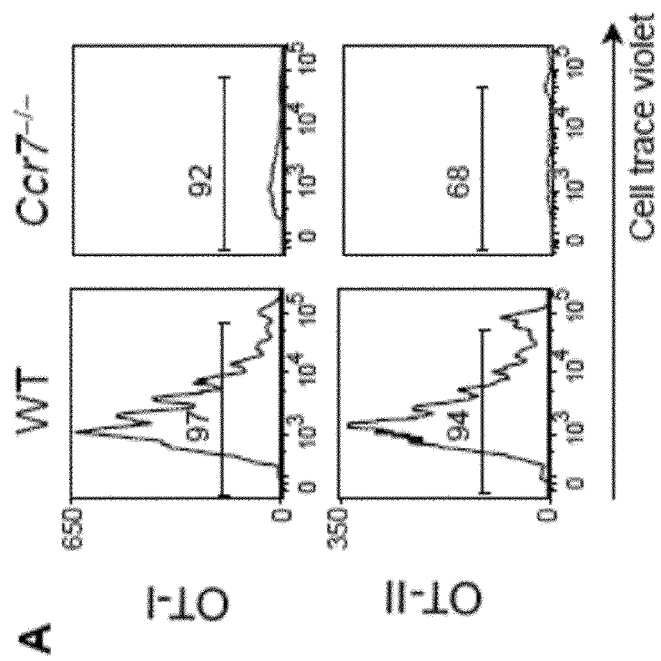

FIG. 9. T cell responses induced by dermal delivery of XCL1-OVA vaccibodies depend on dermal DC migration.

A, B B6 (WT) and Ccr7$^{-/-}$ mice received CTV-labeled OT-I and OT-II T cells and one day later their ears were microporated and treated with XCL1-OVA vaccibodies (5 µg in 20 µl of PBS). Seventy two hours later, single cell suspensions were prepared from the ear-draining auricular LN and CTV dilution (A) and the numbers (B) of OT-I and OT-II T cells were determined. In A, the numbers in histograms indicate the percentage of divided T cells (n=3), and in B, cell numbers are shown for each individual mouse and the mean (horizontal bar) is indicated for each condition. **, p<0.01.

Figure 10:
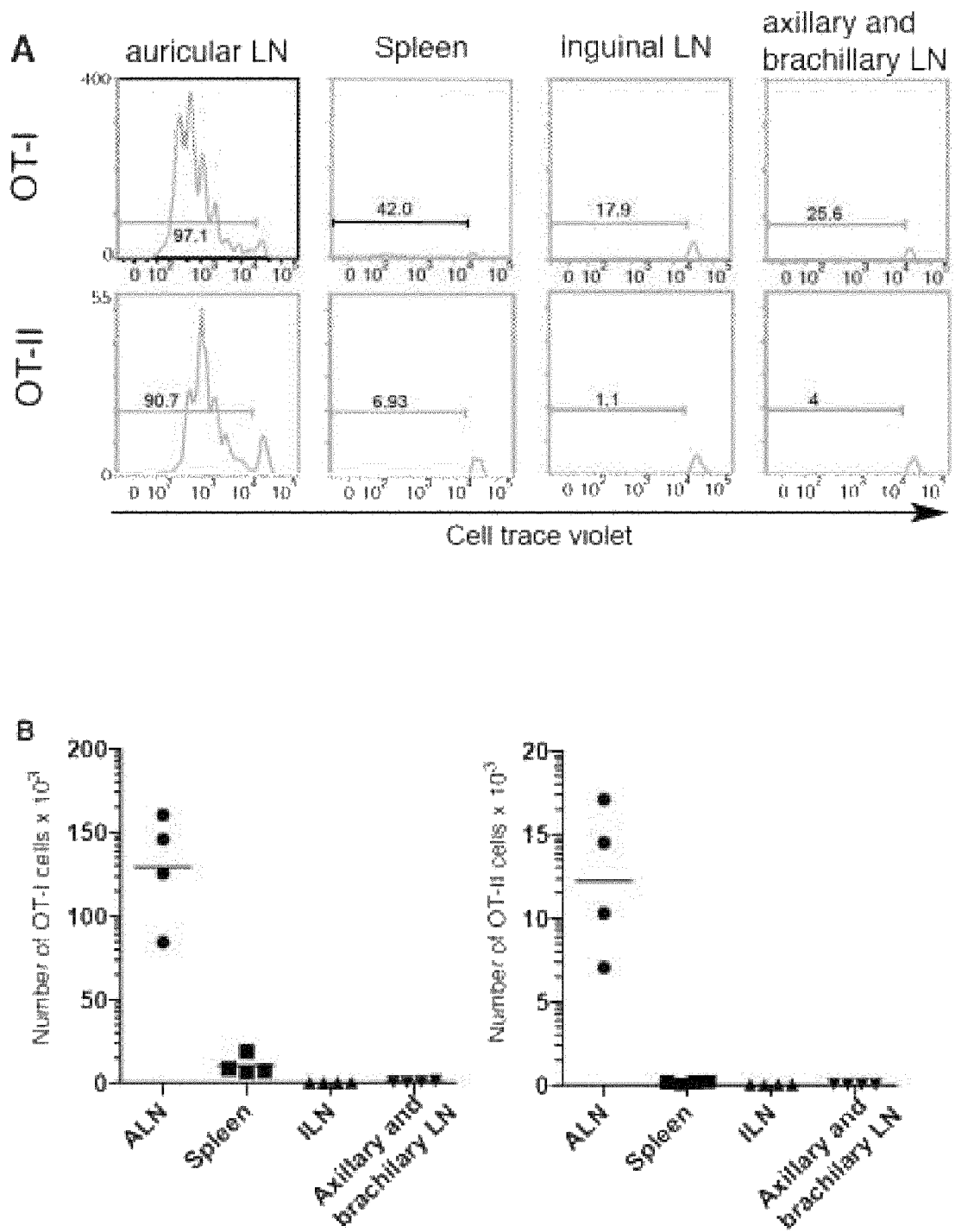

FIG. 10. Laser-assisted, intradermal delivery of XCL1-OVA vaccibodies results in T cell responses the onset of which is limited to the draining LNs.

A, B, C Mice were immunized with XCL1-OVA as in FIG. 3A. Seventy two hours after antigen delivery, single-cell suspension were prepared from spleen, inguinal, pooled axillary and brachial LNs and (A) CTV dilution of OT-I and OT-II T cells determined (n=2).

(B) Absolute numbers of proliferating OT-I and OT-II T cells recovered per indicated organ are shown for each individual mouse and the mean (horizontal bar) is indicated for each condition (n=2).

Figure 11:
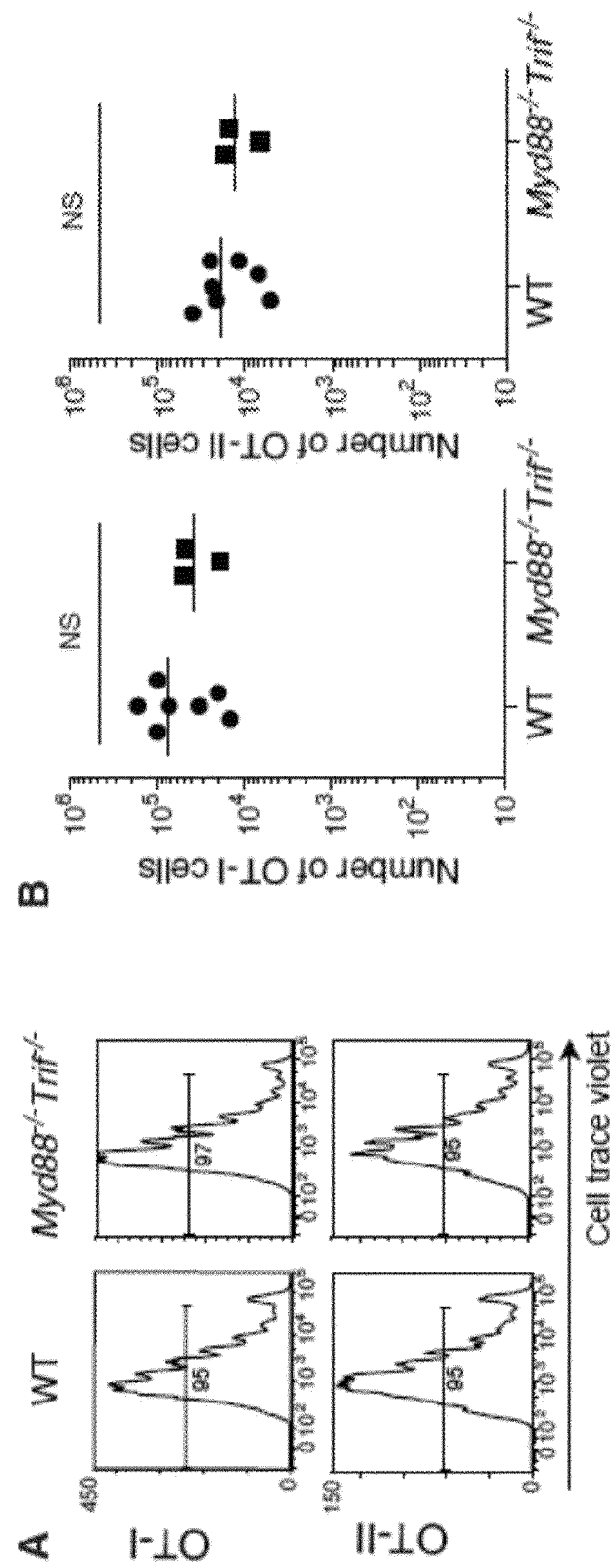

FIG. 11. T cell responses induced by intradermal delivery of XCL1-OVA vaccibodies occur independently of TLR signals.

A, B B6 (WT) and Myd88/Trif$^{-/-}$ mice received OT-I and OT-II T cells and one day later their ears were microporated and treated with XCL1-OVA vaccibodies (5 µg in 20 µl of PBS). Seventy two hours later, single cell suspensions were prepared from the ear-draining auricular LN and (A) CTV dilution of OT-I and OT-II T cells were determined (n=2). (B) Cell numbers are shown for each individual mouse and the mean (horizontal bar) is indicated for each condition. NS: non significant (n=2).

Figure 12:
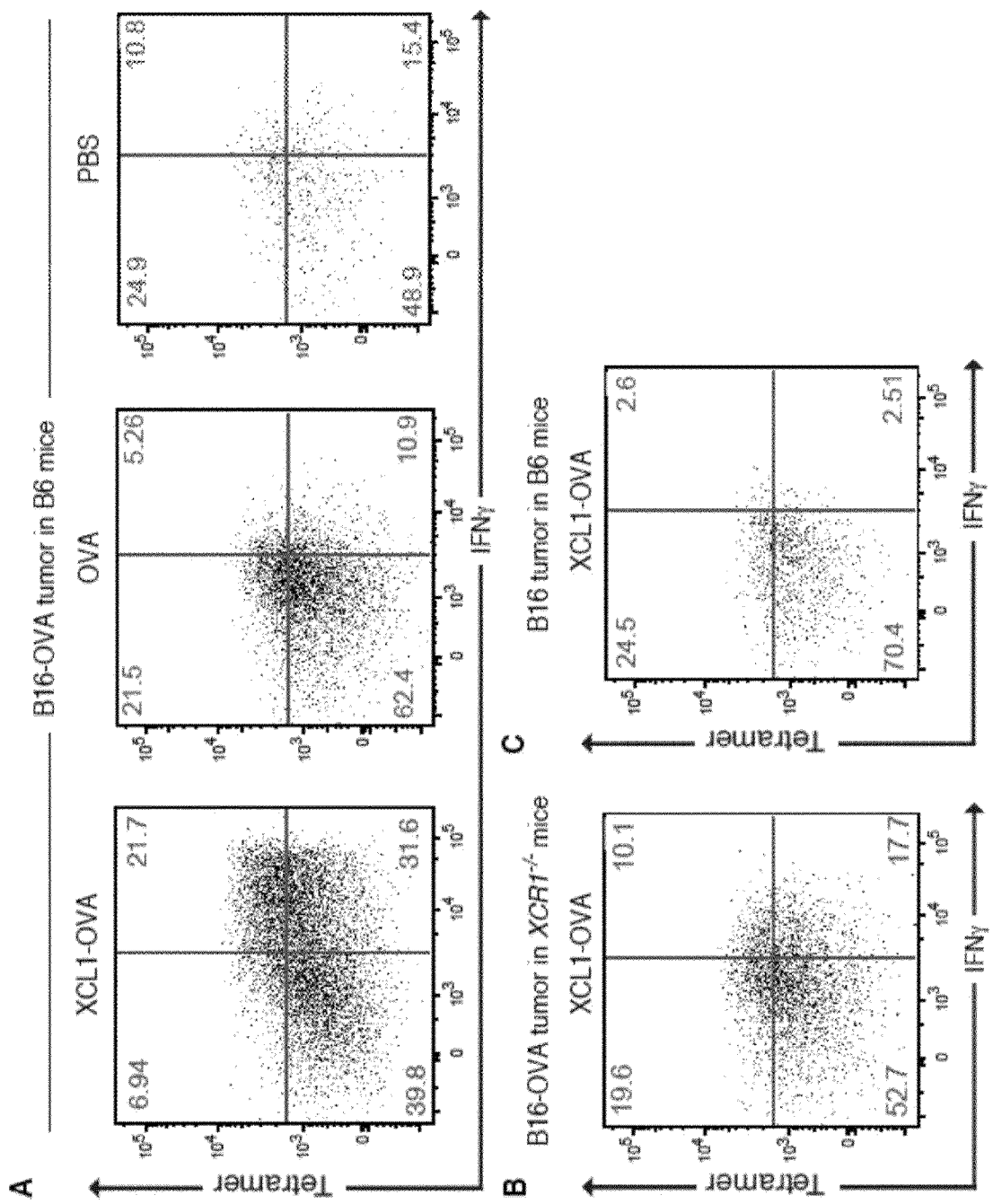

FIG. 12. IFNgamma$^+$ CD8$^+$ T cells infiltrating the B16-OVA tumor after laser-assisted intradermal immunization with XCL1-OVA vaccibodies are OVA-specific A, B, C Mice were immunized as in FIG. 4C. On day 46 after immunization, the tumor mass of each mouse was excised and the tumor-infiltrating CD8$^+$ and CD4$^+$ T cells were stained with H-2 K$^b$ tetramers loaded with the OVA-derived, SIINFEKL peptide. Percentages of tetramer$^+$ and IFNgamma$^+$ cells are shown among CD8$^+$ T cells isolated from tumor mass of mice treated with XCL1-OVA vaccibodies, free OVA or PBS as indicated. (A) B6 mice were immunized with XCL1-OVA or OVA or PBS prior to B16-OVA inoculation. (B) Xcr1$^{-/-}$ mice were immunized with XCL1-OVA prior to B16-OVA inoculation. (C) B6 mice were immunized with XCL1-OVA prior to B16 inoculation. (n=2)

Figure 13:
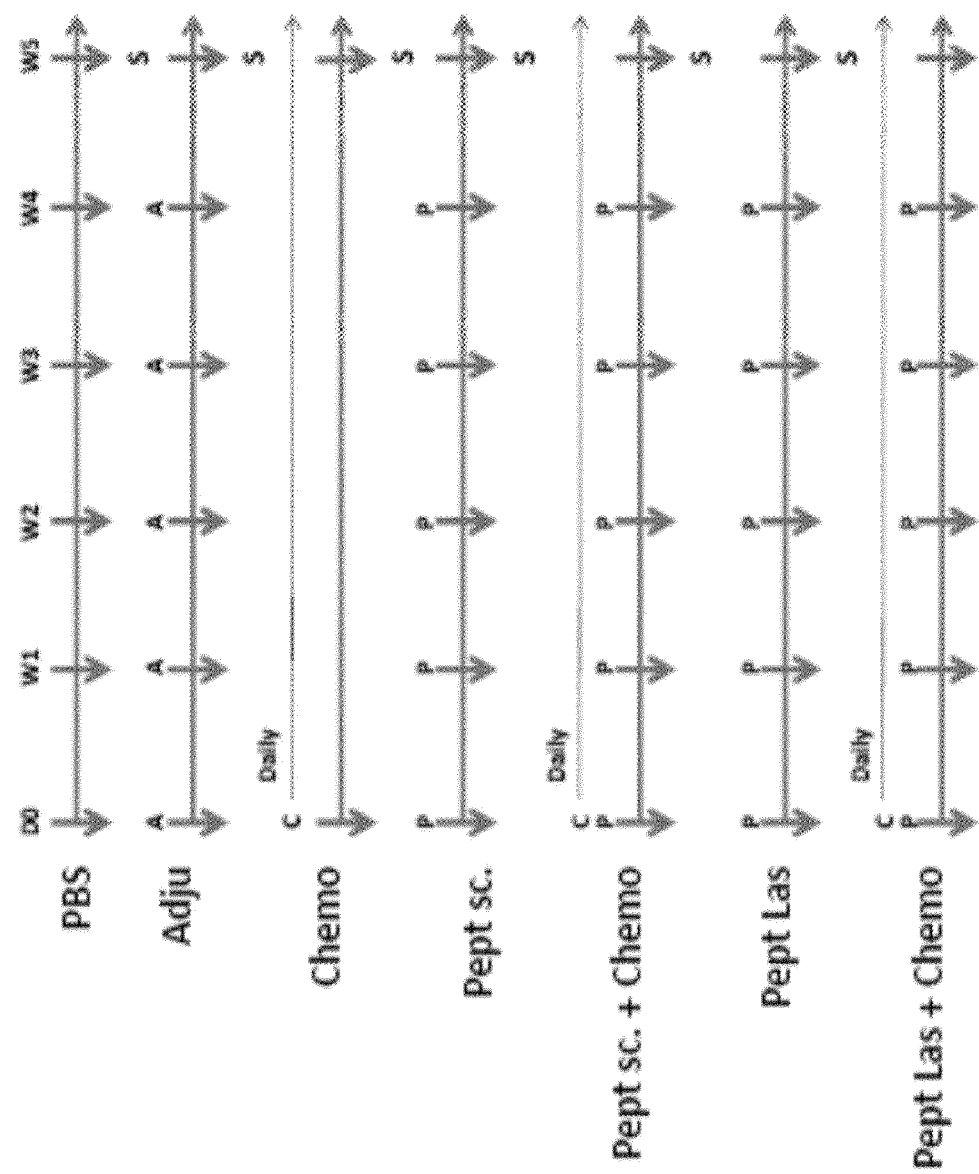

FIG. 13. Immunization protocol in C57BL/6 mice.

Figure 14:
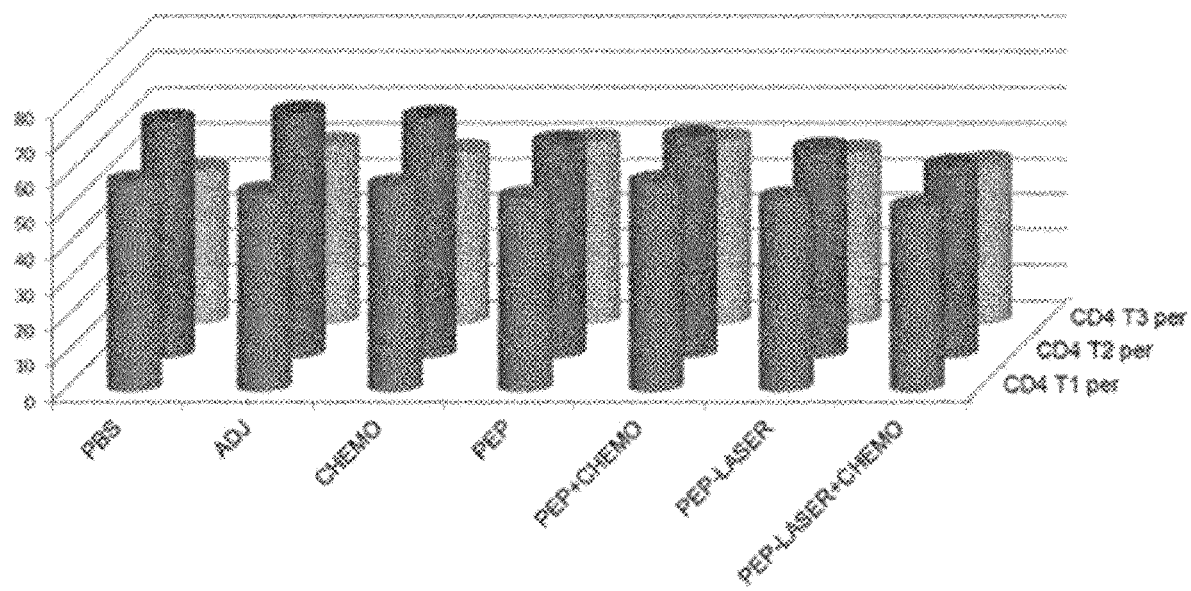
Figure 14:
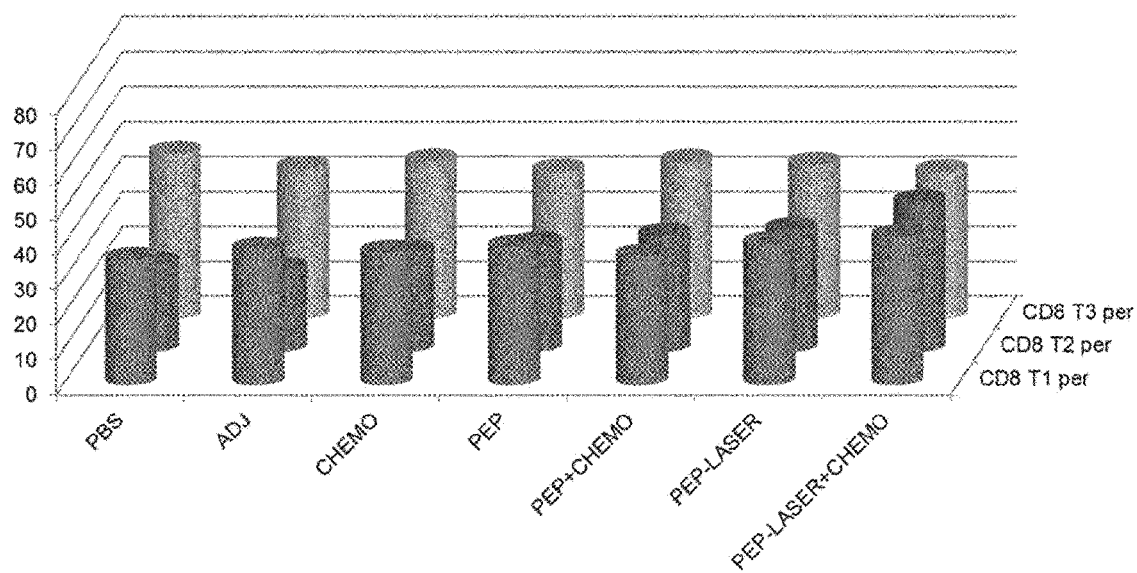

FIG. 14. Pattern of circulating CD4+ (A) and CD8+ (B) T cells during the immunization protocol.

Figure 15:
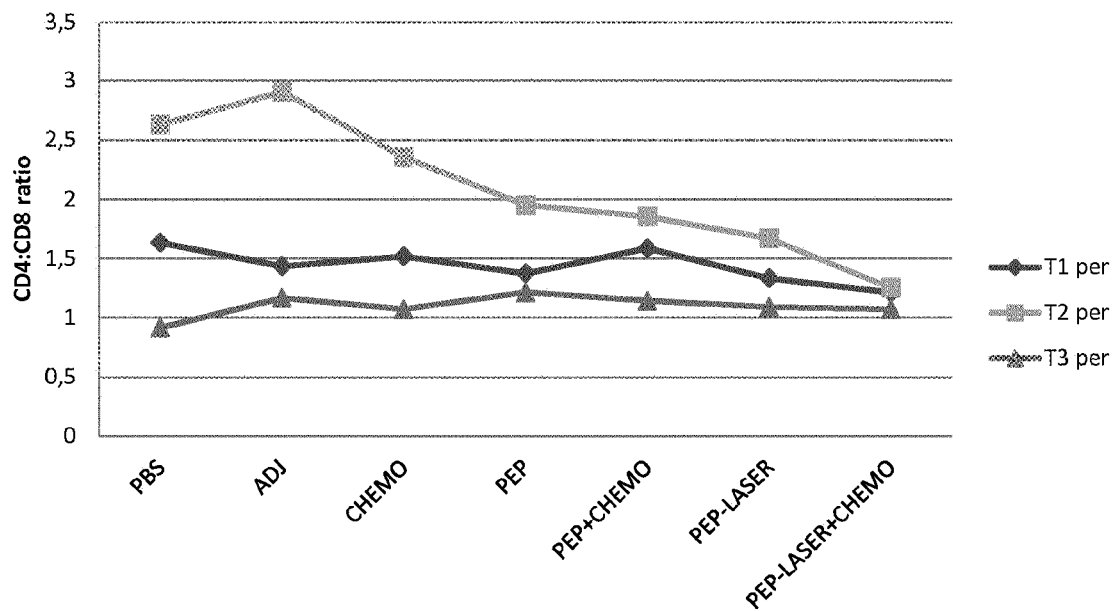
Figure 15:
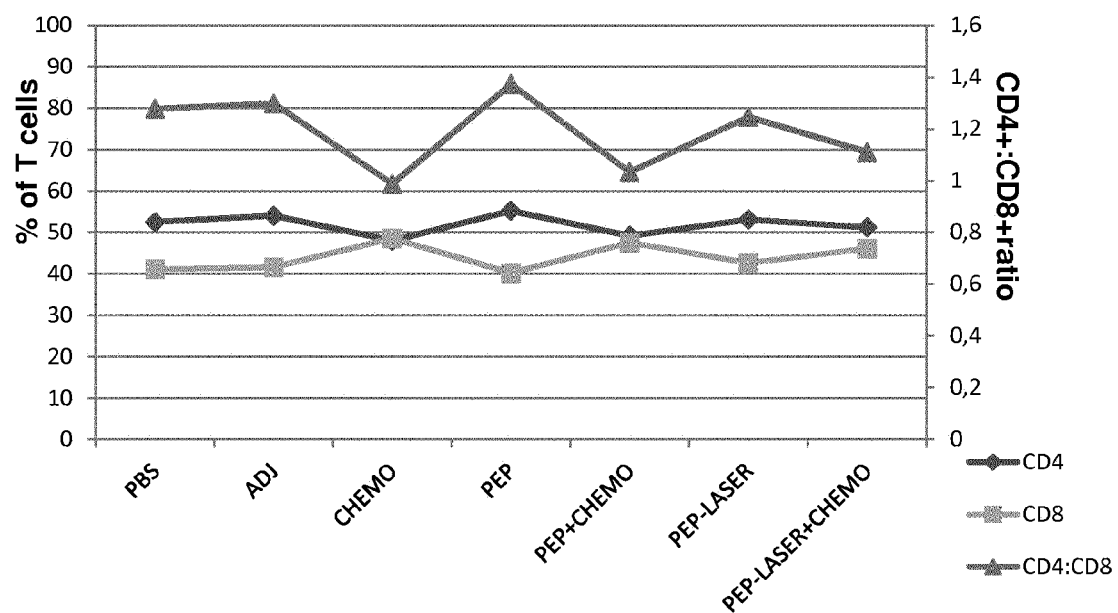

FIG. 15. Pattern of CD4:CD8 ration in PBMCs during the immunization protocol (A) and spleens (B) at the end of immunization protocol.

Figure 16:
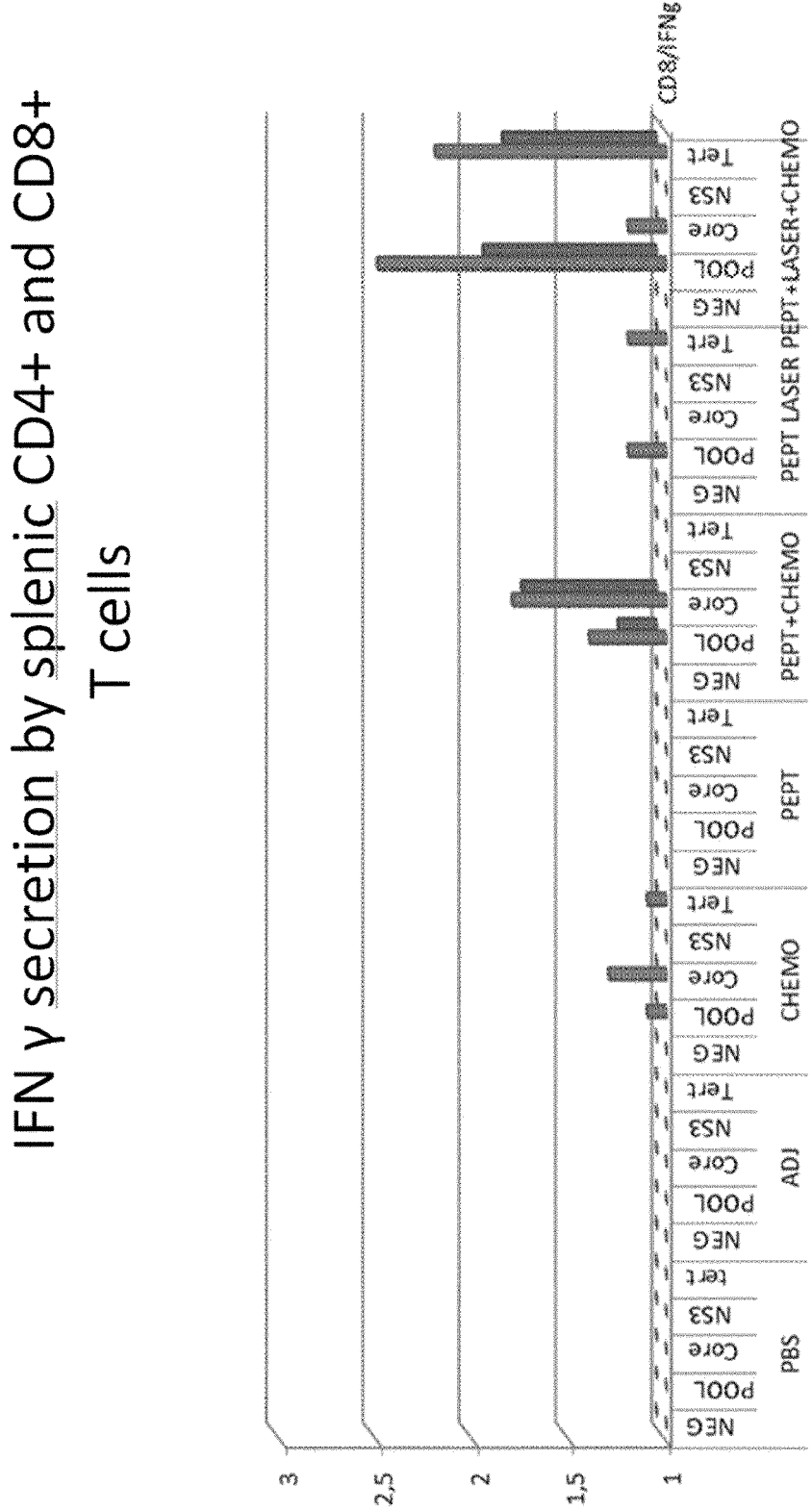

FIG. 16. IFN γ secretion by splenic CD8+ (A) and CD4+ T (B) cells.

Figure 17:
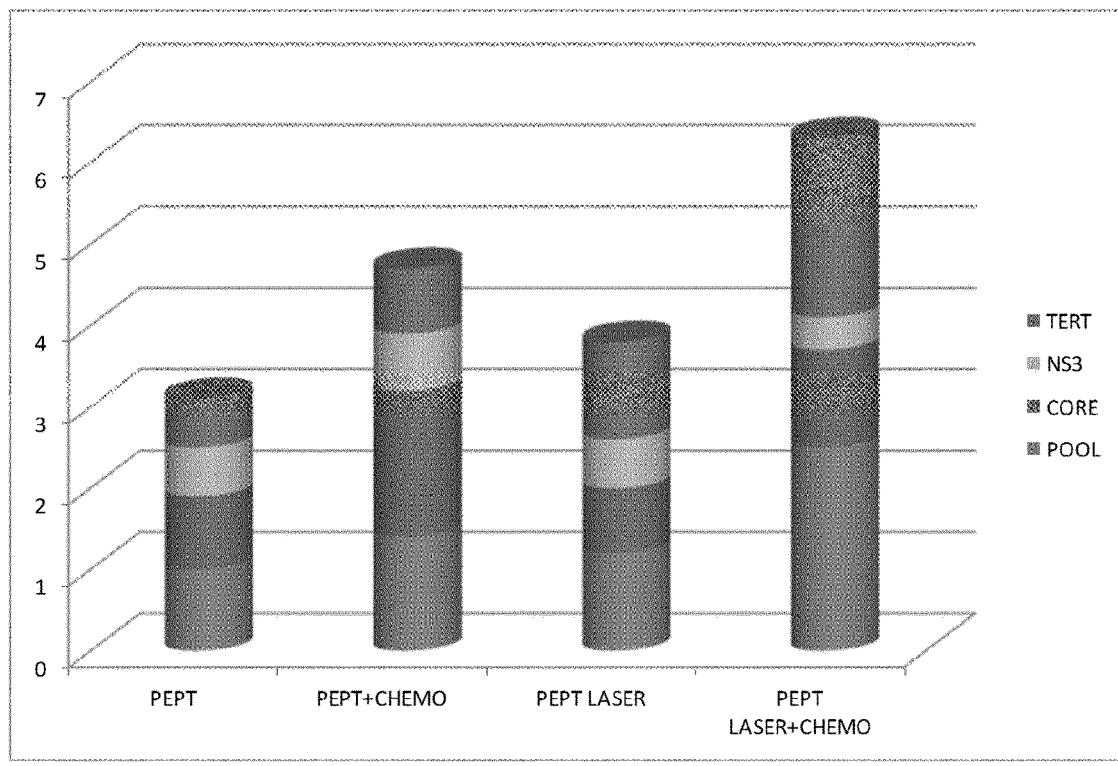
Figure 17:
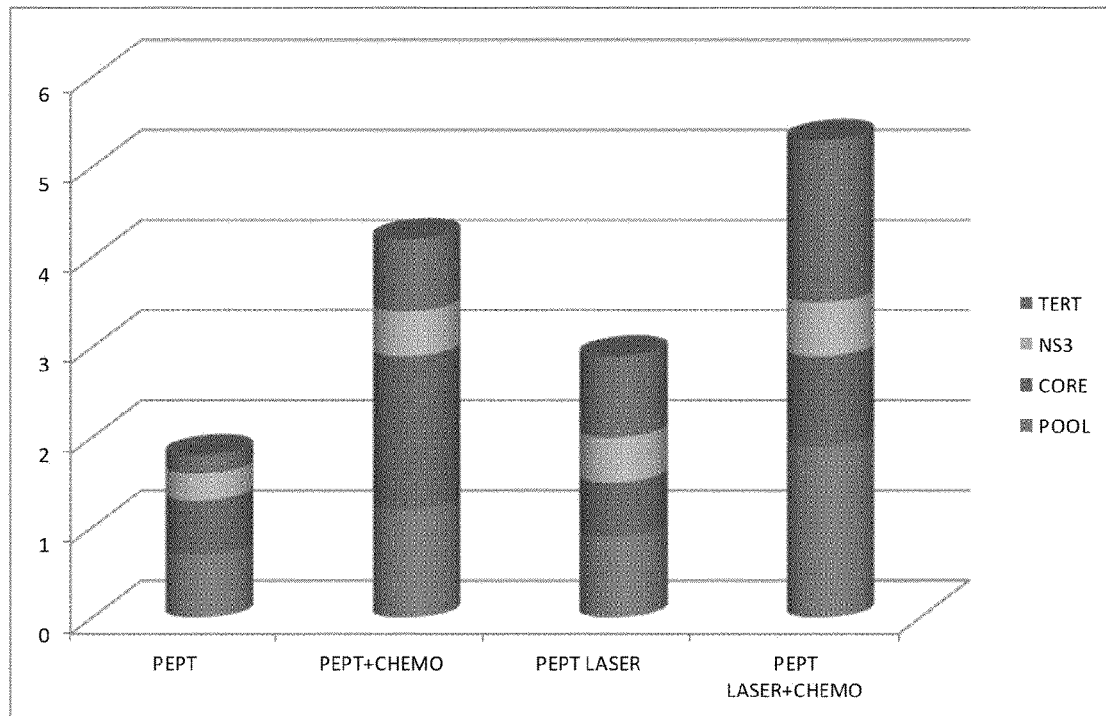

FIG. 17. Breadth and magnitude of epitope-specific T lymphocyte responses to vaccine peptides. First (bottom) segment: Pool; second segment: Core; third segment: NS3; fourth segment (top): TERT.

Figure 18:
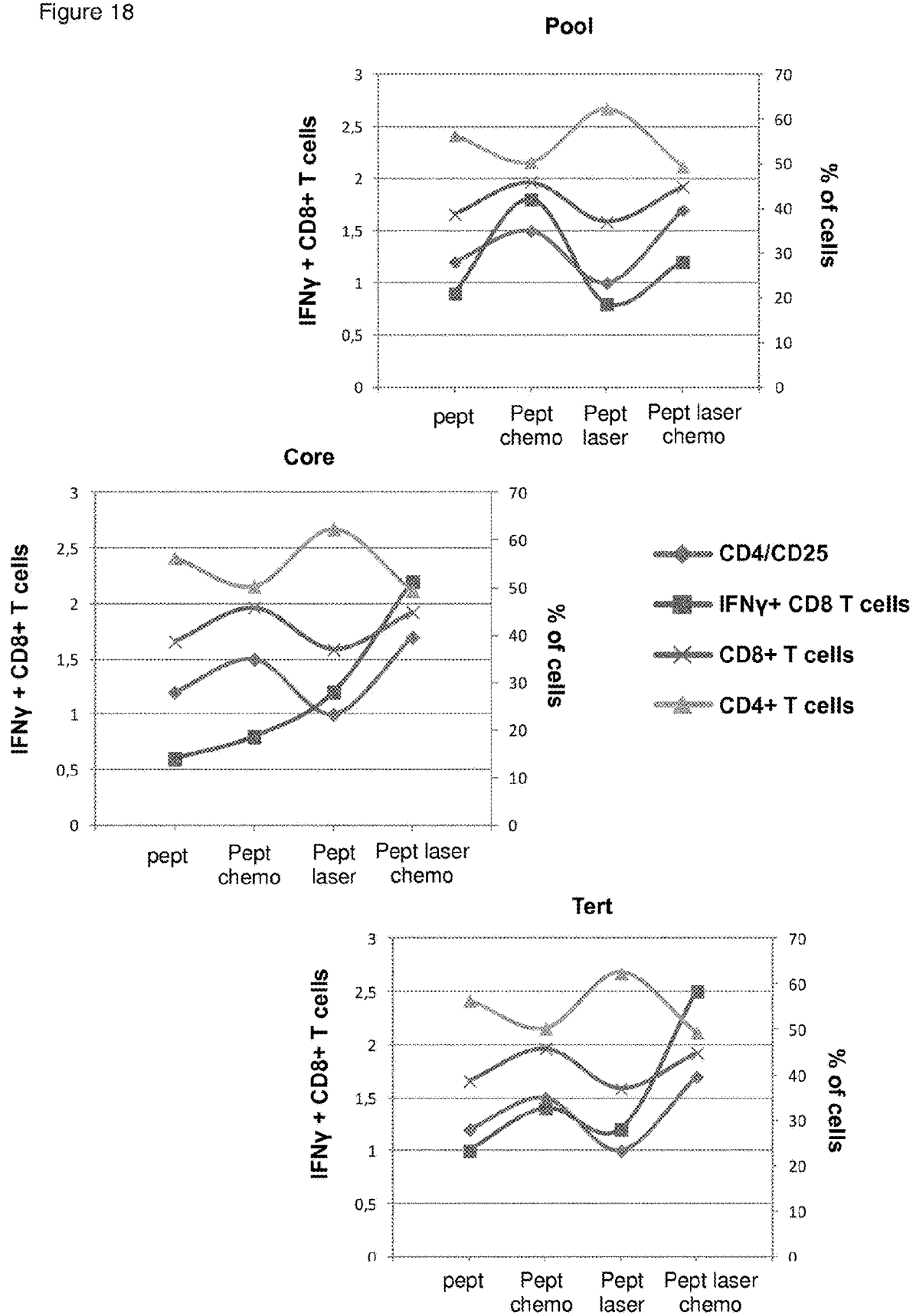

FIG. 18. Correlation between responsiveness to epitopes and cell populations.

DETAILED DESCRIPTION

The term "antigen" as used herein shall refer to a whole molecule or a fragment of such molecule recognized by a subject's immune system, and e.g. presented by an antigen presenting cell (APC). Antigens are substances that can cause the immune system to produce an antibody response against it. Antigens are typically macromolecules or molecules such as proteins, peptides, antibodies, polysaccharides, polynucleotides, RNA, DNA, lipids, glycosylated molecules, carbohydrates, organic or non-organic chemical compounds, naturally occurring modifications of such molecules, aptamers that are foreign to the host. Antigens comprise one or more immunologic epitopes.

"Mixture of antigens" refers to more than one antigen or a plurality of antigens each comprising different epitopes or groups of epitopes.

Specifically, substructures of an antigen, e.g. a polypeptide or carbohydrate structure, generally referred to as epitopes, e.g. B-cell epitopes or T-cell epitope, which are immunologically relevant, may be recognized by the immune system.

The term "ligand" or "binder" as used herein is understood as a natural ligand of a receptor that is located on a surface structure, e.g. on the surface of APCs. A ligand may as well be an artificial molecule which specifically recognizes the receptor. Such ligand may be an artificial derivative of the natural ligand, e.g. a fragment, or else be selected from suitable libraries of binders, e.g. antibody libraries, or libraries of other compounds or scaffolds, e.g. DARPins, HEAT repeat proteins, ARM repeat proteins, tetratricopeptide repeat proteins, and other scaffolds based on naturally occurring repeat proteins, by suitable screening methods to obtain a candidate compound, which is then further characterized for its binding characteristics.

In particular, the binder is a ligand which specifically recognises an APC expressing chemokine (C motif) receptor 1 (XCR1) and/or a C—C chemokine receptor type 7 (CCR7).

The term "the antigen is linked to a binder" with regard to a vaccine preparation refers to covalent or non-covalent coupling or connection or association of an antigen to a binder or ligand, which can be but is not limited to passive adsorption, preferably hydrophobic and/or electrostatic attachment, chemical bonds, fusion, or also bound by electrostatic or affinity binding.

The term "vaccine preparation" refers to a preparation comprising an antigen or a mixture of antigens, wherein at least on of the antigens is linked to a binder of a dermal migratory antigen-presenting cell.

The term "antigen preparation" refers to a preparation comprising an antigen or more than one antigen or a plurality or mixture of antigens.

The term "covalent bond" or "covalent interaction" refers to bonds or interactions created by the sharing of a pair of electrons between atoms. Covalent bonds and interactions include, but are not limited to atom bonds, homopolar bonds, σ-σ-interactions, σ-π-interactions, two-electron-to-center bonds, single bonds, double bonds, triple bonds, as well as combinations of these interactions/bonds. The mentioned interactions or bonds, can be polar or polarized, or non-polar or non-polarized.

"Non-covalent" refers to associations between atoms and molecules such as ionic interactions (e.g., dipole-dipole interactions, ion pairing, and salt formation), hydrogen bonding, non-polar interactions, inclusion complexes, clathration, van der Waals interactions (e.g., pi-pi stacking), and combinations thereof.

The term "passive adsorption", "adsorption" or "absorption" refers to adhesion of atoms, ions or molecules from a gas, liquid or dissolved solid to a surface. The mechanism for adsorption is based primarily on hydrophobic (Van der Waals, London Type) attractions between the hydrophobic portions of the adsorbed molecule and the surface. Most hydrophobic molecules adhere to a surface by passive adsorption. In the case of less hydrophobic molecules (or more hydrophilic surfaces, such as —COOH or $NH_2$ modified surfaces), attachment via both ionic interactions and hydrophobic interactions can take place.

The term "electrostatic interaction" or "electrostatic attachment", as used herein, refers to any interaction occurring between charged components, molecules or ions, due to attractive forces when components of opposite electric charge are attracted to each other. Examples include, but are not limited to: ionic interactions, covalent interactions, interactions between an ion and a dipole (ion and polar molecule), interactions between two dipoles (partial charges of polar molecules), hydrogen bonds and London dispersion bonds (induced dipoles of polarizable molecules).

In some embodiments, the antigen is coupled covalently or non-covalently to the binder. Specifically, the antigen and binder are coupled to each other by passive adsorption, preferably by hydrophobic and/or electrostatic attachment, via antigen spacers or coupled in a way that creates a preferred orientation for the presentation of epitopes presented on the bound antigen.

The antigens can also be connected to the binder using amino acid linker sequences of variable length, specifically of 1, 2, 3, 4, 5, 6, 7, 8, 9, 10, 11, 12, 13, 14, 15, 16, 17, 18, 19, 20, 21, 22, 23, 24, 25 or more amino acids.

The antigens can further be connected to the binder through a hinge region which has the ability to form one, two, or several covalent bonds.

The term "hinge region" refers to a peptide sequence of the homodimeric protein that facilitates the dimerization, such as through the formation of an interchain covalent bond(s), e.g. disulfide bridge(s). The hinge region may be Ig derived, such as hinge exons h1+h4 of an Ig, such as IgG3.

The vaccine or antigen preparation of the invention may contain vaccibodies. Specifically such vaccibodies are described in WO2004076489 or can be derived from www.Vaccibody.com. Vaccibody vaccines consist of three modules, each of them serving a crucial purpose to increase efficacy. They can easily be designed for a given disease based within advanced immunology. The technology is versatile and the vaccines can be delivered as DNA, RNA or protein. The three modules are the antigen-module, dimerization module and targeting module. The dimerization is the hinge/link of the two other modules. The targeting is the ligand or binder to the specific receptor of the specific APC which is to target.

The term "subject" as used herein shall refer to a warm-blooded mammalian, particularly a human being or a non-human animal. In particular the medical use of the invention or the respective method of treatment applies to a subject in need of prophylaxis or treatment of a disease condition associated with a pathogen infection or an immune disorder, including allergy, cancer, or autoimmune disease. The subject may be a patient at risk of a disease condition or suffering from such disease condition, including early stage or late stage disease. The term "patient" includes human and other mammalian subjects that receive either prophylactic or therapeutic treatment. The term "treatment" is thus meant to include both prophylactic and therapeutic treatment.

A subject is e.g. treated for prophylaxis or therapy of *S. aureus* disease conditions. In particular, the subject is treated, which is either at risk of infection or developing such disease or disease recurrence, or a subject that is suffering from such infection and/or disease associated with such infection.

As used herein, the term "permeant", "substance", or "deliverable substance" or any other similar term means any chemical or biological material or compound suitable for delivery through the biological membrane or tissue. It specifically refers to an antigen or a mixture of antigens or the antigens coupled to a binder of a dermal migratory APC of the vaccine preparation and/or adjuvants or carriers therefore which are suitable for delivery through the biological membrane or tissue.

As used herein, a "biological membrane" means a tissue material present within a living organism that separates one area of the organism from another and, in many instances, that separates the organism from its outer environment. Skin and mucous and buccal membranes are thus included. Also, the walls of a cell, organ, tooth, bone, or a blood vessel would be included within this definition.

The term "effective amount" used herein interchangeably with the term "therapeutically effective amount" of an active substance, e.g. a vaccine antigen coupled to binder of a dermal migratory APC or an antigen or a mixture of antigens contained in a pharmaceutical preparation as described herein is a quantity or activity sufficient to, when administered to the subject effect beneficial or desired results, including clinical results, and, as such, an effective amount or synonym thereof depends upon the context in which it is being applied. It also means a sufficient amount of a substance to provide the desired local or systemic effect and performance at a reasonable benefit/risk ratio attending any treatment.

An effective amount is intended to mean that amount of an active substance that is sufficient to treat, prevent or inhibit such diseases or disorder. In the context of disease, therapeutically effective amounts of the active substance or vaccine antigen as described herein are specifically used to treat, modulate, attenuate, reverse, or affect a disease or condition that benefits from priming the immune response.

The amount of the active substance that will correspond to such an effective amount will vary depending on various factors, such as the given active substance, the pharmaceutical formulation, the type of disease or disorder, the identity of the subject or host being treated, and the like, but can nevertheless be routinely determined by one skilled in the art.

As used herein, the term "metronomic therapy" or "metronomic chemotherapy" or "metronomic administration" refers to administration within short intervals without extended rest periods, e.g., daily, and administration of chemotherapeutic agents at doses significantly less than the maximum tolerated dose (MTD).

As used herein, the term "Maximum Tolerated Dose" or "MTD" refers to the highest dose of a drug or treatment that does not cause unacceptable side effects. The maximum tolerated dose is determined in clinical trials by testing increasing doses on different groups of people until the highest dose with acceptable side effects is found. The respective MTD of a chemotherapeutic agent can be determined by the skilled person using standard methods or references and information provided together with the respective chemotherapeutic.

The term "metronomic administration" refers to the continuous administration of low doses of chemotherapy drugs designed to target the endothelial cells lining the blood vessels supplying tumor cells. Metronomic chemotherapy uses conventional cytotoxic drugs but counts on them to stop or slow blood vessel growth. The name metronomic comes from the idea of regular administration of the drug.

The term "low-dose" with regard to metronomic administration refers to a cyclophosphamide dosage of about 5 mg/kg, specifically 4.5 mg/kg, specifically 4 mg/kg, specifically 3.5 mg/kg, specifically 3 mg/kg, specifically 2.5 mg/kg, specifically 2 mg/kg or less; a paclitaxel dosage of about 2.5 mg/kg, specifically 2 mg/kg, specifically 1.5 mg/kg, specifically 1 mg/kg or less; a docetaxel dosage of 0.5 mg/kg, specifically 0.4 mg/kg, specifically 0.3 mg/kg, specifically 0.2 mg/kg, specifically 0.1 mg/kg or less.

The term "high-dose" with regard to metronomic administration refers to a cyclophosphamide dosage of about 10 mg/kg, specifically 10.5 mg/kg, specifically 11 mg/kg, specifically 11.5 mg/kg, specifically 12 mg/kg, specifically 12.5 mg/kg, specifically 13 mg/kg or more; a paclitaxel dosage of about 5 mg/kg, specifically 5.5 mg/kg, specifically 6 mg/kg, specifically 6.5 mg/kg or more; a docetaxel dosage of 1 mg/kg, specifically 1.1 mg/kg, specifically 1.2 mg/kg, specifically 1.3 mg/kg, specifically 1.4 mg/kg, specifically 1.5 mg/kg or more.

For example, metronomic administration of cyclophosphamide at a low dose, e.g., 50 mg/day as compared with representative MTD doses of about 1.3 to 1.5 mg/kg body weight, has shown promising results in a wide range of cancers (N. Penel et al., Critical Reviews in Oncolog Hematology, 2012, 82:40-50).

Specifically, metronomic therapy according to an embodiment of the invention may refer to a daily administration at low, non-toxic doses which are still anti-angiogenic and which may decrease the potential for rebound angiogenesis and enhance the potential for synergism in combination setting with a vaccine preparation to enhance anti-tumor immune responses. Low, i.e. below MTD, metronomic dose concentrations administered at regular intervals without rest periods are immunostimulatory, specifically due to a greater toxicity for suppressor T cells than helper T lymphocytes, and because of the stimulation of NK cells.

As used herein, the term "in combination," in the context of the administration of two or more therapies to a subject, refers to the use of more than one therapy (e.g., more than one vaccine/antigen preparation and/or chemotherapeutic agent). The use of the term "in combination" does not restrict the order in which therapies are administered to a subject. For example, a first therapeutic agent (i.e. antigen preparation and/or chemotherapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapeutic agent, i.e. antigen preparation and/or chemotherapeutic agent) to a subject.

Specifically, the preparation containing an antigen or mixtures of antigens is administered weekly for a period of 1, 2, 3, 4, 5, 6, 7, 8, 9, 10 weeks and the chemotherapeutic agent is administered at a daily interval. Specifically, both administrations are started at the same day, specifically they are started simultaneously.

The invention moreover provides chemotherapeutic agents in combination with pharmaceutical compositions wherein said pharmaceutical compositions comprise an active substance, e.g. a chemical entity or a peptide or protein, e.g. an antigen or immunogen as described herein and a pharmaceutically acceptable carrier or excipient. The chemotherapeutic agent can be administered enterally, i.e. by oral, sublingual or rectal administration.

The term "parenteral" as used herein refers to subcutaneous, intracutaneous, intravenous, intramuscular, intraarticular, intraarterial, intrasynovial, intrasternal, intrathecal, intralesional, intraperitoneal, intratracheal, intracranial, intracoronar, intrapulmonary, e.g. employing inhalable technology or pulmonary delivery systems.

Exemplary chemotherapeutic formulations as used for parenteral administration include those suitable for subcutaneous, intramuscular or intravenous injection as, for example, a sterile solution, emulsion or suspension.

The invention moreover provides pharmaceutical compositions which comprise a drug or an active substance, e.g. a chemical entity or a peptide or protein, e.g. an antibody, or an antigen or immunogen as described herein, specifically an antigen linked to a binder of a dermal migratory APC or a mixture thereof or an antigen or a mixture of antigens, and a pharmaceutically acceptable carrier or excipient. These pharmaceutical compositions can be administered in accordance with the present invention as a short term administration by administering the preparations over a period within 1, 2, 3, 4, or 5 hours, or longer, e.g. over about 24 hours (+/−2 hours). Preferred preparations are emulsions, dispersions or solutions comprising the active substance and the pharmaceutical carriers. Such carriers suitable for facilitating means of administration as described herein are well known in the art.

As used herein, "carriers" refer to carrier materials without significant pharmacological activity at the quantities used that are suitable for administration with other permeants, and include any such materials known in the art, e.g., any liquid, gel, solvent, liquid diluent, solubilizer, microspheres, liposomes, microparticles, lipid complexes, permeation enhancer, or the like, that is sufficiently nontoxic at the quantities employed and does not interact with the substance, which may be an antigen preparation containing an antigen or mixtures of antigens or a vaccine preparation containing an antigen linked to a binder of a dermal migratory APC according to the invention, to be administered in a deleterious manner.

Examples of suitable carriers for use herein include water, saline, phosphate buffered saline, dextrose, buffers, mineral oil, silicone, inorganic or organic gels, aqueous emulsions, glycerol, various alcohols like ethanol, liquid sugars, cyclodextrins, surfactants, lipids, microparticles and nanoparticles, waxes, petroleum jelly, and a variety of other oils, polymeric materials and liposomes as well as combinations of any thereof.

Pharmaceutically acceptable carriers further include any and all suitable solvents, dispersion media, coatings, antibacterial and antifungal agents, isotonic and absorption delaying agents, and the like that are physiologically compatible with an active substance provided by the invention.

In one such aspect, an antigen can be combined with one or more carriers appropriate the topical or intradermal route of administration. An active substance may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, an antigen may be dissolved in saline, water, polyethylene glycol, propylene glycol, carboxymethyl cellulose colloidal solutions, ethanol, corn oil, peanut oil, cotton seed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein an active substance and one or more further therapeutically active agents, e.g. a combination of immune modulators for active and passive immunotherapy, are formulated.

Pharmaceutical compositions are specifically contemplated wherein an antigen or antigen linked to a binder of dermal migratory APC or mixtures of antigens or antigen-binder conjugates and one or more further therapeutically active agents, e.g. a combination of immune modulators for active and passive immunotherapy, are formulated.

Stable formulations of the pharmaceutical preparation are prepared for storage by mixing the active substance having the desired degree of purity with optional pharmaceutically acceptable carriers, excipients or stabilizers, in the form of lyophilized formulations or aqueous solutions. The formulations to be used for in vivo administration are specifically sterile, preferably in the form of a sterile aqueous solution. This is readily accomplished by filtration through sterile filtration membranes or other methods. Therapeutically active agents disclosed herein may also be formulated as immunoliposomes, and/or entrapped in microcapsules.

The term "intradermal" with regard to administration of a substance is herein understood to refer to delivery of the substance to or into the dermis. Intradermal means passage of a permeant into or through the biological membrane or tissue to deliver the permeant to the dermal layer, to therein achieve effective therapeutic tissue levels of a substance, or to store an amount of substance during a certain time in the biological membrane or tissue. The administration is thus into the skin, typically into the dermis and/or the epidermis, but does not include administration into the subcutaneous layer(s) of the skin. In particular, the intradermal administration includes the administration into the dermis and/or the epidermis (intraepidermal), specifically into the basal/germinal layer (stratum basale/germinativum), and/or into the basement membrane, which connects the epidermis to the dermis.

Intradermal delivery of a substance, i.e. antigens or antigens linked to a binder of a dermal migratory APC may be achieved using any mode of delivery in which the composition is supplied to the dermis, but does not pass through the dermis to the muscle, including those where the substance is delivered directly to the dermis, e.g. needleless by a laser technique, and/or by a needle which passes entirely through the epidermis to the dermis, and those where the substance is first delivered into the epidermis by penetration of the epidermis, where the substance then moves through the epidermis (typically about 0.1 mm thick in humans) to the dermis (typically about 0.6-3 mm thick in humans).

Intradermal administration of the pharmaceutical composition may be done by topical administration onto a microporated surface. In particular a predefined area on the skin surface is treated with a laser to generate a plurality of pores.

Specifically, the vaccine or antigen preparation or pharmaceutical preparation as described herein is administered as one single boost vaccination or repeatedly administered. The repeated administration may be within the same priming area or within different priming areas. For example, the repeated administration can be at different locations within the same priming area to boost the immune response. The repeated administration can be at different locations within the two or more priming areas to spread the immune response throughout the body.

In particular, for repeated administration of a vaccine or antigen preparation as described herein, it may be preferred to repeatedly administer the preparation within the same priming area, yet at different locations.

The priming area is typically a predetermined area, wherein the permeation surface over time is determined according to the patient's personal characteristics. In a parallel, serial or repeated administration setting, typically at least one preparation is administered at a first location, and a further preparation (or the same preparation at a different time point) is administered at a different location.

Specifically, the priming area is in close proximity to a target location to regionally deliver the antigen to the target location. The target location may be a site of affection, e.g. a site of a primary tumor or metastasis, or a site of infection or inflammation, or a site of allergic disease condition. On the other hand, the target location may be distant to the site of affection, e.g. where an immune response is intended offsite, so to enhance or stimulate a T cell response with a certain degree of anergy, or absent an anergic phenotype.

Typically, the micropores are formed with a laser porator throughout an area of porated skin thereby producing a plurality of pores extending across a stratum corneum layer into an epidermal layer and into the dermis, the plurality of pores having a predetermined geometry, wherein the area is equal or greater than 1 cm$^2$. According to specific embodiments, the treatment area ranges from 1 to 100 cm$^2$, specifically 1-25 cm$^2$. Vaccines are typically administered to a treatment area of 1-20 cm$^2$, e.g. 2-6 cm$^2$.

The treatment area may be within one (the same) priming (delivery) area or within more than one (different) priming (delivery) areas. For example, the administration is throughout a treatment area at different locations within the same priming or delivery area, or within two or more priming or delivery areas to deliver the active substance.

The microporated surface is typically circular, squarish or rectangular.

Specifically, the number of pores in the area of porated skin is between 10 and 100.000 μm. The pore diameter is typically in the range of 50 μm to 2000 μm, specifically 50 μm to 300 μm.

The number of pores/cm may generally vary between about 1-10, more typically 10-100, or 100-1000, and in rare cases even higher. Similarly, the pattern of pores in the skin may vary as well, and isotropic distribution is generally preferred. However, and especially, where anatomically and/or physiologically advisable, anisotropic distribution is also contemplated. For example, areas of relatively slow drug diffusion (e.g., fibrotic tissue, thick dermis, etc.) may have a higher number of pores, whereas other areas may have less. Similarly, areas with disease focus may concentrate the pores in the focus and reduce the number of pores in the periphery.

Preferably precise pores are produced by any microporation method, e.g. by a needle-free laser or else employing microneedles.

Various techniques can be used for creating pores in biological tissues. Preferably a microporator using a laser beam for creating pores is used. But, for example, also a device for heating via conductive materials or a device generating high voltage electrical pulses can be used for creating pores. U.S. Pat. No. 6,148,232, for example, discloses a technique for creating micro-channels by using an electrical field. This device could also be suitable for creating micropores of predetermined shapes, if provided with additional means to reproducibly create micropores, such as feedback means according to the invention, to detect characteristics of the individual micropores.

The amount of substances delivered through the biological membrane, in particular from the surface of the skin to within the mammal or human body, depends on the permeation surface and its variation over time. The present invention therefore also provides a system for transmembrane administration of a permeant, to provide a permeant like an antigen, a mixture of antigens or the vaccine preparation as described herein, to provide an appropriate initial microporation dataset, and to provide a microporator to create a microporation according to the initial microporation dataset. After the microporation is created, a permeant is applied onto the skin, and the transdermal or intradermal delivery of the permeant takes place in a predetermined way. To apply the permeant effectively, it is important to fit properties of the permeant and the microporation accordingly, to ensure a desired local or systemic effect, for example to ensure a predetermined concentration of a substance in the blood.

As used herein the term "initial microporation" refers to the total number of pores created. "Initial microporation dataset" refers to a set of data, wherein the initial microporation is defined. The dataset including at least one parameter selected from the group consisting of: cross-section, depth, shape, permeation surface, total number of individual pores, geometrical arrangement of the pores on the biological membrane, minimal distance between the pores and total permeation surface of all individual pores. Preferably the initial microporation dataset defines the shape and geometrical arrangement of all individual pores. Preferably the initial microporation dataset defines the shape and geometrical arrangement of all individual pores, which then will be created using the microporator, so that the thereby created initial microporation is exactly defined and can be reproduced on various locations on the biological membrane, also on different objects, subjects or persons.

According to one preferred embodiment, the system allows, for a specific drug, i.e. the antigen or vaccine preparation of the invention, to select an appropriate initial microporation dataset out of a plurality of initial microporation datasets, so that a microporation is created according to the appropriate initial microporation dataset. When the respective drug is applied onto the skin, the transdermal delivery of the drug in function of time is mainly determined by the function of the permeation surface over time. The integrated permeant administering system therefore also allows to individually apply a drug, and for example to reach a predetermined concentration of a drug in the blood according to individual needs. In a preferred embodiment and method, also personalised parameters of the mammal or human are taken into account when choosing or calculating a personalised initial microporation dataset, so the permeant is administered on personalised needs, to for example ensure for an individual person an optimal, personally adapted concentration or level of a drug in the blood.

As used herein, "poration" or "microporation" means the formation of small holes or pores to a desired depth in or through the biological membrane or tissue, such as the skin of a human being or a mammal to lessen the barrier properties of this biological membrane to the passage of permeants or drugs into the body.

The term "individual pore", "micropore" or "pore" as used in the context of the present application refers to a micropore or a pore, in general a pathway extending from the biological membrane formed by the microporation method. The biological membrane, for example being the skin, the individual pore then is extending from the surface of the skin through all or a significant part of the stratum corneum. In the most preferred embodiment the pathway of the individual pore is extending through all the stratum corneum and part of the epidermis but not extending into the dermis, so that no bleeding occurs. In the most preferred embodiment the individual pore has a depth between 10 μm (for newborns 5 μm) and 150 μm.

As used herein "ablation" means the controlled removal of material which may include cells or other components comprising some portion of a biological membrane or tissue. The ablation can be caused, for example, by one of the following:

kinetic energy released when some or all of the vaporizable components of such material have been heated to the point that vaporization occurs and the resulting rapid expansion of volume due to this phase change causes this material, and possibly some adjacent material, to be removed from the ablation site;
thermal or mechanical decomposition of some or all off the tissue at the poration site by creating a plasma at the poration site;
heating via conductive materials;
high voltage AC current;
pulsed high voltage DC current;
micro abrasion using micro particles;
pressurised fluid (air, liquid);
pyrotechnic;
electron beam or ion beam;

The device causing the ablation is herein called the ablator.

As used herein, "tissue" means any component of an organism including but not limited to, cells, biological membranes, bone, collagen, fluids and the like comprising some portion of the organism.

As used herein "puncture" or "micro-puncture" means the use of mechanical, hydraulic, sonic, electromagnetic, or thermal means to perforate wholly or partially a biological membrane such as the skin or mucosal layers of a human being or a mammal.

Micro-punctures or punctures may also be created by using microneedles.

To the extent that "ablation" and "puncture" accomplish the same purpose of poration, i.e. creating a hole or pore in the biological membrane optionally without significant damage to the underlying tissues, these terms may be used interchangeably.

As used herein "puncture surface" means the surface of the hole or pore at the outer surface of the biological membrane, which has been ablated or punctured.

According to a specific aspect, a microfractional laser is used. Specifically, the laser is an ablative laser, e.g. a laser employing controlled fractional ablation.

According to another aspect, a non-ablative laser may be used, e.g. to provide for microchannels.

It is generally preferred that at least some of the pores have a predetermined geometry that is at least in part a function of the substance to be administered, which can be an antigen, a mixture of antigens or the vaccine preparation or pharmaceutical preparation comprising any of the foregoing. Moreover, the predetermined geometry will preferably control the inner pore surface area, the time to pore re-closure, and/or the pore depth (i.e., layer of epidermis or dermis that is contacted with the drug). The drug (or drugs) is then applied to the area of porated skin, which may be done in single, repeated, or continuous (e.g., under occlusion) manner. While numerous alternative wavelengths are deemed suitable, particularly preferred wavelengths for laser ablation is at a wavelength of at least 2500 nm, and most preferably at about 2950 nm; but can go into the far infra-red range such as 10600 nm ($CO_2$).

Specifically, the laser porator is configured to direct a pulsed laser beam onto skin to thereby create the plurality of pores, and wherein the laser porator is further configured to hit at least one of the plurality of pores at least twice.

With respect to suitable laser types and operational parameters, it is generally contemplated that the laser type and operational parameters are selected such that photoablation and/or photodisruption is achieved at little or no irreversible tissue damage, but the depth of pores into the dermis is achieved.

Therefore, preferred wavelengths of lasers used herein will predominantly have a wavelength in which water has a high absorbance and in which structural or functional components of the cell have significantly less or even no absorbance. Thus, contemplated wavelengths typically include mid-infrared and higher wavelengths, and especially preferred wavelengths will be in the range of between about 2500 nm and 5000 nm. Most preferred laser wavelengths are presently contemplated to be at about 3000 nm, and a person of ordinary skill in the art will be readily able to select suitable laser devices (e.g., Er:YAG laser with 2940 nm wavelength or Optical Parametric Oscillators (OPO)). Furthermore, and while not limiting to the inventive subject matter, the wavelength will preferably also be selected such that a minimum thermal destructive effect is achieved when the pulse time is 1 ms or less. Based on previous experiments (data not shown), thermal tissue damage is minimized at a wavelength of about 3000 nm where the pulse time was less than 100 μs, and more typically about 10 μs. A similar minimum was observed at wavelengths between 190 and 300 nm, however, such wavelengths are not suitable due to the high absorption of such radiation in the purine and pyrimidine bases of nucleic acids and aromatic residues of certain amino acids.

With respect to suitable ranges of irradiance, it is generally preferred that the irradiance is at least 104 $W/cm^2$, and more preferably at least 105 $W/cm^2$, even more preferably between 105 $W/cm^2$ and 109 $W/cm^2$, and most preferably between 105 $W/cm^2$ and 1012 $W/cm^2$ where energy doses of between about 0.01 $J/cm^2$ to 1000 $J/cm^2$, and more typically 0.1 $J/cm^2$ to 100 $J/cm^2$ are employed. Consequently, the laser pulse time/tissue exposure time is preferably less than 1 ms, more preferably less than 100 μs, even more preferably between 100 μs and 10 ns, and most preferably between 100 μs and 0.1 μs. Sizing and operation of lasers to achieve such parameters is well understood in the art, and many of the lasers and control systems therefore are commercially available.

With respect to suitable pulse times, and especially where relatively small laser pulse time/tissue exposure times are used, it should be noted that the laser parameters are preferably set such as to still achieve a blow-off effect (i.e. vaporization of tissue to a degree effective to thermally remove vaporized tissue). The person of ordinary skill in the art will readily appreciate that there is a positive correlation between irradiance and blow-off effect and a negative correlation between exposure time and depth of pore formation. Consequently, and particularly where small laser pulse time/tissue exposure times are used, multiple laser pulses onto the same pore, will typically be required to form a micropore rather than to increase irradiance as such increase may also increase incidence of irreversible tissue damage (e.g., carbonization and/or coagulation). Consequently, and viewed from another perspective, it should be recognized that especially suitable operational parameters will be selected to provide a balance between minimum tissue damage and maximum desired effect. Selecting the operational parameters of the laser such that photoablation and/or photodisruption is achieved leads to a micropore with no or neglectable carbonisation and small irreversible tissue. To achieve a small amount of irreversible tissue is very important, because after healing, the tissue should be free of scars, in particular if the tissue, or even the same spot on the tissue, is repeatedly porated during a longer period of time such as some days or weeks.

Most preferably the pulsed beam has a wavelength between 2.65 microns and 3.1 microns, because water has a high absorption coefficient within this range. Most preferably the diameter of the beam is of less than 1 mm, so the needed energy per pulse is just high enough to stay above the ablation threshold of for example 1 Joule per $cm^2$ for human skin. Preferably pulses having a pulse time or temporal width of less than 1 µs are used, more preferably between 50 ns and 150 ns. Such a temporal width reduces the thermal damage of tissue surrounding a micropore to a minimum because of the thermal relaxation time of water and biological tissue at wavelengths at 3 microns is about 1 µs. So heat conduction in the skin is very low and only given by very high pulse repetition rates due to heat accumulation. A temporal width of less than 150 ns further reduces the heating of tissue surrounding a micro pore also at high pulse repetition rates. Thermal relaxation is the process by which heat diffuses through tissue or water by conduction. When the laser exposure is less than the thermal relaxation time there is minimal thermal damage because most of the laser energy is converted into ablation energy. The thermal relaxation time of skin could be around 1 ms depending on the water content, and the thermal relaxation time of water could be around 1 µs. If laser light of such pulse length or longer would be applied to tissue, a high thermal transfer of heat would occur to the surrounding tissue. Because of the short pulses applied, which in a preferred embodiment are below the thermal relaxation time of skin or water, the tissue is less or even not damaged. To create an initial microporation on the biological membrane, the initial microporation preferably comprising between 100 and 10000 individual pores. The pulse repetition frequency of the laser source is preferably higher than 200 Hz, most preferably higher than 1 kHz. This means that the total time to create the entire initial microporation needs preferably less than 10 seconds.

Micropores are typically generated by means of a microporator. An exemplary device for laser-assisted micropore formation which can be used for intradermal delivery is P.L.E.A.S.E.® provided by Pantec Biosolutions AG (Rugell, Liechtenstein). Precise depth of the micropores can trigger the desired immune stimulus which allows effective priming of the immune response, even in the absence of exogenous adjuvants.

According to a specific example, the P.L.E.A.S.E device is used to deliver vaccibodies—under a protein format—within the dermis. It can be demonstrated that it exploits the unique immunostimulatory properties of XCR1$^+$ dermal DCs. Using B16F10 (B16), a highly aggressive metastatic and poorly immunogenic melanoma and its ovalbumin (OVA) expressing variant (B16-OVA), the in vivo antitumor efficacy of laser-assisted, dermal delivery of OVA-containing vaccibodies in prophylactic and therapeutic settings is demonstrated.

In particular, dendritic cells (DCs) expressing the XCR1 chemokine receptor excel in presentation of extracellular antigens to CD8+ T cells. Due to its high content in DCs, including XCR1+ DCs, the skin dermis is an attractive site for vaccine administration. By creating laser-generated micropores through the epidermis, a model protein antigen fused to XCL1– the ligand of XCR1– is targeted to dermal XCR1+ DCs and antigen-specific CD8+ and CD4+ T cell responses are induced. Efficient immunization required the emigration of XCR1+ dermal DCs to draining lymph nodes and occurred irrespective of Toll-like receptors. Moreover, a single intradermal immunization protected mice against melanoma tumor growth in prophylactic and therapeutic settings, in the absence of exogenous adjuvant. The existence of functionally equivalent XCR1+ dermal DCs in human should permit the translation to human cancer immunotherapy of needle-free intradermal delivery of tumor-specific vaccine targeting XCR1+ DCs.

According to a further example, a novel vaccination strategy based on intradermal delivery of antigens to APCs via C-Type lectin receptor targeting is presented.

According to a specific embodiment, the antigen can be coupled to mannan. As a specific example, protein Betv 1 was chemically coupled to mannan from *S. cerevisiae* and used to immunize mice via laser-porated skin. More efficient antigen uptake and enhanced immunogenicity was observed compared to intradermal immunization (using a needle without laser-assistance) or unconjugated protein.

Combination with checkpoint inhibition is herein understood as follows:

The immune system depends on multiple checkpoints or "immunological brakes" to avoid overactivation of the immune system on healthy cells. Tumor cells often take advantage of these checkpoints to escape detection by the immune system. CTLA-4 and PD-1 are checkpoints that have been studied as targets for cancer therapy. CTLA-4 has been shown to be aberrantly upregulated and present on the surface of T cells in certain cancers, dampening T-cell activation in response to tumor cells. PD-1 is another immunologic checkpoint that has been found to be upregulated in certain tumors; it inhibits T-cell function contributing to the tumor's ability to evade the immune system.

Checkpoint blockade has induced significant clinical responses in melanoma and non-small-cell lung cancer but is less successful in other cancers such as pancreatic, colorectal and ovarian cancer. Tumour regression after therapeutic PD1 blockade requires the presence of pre-existing tumour-specific CD8+ T cells. Vaccinations (as shown in Example 1) are perfectly equipped to induce T cell proliferation and to activate T cells, whereas immune checkpoint antibodies are required to re-energize T cells. This combination treatment is more effective due to the IFNγ produced by the incoming vaccine-induced T cells enhancing the expression of immune checkpoint ligands in the microenvironment, the receptors for which are upregulated on activated T cells.

The embodiment of the invention comprises following items:

1. A vaccine preparation comprising an antigen linked to a binder of a dermal migratory antigen-presenting cell (APC) for use in the prophylactic or therapeutic treatment of a subject by intradermal administration through laser-generated micropores.

2. The preparation for use according to item 1, wherein the binder specifically recognizes a surface receptor of an APC.

3. The preparation for use according to item 1 or 2, wherein the binder is a ligand which specifically recognises an APC expressing chemokine (C motif) receptor 1 (XCR1) and/or C—C chemokine receptor type 7 (CCR7).

4. The preparation for use according to item 1 or 2, wherein the ligand specifically recognises an APC expressing a C-type lectin receptor.

5. The preparation for use according to any of items 1 to 4, wherein the antigen is selected from the group consisting of a tumor-associated antigen, a self-antigen, a microbial antigen, an allergen, or an antigen comprising an immunorelevant epitope of any of the foregoing.

6. The preparation for use according to any of items 1 to 4, wherein the antigen is administered in the absence of an exogenous vaccine adjuvant.

7. The preparation for use according to any of items 1 to 6, wherein the antigen is administered in an effective amount to elicit local T-cell response at the draining lymph node, and optionally systemic T-cell response.

8. The preparation for use according to any of items 1 to 7, wherein the preparation is repeatedly administered.

9. The preparation for use according to item 8, wherein the repeated administration is within a priming area, preferably the repeated administration is at different locations.

10. The preparation for use according to item 9, wherein the priming area is in close proximity to a target location to regionally deliver the antigen to the target location.

11. The preparation for use according to any of items 1 to 10, wherein
a) a microporated surface comprising a plurality of micropores is produced at a predetermined permeation surface of the subject's skin by laser poration; and
b) the preparation is topically applied onto the microporated surface.

12. The preparation for use according to item 11, wherein the microporated surface is about two to ten times smaller than a total inner surface of pores created by the laser poration.

13. The preparation for use according to item 11 or 12, wherein the preparation is applied in the form of an antigen-rich solution or emulsion or dispersion, preferably by a patch, gel, cream, adequous solution, powder, tape, or spray.

14. A pharmaceutical preparation comprising an antigen linked to a binder of a dermal migratory APC and an active substance for use in the prophylactic or therapeutic treatment of a subject by intradermal administration through laser-generated micropores, for regional delivery to a target location.

15. The preparation for use according to item 14, wherein the subject is at risk of or suffering from infectious disease or an immune disorder, such as selected from the group consisting of cancer, autoimmune disease or allergy, and the active substance is an immune modulator used in the treatment of such infectious disease or immune disorder.

16. The preparation for use according to item 14 or 15, wherein the active substance is an immune modulator, such as substance priming the immune response which is selected from the group consisting of an antigen, an antibody or antigen-binding fragment thereof, a small molecule, peptide or protein, or combinations of any of the foregoing.

17. The preparation for use according to any of item 14 to 16, wherein the active substance is an immune modulator which is downmodulating the coinhibitory receptor CTLA-4, or the coinhibitory receptor, PD-1, or its ligand, PD-L1.

18. The preparation for use according to any of items 14 to 17, wherein the active substance is an antibody or antigen-binding fragment thereof, for use in passive immunotherapy.

19. The preparation for use according to any of items 14 to 16, wherein the active substance is a vaccine antigen, wherein the antigen is selected from the group consisting of a tumor-associated antigen, a self-antigen, a microbial antigen, an allergen, or an antigen comprising an immunorelevant epitope of any of the foregoing.

20. The preparation for use according to item 19, wherein the antigen is administered in an effective amount to elicit local T-cell response at the draining lymph node, and optionally systemic T-cell response.

21. The preparation for use according to any of items 14 to 20, wherein the preparation is repeatedly administered within a priming area, preferably wherein the repeated administration is at different locations.

22. The preparation for use according to item 21, wherein the priming area is in close proximity to a target location to regionally deliver the antigen to the target location.

23. The preparation for use according to any of items 14 to 22, wherein
a) a microporated surface comprising a plurality of micropores is produced at a predetermined permeation surface of the subject's skin by laser poration; and
b) the preparation is topically applied onto the microporated surface.

24. The preparation for use according to item 23, wherein the microporated surface is about two to ten times smaller than a total inner surface of pores created by the laser poration.

25. The preparation for use according to item 23 or 24, wherein the preparation is applied in the form of an antigen-rich solution or emulsion or dispersion, preferably by a patch, gel, cream, adequous solution, powder, tape, or spray.

26. A combination of an antigen or mixture of antigens and a chemotherapeutic agent for use in the prophylactic or therapeutic treatment of an infectious disease or an immune disorder in a subject, wherein the antigen or mixture of antigens are administered intradermally through laser-generated micropores and the chemotherapeutic agent is administered at a dosage below its maximum tolerated dose (MTD).

27. The combination for use according to item 26, wherein the antigen is selected from the group consisting of a viral antigen, tumor-associated antigen, a self-antigen, a microbial antigen, an allergen, or an antigen comprising an immunorelevant epitope of any of the foregoing or a mixture thereof.

28. The combination for use according to item 26 or 27, wherein the antigen comprises at least one peptide, specifically 2, 3, 4, 5, or more different peptides.

29. The combination for use according to any of items 26 to 28, wherein the antigen is a cancer vaccine antigen preparation.

30. The combination for use according to any one of items 26 to 29, wherein the antigen preparation is a multi-peptide cocktail including at least one viral antigen, specifically selected from the group of HCV antigens, and/or at least one universal tumor antigen, specifically selected from hTERT epitopes.

31. The combination for use according to any of items 26 to 30, wherein the chemotherapeutic agent is a multi-drug cocktail of 2, 3, 4, 5 or more agents.

32. The combination for use according to any one of items 26 to 31, wherein the chemotherapeutic cocktail comprises at least one alkylating agent and/or at least one taxane.

33. The combination for use according to any one of items 26 to 32, wherein the chemotherapeutic composition is administered at repeated doses.

34. The combination for use according to any one of items 26 to 33, wherein the chemotherapeutic agent is administered at metronomic dosing.

35. The combination for use according to any one of items 26 to 34, wherein the antigens are administered in an effective amount to elicit local T-cell response and/or systemic T-cell response.

36. The combination for use according to any one of items 26 to 35, wherein the antigens are administered once or preferably administered repeatedly.

37. The combination for use according to item 36, wherein the repeated administration is within a priming area, preferably at different locations.

38. The combination for use according to any one of items 26 to 37, wherein a) a microporated surface comprising a plurality of micropores is produced at a predetermined permeation surface of the subject's skin by laser poration, b) the antigens are topically applied onto said microporated surface, and c) the chemotherapeutic agent is administered enterally or parenterally, specifically orally, subcutaneously or intravenously.

39. The combination for use according to item 38, wherein the microporated surface is about 2- to 10-times smaller than a total inner surface of pores created by the laser poration.

40. The combination for use according to item 38 or 39, wherein the antigens applied in the form of an antigen-rich solution or emulsion or dispersion, preferably by a patch, gel, cream, aqueous solution, powder, tape, or spray.

41. The combination for use according to any one of items 38 to 40, wherein the antigens are repeatedly administered within a priming area, preferably wherein the repeated administration is at different locations.

42. Kit of parts comprising a) a set of administration units for intradermal administration through laser-generated micropores, each containing an antigen or mixture of antigens, and b) a set of administration units for parenteral administration, each containing a chemotherapeutic agent.

The foregoing description will be more fully understood with reference to the following examples. Such examples are, however, merely representative of methods of practicing one or more embodiments of the present invention and should not be read as limiting the scope of invention.

EXAMPLES

Example 1

Laser-Assisted, Intradermal Delivery of XCL1-Based Vaccibodies Permits the Specific Targeting of XCR1$^+$ Dermal DCs Prior to targeting XCR1$^+$ dermal DCs in situ, we characterized the specificity of vaccibodies on single-cell suspensions prepared by enzymatic digestion and gentle dissociation of ear skin. For that purpose, the antigenic moiety of vaccibodies was replaced by mCherry, a red monomeric fluorescent protein (FIG. 1A), allowing binding specificity to be assessed by flow cytometry. By combining CD24 and CD11b expression, CD45$^+$MHCII$^+$ skin cells can be divided into Langerhans cells (LCs), XCR1$^+$ dermal DCs, and CD11b$^+$CD24$^{low}$ dermal cells (Bachem et al, 2012; Crozat et al, 2011; Tamoutounour et al, 2013). Analysis of CD11b+ CD24low dermal cells for the expression of Ly-6C and CD64 identified CD11b+ DCs on the basis of their Ly-6C− CD64− phenotype (Tamoutounour et al, 2013). The remaining CD11b$^+$CD24$^{low}$ dermal cells include monocytes, monocyte-derived DCs (moDCs) and macrophages (FIG. 1B). XCL1-mCherry vaccibodies specifically stained XCR1$^+$ DCs whereas no staining was observed on cells isolated from the ear of mice deficient in XCR1 (FIG. 10).

To target XCL1-based vaccibodies to XCR1$^+$ dermal DCs in a needle-free manner, we used the P.L.E.A.S.E device. Application on the mouse ear skin at a regimen of 75 µs pulse duration with 2 pulses per pore and an energy of 11.9 J/cm$^2$ resulted in the formation of an array of micropores via laser ablation (FIG. 2A). Histological analysis of ear sections indicated that the stratum corneum and the epidermis were removed while the integrity of the dermis was preserved (FIG. 2B). Therefore, the set up chosen created pores which depth was compatible for topically applied XCL1-based vaccibodies to reach the dermis. Analysis of single-cell suspension prepared from ear skin 24 h after laser-assisted delivery of XCL1-mCherry vaccibodies showed that approximately 15% of XCR1$^+$ dermal DCs were stained and using Xcr1$^{-/-}$ mice this staining was shown to depend on XCR1 expression (FIG. 2C). 24 hours after laser application, analysis of the ear skin showed a mild inflammation involving neutrophils and monocytes. Therefore, combining laser microporation and XCL1-based vaccibodies permits to target XCR1$^+$ dermal DCs in a specific and needle-free manner.

XCL1-OVA Vaccibodies are on a Per Molecule Basis More Effective at Eliciting T Cell Responses than Free OVA To test whether targeting XCR1$^+$ dermal DCs with antigen-loaded XCL1-based vaccibodies induced the activation of antigen-specific T cells in vivo, the model antigen OVA was inserted into XCL1-based vaccibodies. Mice were adoptively transferred with CellTraceViolet (CTV)-labeled, OT-I CD8$^+$ T cells, which express a T cell receptor (TCR) specific for SIINFEKL, an ovalbumin (OVA) peptide presented by H-2K$^b$, and OT-II CD4$^+$ T cells, which express a TCR specific for an OVA peptide presented by H2-A$^b$. One day later, the ear of the mice were subjected to laser-assisted microporation and topical application of XCL1-OVA vaccibodies. To compare the potency of the XCL1-OVA formulation with that of free OVA, mice were also treated with concentrations of OVA equimolar to that present in XCL1-OVA vaccibodies. Three days after immunisation, single-cell suspensions were prepared from ear-draining auricular lymph nodes (LNs) and the extent of OT-I and OT-II cell proliferation was determined by CTV dilution (FIG. 3A). XCL1-OVA vaccibodies triggered a higher proliferation of OT-I and OT-II cells than free OVA (FIG. 3 B). Quantification of the data confirmed that XCL1-OVA vaccibodies were on a per molecule basis 15 times more effective at eliciting CD8$^+$ T cell proliferation and 3 times more effective at eliciting CD4$^+$ T cell proliferation than free OVA (FIG. 3C). When the same experiments were repeated with Xcr1$^{-/-}$ mice, the beneficial effect observed following XCL1-OVA treatment was lost, the magnitude of proliferation observed with XCL1-OVA being comparable to that of OVA (FIG. 3 C).

The XCL1 chemokine present in XCL1-OVA vaccibodies has been shown to retain its chemotactic function (Fossum et al, 2014). Therefore, the higher potency noted for XCL1-

OVA antibodies as compared to OVA may not result from the targeting of OVA to XCR1+ DCs but from the ability of XCL1 to promote encounter between XCR1+ DCs and T cells (Crozat et al, 2010; Dorner et al, 2009). However, coadministration of OVA and XCL1 in free forms and in amounts similar to those used in XCL1-OVA treatment resulted in levels of T cell proliferation similar to those elicited by OVA alone (FIG. 3 C). Therefore, the physical linkage between OVA and XCL1 provided by the vaccibody format was essential to maximize the potential of XCR1$^+$ dermal DCs and it is likely that XCR1 merely functioned as an address.

T Cell Responses Elicited by Laser-Assisted Inradermal Delivery of XCL1-OVA Vaccibodies Require Migratory XCR1$^+$ DCs and Occur in a MyD88-Trif Independent Manner Skin DCs capture incoming antigens and after 16 hours to 5 days depending on the DC subset, migrate to skin draining LNs to elicit T cell responses (Itano et al, 2003; Kissenpfennig et al, 2005; Shklovskaya et al, 2008). However, soluble and particulate antigens penetrating the skin can reach the LN subcapsulary sinus in a free form. In case they are too large to enter the relatively restrictive LN conduit network, such lymph borne antigens can be captured by DCs that line the subcapsulary sinus (Gerner et al, 2015). This led to an earlier generation of effector T cell responses, independent of skin-derived migratory DCs. DC-free drainage of skin-delivered antigens is amplified during needle-based, intradermal and subcutaneous immunization due to the excessive interstitial hydrostatic pressure created by fluid injection (Bachmann & Jennings, 2010). To evaluate whether T cell responses elicited by laser-assisted, intradermal delivery of XCL1-OVA vaccibodies required the migration of skin-derived XCR1$^+$ DCs rather than the capture of XCL1-OVA vaccibodies by the XCR1+ DCs that permanently reside in LNs (Dalod et al, 2014), we used Ccr7$^{-/-}$ mice in which the CCR7-dependent migration of DCs from the skin to the draining LNs is impaired (Forster et al, 1999). Analysis of T cell responses of wild-type and Ccr7$^{-/-}$ mice 3 days after immunization showed that OT-I and OT-II responses were 10 to 20 fold reduced, in the absence of CCR7 (Fig E2 A and B). Therefore, CD4$^+$ and CD8$^+$ T cell activation induced by laser-assisted intradermal delivery of XCL1-OVA vaccibodies is primarily due to migration of OVA-presenting XCR1$^+$ dermal DCs to draining LNs rather than to the capture of XCL1-OVA vaccibodies by the resident XCR1$^+$ DCs the precursors of which reach skin draining LNs via the blood. Consistent with the view that no free XCL1-OVA vaccibodies used the lymph or the blood to diffuse away following laser-assisted intradermal delivery in the ear, adoptively transferred OT-I and OT-II T cells present in the spleen and in LNs that drain territories distinct from the ear showed no sign of proliferation (Figure E3 A and B).

Although XCL1-OVA vaccibodies were affinity purified and reconstituted in endotoxin-free PBS prior to delivery, we determined whether the extensive proliferation of antigen-specific T-cells observed after targeting XCR1$^+$ dermal DCs with XCL1-OVA vaccibodies persisted in Myd88$^{-/-}$ Trif$^{-/-}$ double deficient mice that are deprived of two adaptors used in the signal-transduction networks of all Toll Like Receptors (TLR). Laser-assisted, intradermal delivery of XCL1-OVA vaccibodies in Myd88$^{-/-}$ Trif$^{-/-}$ double deficient resulted in levels of OT-I and OT-II T cell proliferation similar to those elicited in wild-type mice (Fig E4 A and B). Therefore, T cell responses triggered by laser-assisted intradermal delivery of XCL1-OVA vaccibodies require migratory XCR1$^+$ DCs and occur irrespective of TLR signals.

Intradermal Delivery of XCL1-OVA Vaccibodies Protects Mice Against Melanoma Tumor Growth in Prophylactic and Therapeutic Settings The B16-OVA melanoma is not rejected by immune-competent syngeneic B6 mice, unless mice have been subjected to prophylactic or therapeutic immunization. To evaluate the capacity of laser-assisted, intradermal delivery of XCL1-OVA vaccibodies to inhibit the growth of B16-OVA tumors, B6 mice were subcutaneously inoculated in the flank with B16-OVA cells (FIG. 4A). Three days later, the ear of the mice was subjected to laser-assisted, dermal delivery of XCL1-OVA vaccibodies and tumor growth was monitored 16 days after inoculation. For the sake of comparison, mice received equimolar amounts of free OVA or PBS. Intradermal vaccination with two different doses of XCL1-OVA vaccibodies significantly suppressed tumor growth as compared to the OVA and PBS groups, and tumor growth was further reduced with the high dose of XCL1-OVA vaccibodies (FIG. 4B). To investigate the prophylactic effects on tumor growth of laser-assisted intradermal XCL1-OVA immunization, B6 mice were immunized with XCL1-OVA vaccibodies and subcutaneously inoculated with B16-OVA tumor cells 30 days later (FIG. 4C). Monitoring tumor growth 14 days after tumor inoculation showed that XCL1-OVA vaccibodies significantly slowed down tumor growth as compared to OVA and PBS (FIG. 4 D). In contrast, mice immunized with XCL1-OVA vaccibodies were not able to control the growth of B16 melanoma (FIG. 5A), and the capacity of XCL1-OVA vaccibodies to inhibit B16-OVA tumor growth was dependent on the expression of XCR1 (FIG. 5B).

To assess whether the reduction in melanoma tumor growth observed upon treatment with XCL1-OVA vaccibodies was associated with the induction of endogeneous, antigen-specific CD8$^+$ T cells, wild-type and Xcr1$^{-/-}$ mice were immunized via laser-assisted intradermal delivery of XCL1-OVA vaccibodies. Six days after immunization, the magnitude of OVA-specific T cell cytotoxicity was measured using an in vivo cytotoxic assay (FIG. 5 C). XCL1-OVA vaccibodies induced a significant T cell cytotoxicity as compared to PBS treated mice and the absence of detectable lysis in Xcr1$^{-/-}$ mice indicated that such T cell cytotoxicity was dependent on the expression of XCR1. Moreover, analysis of the CD8$^+$ and CD4$^+$ T cells that infiltrated B16-OVA tumor mass of mice treated with XCL1-OVA antibodies showed that they were capable of producing interferon (IFN) gamma. In contrast, OVA treatment did not induce IFN□$^+$ T cells over PBS control, a finding consistent with the observation that OVA treatment was unable to slow down tumor growth (FIG. 4). Moreover, staining of the CD8$^+$ T cells that infiltrated the regressing B16-OVA tumor mass with H-2 K$^b$ tetramers loaded with the OVA-derived, SIINFEKL peptide showed that they are largely OVA-specific as well as IFNgamma$^+$ producing (Fig E5). Therefore, laser-assisted, intradermal delivery of XCL1-OVA vaccibodies induced anti-tumoral responses that can be correlated with the presence of OVA-specific IFNgamma$^+$ T cells in the regressing tumor mass.

Discussion

In the present study, we show that by creating laser-generated micropores in the stratum corneum and epidermis, it is possible to target XCL1-OVA vaccibodies to dermal XCR1$^+$ DCs and to induce antigen-specific CD8$^+$ and CD4$^+$ effector T cells. This process required emigration of XCR1$^+$ DCs to draining lymph nodes and occurred irrespective of TLR signals. Moreover, a single intradermal immunization with XCL1-OVA vaccibodies protected mice against melanoma tumor growth in both prophylactic and therapeutic, adjuvant-free settings. Whether antigen targeting to DC results in tolerance or immunity depends on parameters such as the immunogenicty of the targeting antibody (Li et al, 2014) and the co-administration of adjuvants (Kastenmuller et al, 2014; Kreutz et al, 2013). Adjuvants are intended to trigger the pattern-recognition receptors that are expressed by the targeted DCs and that are normally used to detect invading microorganisms or endogenous "danger" signals. In contrast to other studies that targeted XCR1+ DCs via needle-based, intravenous or cutaneous injection (Flacher et al, 2014; Hartung et al, 2015; Joffre et al, 2010), we achieved antigen-specific protection against the B16-OVA melanoma in the absence of adjuvant. Moreover, TLR signals were dispensable for the antigen-specific T cell responses resulting from laser-assisted intradermal delivery of XCL1-OVA vaccibodies. The mode of antigen delivery itself that is skin laser microporation likely explains such a marked difference in adjuvant requirement. The fractional Er:YAG laser operating in the P.L.E.A.S.E device creates micro-coagulated areas in the skin that include dying cells (Scheiblhofer et al, 2013). STING (stimulator of interferon genes) is a protein that resides in the endoplasmic reticulum (ER) of many cells including DCs. It cooperates with the nucleotidyltransferase cGAS to trigger the production of type I IFNs in response to the presence of pathogen- or self-derived DNA in the cytosol. It has been recently shown that XCR1+ DCs contribute to trigger T cell responses against tumors in a STING-dependent manner (Broz et al, 2014; Klarquist et al, 2014; Woo et al, 2014). XCR1+ DCs use STING to sense the self DNA that is released by dying tumor cells (Deng et al, 2014), and, as a result produce type I IFN that contribute to boost their antigen-presenting function and T cell costimulatory properties. Therefore, it is likely that in our model, the death of keratinocytes resulting from P.L.E.A.S.E. application constitutes a STING-dependent adjuvant. Although, the lower laser energy that disseminates in the skin below the micro-coagulated areas does not result in cell death, it disrupts the dermal tissue architecture and increases the motility, migration and entry of DCs into lymphatic vessels (Chen et al, 2013; Chen et al, 2012). We also noted that laser microporation triggers a rapid infiltration of the treated skin with granulocytes and monocytes. Therefore, altogether the adventitious phenomena resulting from laser microporation itself create an inflammatory milieu that likely accounts for the development of immune responses in the absence of exogenous adjuvants. In a mouse model, a rat anti-CLEC9A antibody used to deliver OVA to XCR1+ DCs induced CD4+ T cell and humoral responses against OVA in the absence of adjuvant (Li et al, 2014), a property resulting from the presence of helper epitopes on the rat antibody that were recognized as foreign by the mouse immune system. Along that line, it remains to be determined whether the dimerization unit that is present in vaccibodies and made of human IgG3 domains contribute to enhance immune responses against the antigenic cargo. Finally, considering that the use of adjuvants in vaccines is often associated with safety issues, the possibility to protect against melanoma tumor growth independently of the administration of exogenous adjuvants should facilitate vaccine production.

Migratory DCs originating from tissues such as the skin and the intestine are thought to "instruct" antigen-specific naive T cells in a way that confer them a propensity to home to the tissue from which the migratory DCs originated (Agace, 2006). Such tropism allows primed T cells to exert their effector functions in the tissue subjected to the antigen challenge. When injected intravenously, antigen-conjugated anti-CLEC9A antibodies target the XCR1+ DCs that permanently reside in the spleen and thereby initiate T cell responses in this organ (Joffre et al, 2010). In contrast, following laser-assisted, intradermal delivery of XCL1-OVA vaccibodies, the onset of T cell responses depended on the emigration of XCR1+ dermal DCs and remained limited to the draining LNs. Whether the homing properties imparted on T cells by skin-derived XCR1+ DCs confer them a skin-tropism superior to that elicited by spleen-resident XCR1+ DCs constitutes an important issue when treating conditions such as cutaneous melanoma that remains to be documented. Although the T cell priming resulting from laser-assisted, intradermal delivery of XCL1-OVA vaccibodies is limited to the LN draining the treated skin territory, a systemic T cell response ensued, capable of protecting against cutaneous melanoma developing at a site distant from the one used for immunization. When translated to the humans, this approach should limit the systemic side effects resulting from administration of intravenous vaccines while achieving systemic protective immunity.

In conclusion, using laser-assisted intradermal delivery and a model antigen fused to the XCL1 chemokine, we showed that it is possible to target dermal XCR1+ DCs and harness their cross-presentation capacity. Whereas the efficiency of many vaccines rely on multiple rounds of administration in the presence of adjuvants, we showed that a single intradermal immunization with XCL1-based vaccibodies sufficed to protect mice against melanoma tumor growth in the absence of exogenous adjuvants. Therefore, topic, needle-free intradermal delivery of antigens targeting XCR1+ DCs constitutes a promising way for the development of intradermal vaccines. In the humans, XCR1 expression also defines a DC subset that showed similar anatomical distribution and is endowed with cross-presentation capacity (Bachem et al, 2010; Crozat et al, 2010; Jongbloed et al, 2010; Schlitzer et al, 2013), a feature which should facilitate the translation of the present mouse model to human settings.

Materials and Methods

Mice

Mice were housed under specific pathogen-free conditions and handled in accordance with French and European directives. OT-I (Hogquist et al, 1994), OT-II (Barnden et al, 1998), Ccr7$^{-/-}$ (Forster et al, 1999), Myd88$^{-/-}$Trif$^{Lps2/Lps2}$ deficient in both MyD88 and Trif (Ticam1) and called Myd88$^{-/-}$Trif$^{-/-}$ here (Guilliams et al, 2010), and Xcr1$^{tm1Dgen}$ mice (Xcr1-βGal, called Xcr1$^{-/-}$ mice here) (Crozat et al, 2011) were previously described. C57BL/6J (B6) mice were purchased from Janvier (France).

Isolation of Skin DCs, Monocytes and Macrophages

To extract skin myeloid cells, ears were splitted into dorsal and ventral parts and incubated with a solution of PBS containing 1 mg/mL dispase (Roche) for 2 h at 37° C. or overnight at 4° C. The dorsal and ventral parts were then cut into small pieces and incubated for 90 min at 37° C. with RPMI containing 1 mg/mL DNase and 1 mg/mL Collagenase IV (Worthington Biochemical). The resulting single cell suspension was subjected to centrifugation on a Percoll gradient (Amersham-Pharmacia).

Characterization of Skin Myeloid Cells

Myeloid cells from the skin were characterized by flow cytometry as previously described (Tamoutounour et al, 2013). Briefly, single-cell suspensions were prepared by enzymatic digestion and gentle dissociation of ear skin. After excluding dead cells (Sytox+), T cells (CD3+), NK cells (CD161c$^+$), B cells (CD19$^+$), and neutrophils (Ly-6G$^+$ CD11b$^+$), the remaining CD45$^+$MHCII$^+$ cells can be further divided into LCs (CD11b$^+$CD24$^+$), CD11b$^-$CD24$^+$ dermal DCs, and CD11b$^+$CD24$^{low}$ dermal cells. Analysis of CD11b$^+$CD24$^{low}$ dermal cells for the expression of Ly-6C and CD64 permits to identify CD11b$^+$ DCs on the basis of their Ly-6C$^-$CD64$^-$ phenotype. The remaining CD11b$^+$ CD24$^{low}$ dermal cells include monocyte-derived DCs (MoDCs) and macrophages.

Flow Cytometry

Cells were stained and analyzed using a FACS LSRII system with a DIVA software (BD Biosciences). Cell viability was evaluated using Sytox (Invitrogen) according to the manufacturer's protocol. Anti-NK1.1 (PK136), anti-CD3 (17A2), anti-Ly-6G (1A8), anti-CD19 (6D5), anti-CD64 (X54-5/7.1) were from Biolegend. Anti-CD11c (N418), anti-MHC Class II (I-A/I-E) (M5/114.15.2), anti-CD45.2 (104), anti-CD45.1 (A20), anti-CD24 (M1/69), and anti-CD5 (53-7.3) were from eBioscience. Anti-Ly-6C (AL21), anti-CD4 (RM4-5), and anti-CD8a (53-6.7) were from BD Pharmingen. Prior to analyzing monocytes, MFs and DCs, B cells, T cells, NK cells, and neutrophils were systematically gated out using a "dump-channel" corresponding to cells positive for B220, CD3, NK1.1, or Ly-6G cells. Analysis was performed using FlowJo software (Tree Star, Inc.).

Generation of Vaccibodies

XCL1-based vaccibodies comprising either the mCherry reporter or the ovalbumin (OVA) antigen have been generated and purified as described (Fossum et al, 2014).

Laser-Assisted Skin Microporation and Vaccibodies and Antigen Application on the Skin A P.L.E.A.S.E. portable laser developed by Pantec Biosolutions AG (Bach et al, 2012) was used with the following setting: fluence: 11.9 J/cm$^2$, pulse duration: 75 μs; RepRate: 200 Hz; pulses per pore: 2, pore array size: 14 mm$^2$ and pore density 8%. P.L.E.A.S.E.-assisted skin microporation was performed on the ear of anesthetized mice. 20 μl of sterile PBS, 20 μl of sterile PBS containing 1.5 μg (low) or 3.1 μg (high) OVA, or 20 μl of sterile PBS containing 2.5 μg (low) or 5 μg (high) XCL1-OVA were then evenly applied on the microporated ear surface. The PBS solution percolated inside the micropores in less than 10 minutes.

Histology

For histological analysis, ears were harvested after laserporation and embedded in parafin. Sections (5 μm) were stained with hematoxylin and eosin for microscopical examination.

Preparation of Cell Trace Violet-Labeled T Cells

OT-I and OT-II T cells were isolated from pooled LNs and spleen of OT-I or OT-II mice kept on a Rag-2$^{-/-}$-B6 [CD45.1] background using CD8$^+$ and CD4$^+$ T cell negative isolation kits (Dynal, Invitrogen), respectively. Purity was determined by staining with CD4, CD8, CD5 and TCR Vα2. For CTV labeling, purified OT-I and OT-II T cells were resuspended in PBS containing 2.5 mM cell trace violet (CTV) (Molecular Probes) for 3 min at room temperature. 10$^6$ CTV-labeled OT-I and OT-II T cells were adoptively transferred into the specified mice. At the indicated times, single-cell suspensions were prepared from the auricular LNs draining the immunized ears and OT-I and OT-II T cells were analyzed by FACS.

In Vivo Cytotoxicity Assay

Splenocytes from B6 mice were pulsed with the SIINFEKL peptide or left untreated and labeled with low (0.25 mM) or high (2.5 mM) dose of CTV, respectively. 10$^7$ splenocytes of each preparation were adoptively transferred into mice that have been immunized for 6 days. 36 h later, single-cell suspension were prepared from spleen and the ratio of CTV$^{high}$ to CTV$^{low}$ cells was determined by FACS.

Tumor Model

Mice were injected subcutaneously (s.c.) into the flank with 10$^5$ B16-OVA or B16 melanoma cells (Brown et al, 2001). Tumor size was assessed 14 to 16 days later using a caliper. The presence of T cells infiltrating the tumor was assessed after enzymatic treatment of tumor mass with collagenase 2 (Worthington) and Percoll gradient (Amersham-Pharmacia).

Intracellular Staining

T cells harvested from the tumor mass were incubated for 6 h at 37° C. in the presence of PMA (5 ng/mL) and ionomycin (250 ng/mL). Monensin (Golgistop; BD Pharmingen) was added to the suspension for the last 5 h. Cells were stained with anti-CD5, anti-CD4, anti-CD8 and H-2 K$^b$ tetramers loaded with the SIINFEKL peptide (iTAg MHC tetramers; Beckman Coulter) and then permeabilized using the Cytofix-Cytoperm kit (BD Biosciences). Intracellular cytokines were detected by staining with anti-IFNγ (XMG1.2; BD Pharmingen).

Statistical Analysis

Mann Whitney test was used to assess the statistical significance within the different immunization settings. Probability values are expressed as the following: *, $p<0.001$; , $p<0.01$; *, $p<0.05$ and NS for non significant.

REFERENCES

Agace W W (2006) Tissue-tropic effector T cells: generation and targeting opportunities. Nat Rev Immunol 6: 682-692

Ahrens S, Zelenay S, Sancho D, Hanc P, Kjaer S, Feest C, Fletcher G, Durkin C, Postigo A, Skehel M et al (2012) F-actin is an evolutionarily conserved damage-associated molecular pattern recognized by DNGR-1, a receptor for dead cells. Immunity 36: 635-645

Bach D, Weiss R, Hessenberger M, Kitzmueller S, Weinberger E E, Krautgartner W D, Hauser-Kronberger C, Boehler C, Thalhamer J, Scheiblhofer S (2012) Transcutaneous immunotherapy via laser-generated micropores efficiently alleviates allergic asthma in Phl p 5-sensitized mice. Allergy 67: 1365-1374

Bachem A, Guttler S, Hartung E, Ebstein F, Schaefer M, Tannert A, Salama A, Movassaghi K, Opitz C, Mages H W et al (2010) Superior antigen cross-presentation and XCR1 expression define human CD11c+CD141+ cells as homologues of mouse CD8+ dendritic cells. J Exp Med 207: 1273-1281

Bachem A, Hartung E, Guttler S, Mora A, Zhou X, Hegemann A, Plantinga M, Mazzini E, Stoitzner P, Gurka S et al (2012) Expression of XCR1 Characterizes the Batf3-Dependent Lineage of Dendritic Cells Capable of Antigen Cross-Presentation. Front Immunol 3: 214

Bachmann M F, Jennings G T (2010) Vaccine delivery: a matter of size, geometry, kinetics and molecular patterns. Nat Rev Immunol 10: 787-796

Bachy V, Hervouet C, Becker P D, Chorro L, Carlin L M, Herath S, Papagatsias T, Barbaroux J B, Oh S J, Benlahrech A et al (2013) Langerin negative dendritic cells promote potent CD8+ T-cell priming by skin delivery of live adenovirus vaccine microneedle arrays. Proc Natl Acad Sci USA 110: 3041-3046

Barnden M J, Allison J, Heath W R, Carbone F R (1998) Defective TCR expression in transgenic mice constructed using cDNA-based alpha- and beta-chain genes under the control of heterologous regulatory elements. Immunol Cell Biol 76: 34-40

Bedoui S, Whitney P G, Waithman J, Eidsmo L, Wakim L, Caminschi I, Allan R S, Wojtasiak M, Shortman K, Carbone F R et al (2009) Cross-presentation of viral and self antigens by skin-derived CD103+ dendritic cells. Nat Immunol 10: 488-495

Brown D M, Fisher T L, Wei C, Frelinger J G, Lord E M (2001) Tumours can act as adjuvants for humoral immunity. Immunology 102: 486-497

Broz M L, Binnewies M, Boldajipour B, Nelson A E, Pollack J L, Erle D J, Barczak A, Rosenblum M D, Daud A, Barber D L et al (2014) Dissecting the tumor myeloid compartment reveals rare activating antigen-presenting cells critical for T cell immunity. Cancer Cell 26: 638-652

Caminschi I, Proietto A I, Ahmet F, Kitsoulis S, Shin Teh J, Lo J C, Rizzitelli A, Wu L, Vremec D, van Dommelen S L et al (2008) The dendritic cell subtype-restricted C-type lectin Clec9A is a target for vaccine enhancement. Blood 112: 3264-3273

Chen X, Wang J, Shah D, Wu M X (2013) An update on the use of laser technology in skin vaccination. Expert Rev Vaccines 12: 1313-1323

Chen X, Zeng Q, Wu M X (2012) Improved efficacy of dendritic cell-based immunotherapy by cutaneous laser illumination. Clin Cancer Res 18: 2240-2249

Crozat K, Guiton R, Contreras V, Feuillet V, Dutertre C A, Ventre E, Vu Manh T P, Baranek T, Storset A K, Marvel J et al (2010) The X C chemokine receptor 1 is a conserved selective marker of mammalian cells homologous to mouse CD8alpha+ dendritic cells. J Exp Med 207: 1283-1292

Crozat K, Tamoutounour S, Vu Manh T P, Fossum E, Luche H, Ardouin L, Guilliams M, Azukizawa H, Bogen B, Malissen B et al (2011) Cutting edge: expression of XCR1 defines mouse lymphoid-tissue resident and migratory dendritic cells of the CD8alpha+ type. J Immunol 187: 4411-4415

Dalod M, Chelbi R, Malissen B, Lawrence T (2014) Dendritic cell maturation: functional specialization through signaling specificity and transcriptional programming. Embo J 33: 1104-1116

Deng L, Liang H, Xu M, Yang X, Burnette B, Arina A, Li X D, Mauceri H, Beckett M, Darga T et al (2014) STING-Dependent Cytosolic DNA Sensing Promotes Radiation-Induced Type I Interferon-Dependent Antitumor Immunity in Immunogenic Tumors. Immunity 41: 843-852

Dhodapkar M V, Sznol M, Zhao B, Wang D, Carvajal R D, Keohan M L, Chuang E, Sanborn R E, Lutzky J, Powderly J et al (2014) Induction of antigen-specific immunity with a vaccine targeting NY-ESO-1 to the dendritic cell receptor DEC-205. Sci Transl Med 6: 232ra251

Dorner B G, Dorner M B, Zhou X, Opitz C, Mora A, Guttler S, Hutloff A, Mages H W, Ranke K, Schaefer M et al (2009) Selective expression of the chemokine receptor XCR1 on cross-presenting dendritic cells determines cooperation with CD8+ T cells. Immunity 31: 823-833

Flacher V, Tripp C H, Mairhofer D G, Steinman R M, Stoitzner P, Idoyaga J, Romani N (2014) Murine Langerin+ dermal dendritic cells prime CD8+ T cells while Langerhans cells induce cross-tolerance. EMBO Mol Med 6: 1191-1204

Forster R, Schubel A, Breitfeld D, Kremmer E, Renner-Muller I, Wolf E, Lipp M (1999) CCR7 coordinates the primary immune response by establishing functional microenvironments in secondary lymphoid organs. Cell 99: 23-33

Fossum E, Grodeland G, Terhorst D, Tveita A A, Vikse E, Mjaaland S, Henri S, Malissen B, Bogen B (2014) Vaccine molecules targeting Xcr1 on cross-presenting DCs induce protective CD8 T-cell responses against influenza virus. Eur J Immunol Gerner M Y, Torabi-Parizi P, Germain R N (2015) Strategically localized dendritic cells promote rapid T cell responses to lymph-borne particulate antigens. Immunity 42: 172-185

Gregorio J, Meller S, Conrad C, Di Nardo A, Homey B, Lauerma A, Arai N, Gallo R L, Digiovanni J, Gilliet M (2010) Plasmacytoid dendritic cells sense skin injury and promote wound healing through type I interferons. J Exp Med 207: 2921-2930

Guilliams M, Crozat K, Henri S, Tamoutounour S, Grenot P, Devilard E, de Bovis B, Alexopoulou L, Dalod M, Malissen B (2010) Skin-draining lymph nodes contain dermis-derived CD103(−) dendritic cells that constitutively produce retinoic acid and induce Foxp3(+) regulatory T cells. Blood 115: 1958-1968

Haniffa M, Collin M, Ginhoux F (2013) Ontogeny and functional specialization of dendritic cells in human and mouse. Adv Immunol 120: 1-49

Hartung E, Becker M, Bachem A, Reeg N, Jakel A, Hutloff A, Weber H, Weise C, Giesecke C, Henn V et al (2015) Induction of Potent CD8 T Cell Cytotoxicity by Specific Targeting of Antigen to Cross-Presenting Dendritic Cells In Vivo via Murine or Human XCR1. J Immunol 194: 1069-1079

Henri S, Poulin L F, Tamoutounour S, Ardouin L, Guilliams M, de Bovis B, Devilard E, Viret C, Azukizawa H, Kissenpfennig A et al (2010) CD207+ CD103+ dermal dendritic cells cross-present keratinocyte-derived antigens irrespective of the presence of Langerhans cells. J Exp Med 207: 189-206

Hogquist K A, Jameson S C, Heath W R, Howard J L, Bevan M J, Carbone F R (1994) T cell receptor antagonist peptides induce positive selection. Cell 76: 17-27

Itano A A, McSorley S J, Reinhardt R L, Ehst B D, Ingulli E, Rudensky A Y, Jenkins M K (2003) Distinct dendritic cell populations sequentially present antigen to CD4 T cells and stimulate different aspects of cell-mediated immunity. Immunity 19: 47-57

Joffre O P, Sancho D, Zelenay S, Keller A M, Reis e Sousa C (2010) Efficient and versatile manipulation of the peripheral CD4+ T-cell compartment by antigen targeting to DNGR-1/CLEC9A. Eur J Immunol 40: 1255-1265

Jongbloed S L, Kassianos A J, McDonald K J, Clark G J, Ju X, Angel C E, Chen C J, Dunbar P R, Wadley R B, Jeet V et al (2010) Human CD141+ (BDCA-3)+ dendritic cells (DCs) represent a unique myeloid DC subset that cross-presents necrotic cell antigens. J Exp Med 207: 1247-1260

Kastenmuller W, Kastenmuller K, Kurts C, Seder R A (2014) Dendritic cell-targeted vaccines—hope or hype? Nat Rev Immunol 14: 705-711

Kissenpfennig A, Henri S, Dubois B, Laplace-Builhe C, Perrin P, Romani N, Tripp C H, Douillard P, Leserman L, Kaiserlian D et al (2005) Dynamics and function of Langerhans cells in vivo dermal dendritic cells colonize lymph node areas distinct from slower migrating Langerhans cells. Immunity 22: 643-654

Klarquist J, Hennies C M, Lehn M A, Reboulet R A, Feau S, Janssen E M (2014) STING-Mediated DNA Sensing Promotes Antitumor and Autoimmune Responses to Dying Cells. J Immunol 193: 6124-6134

Kreutz M, Tacken P J, Figdor C G (2013) Targeting dendritic cells—why bother? Blood 121: 2836-2844

Li J, Ahmet F, Sullivan L C, Brooks A, Kent S, De Rose R, Salazar A M, Reis E S C, Shortman K, Lahoud M H et al (2014) Antibodies targeting Clec9A promote strong humoral immunity without adjuvant in mice and non-human primates. Eur J Immunol Malissen B, Tamoutounour S, Henri S (2014) The origins and functions of dendritic cells and macrophages in the skin. Nat Rev Immunol 14: 417-428

Sancho D, Mourao-Sa D, Joffre O P, Schulz O, Rogers N C, Pennington D J, Carlyle J R, Reis e Sousa C (2008) Tumor therapy in mice via antigen targeting to a novel, DC-restricted C-type lectin. J Clin Invest 118: 2098-2110

Scheiblhofer S, Thalhamer J, Weiss R (2013) Laser microporation of the skin: prospects for painless application of protective and therapeutic vaccines. Expert Opin. Drug Deliv. (2013) 10(6):761-773

Schlitzer A, McGovern N, Teo P, Zelante T, Atarashi K, Low D, Ho A W, See P, Shin A, Wasan P S et al (2013) IRF4 transcription factor-dependent CD11b+ dendritic cells in human and mouse control mucosal IL-17 cytokine responses. Immunity 38: 970-983

Shklovskaya E, Roediger B, Fazekas de St Groth B (2008) Epidermal and dermal dendritic cells display differential activation and migratory behavior while sharing the ability to stimulate CD4+ T cell proliferation in vivo. J Immunol 181: 418-430

Sullivan S P, Koutsonanos D G, Del Pilar Martin M, Lee J W, Zarnitsyn V, Choi S O, Murthy N, Compans R W, Skountzou I, Prausnitz M R (2010) Dissolving polymer microneedle patches for influenza vaccination. Nat Med 16: 915-920

Tamoutounour S, Guilliams M, Montanana Sanchis F, Liu H, Terhorst D, Malosse C, Pollet E, Ardouin L, Luche H, Sanchez C et al (2013) Origins and functional specialization of macrophages and of conventional and monocyte-derived dendritic cells in mouse skin. Immunity 39: 925-938

Weiss R, Hessenberger M, Kitzmuller S, Bach D, Weinberger E E, Krautgartner W D, Hauser-Kronberger C, Malissen B, Boehler C, Kalia Y N et al (2012) Transcutaneous vaccination via laser microporation. J Control Release 162: 391-399

Woo S R, Fuertes M B, Corrales L, Spranger S, Furdyna M J, Leung M Y, Duggan R, Wang Y, Barber G N, Fitzgerald K A et al (2014) STING-Dependent Cytosolic DNA Sensing Mediates Innate Immune Recognition of Immunogenic Tumors. Immunity 41: 830-842

Zhang J G, Czabotar P E, Policheni A N, Caminschi I, Wan S S, Kitsoulis S, Tullett K M, Robin A Y, Brammananth R, van Delft M F et al (2012) The dendritic cell receptor Clec9A binds damaged cells via exposed actin filaments. Immunity 36: 646-657

Example 2

Targeting of Skin Resident Dendritic Cells Via Laser Microporation

Experimental Methods

Major birch pollen allergen Bet v 1 was chemically coupled to polysaccharide mannan from *S. cerevisiae*, or encapsulated in PLGA nanoparticles Mice were immunized with Bet v 1-mannan neoglycoconjugates or Bet v 1-PLGA nanoparticles using the P.L.E.A.S.E.® professional skin laser microporation system or intradermal injections. Antigen uptake at the site of application and in secondary lymphoid organs was studied by fluorescence microscopy and flow cytometry. Antibody titers were measured by ELISA. Cytokine profiles were determined using Multiplex™ MAP Mouse Cytokine/Chemokine assay (Millipore).

Results and Discussion

Bet v 1 protein coupled to mannan polysaccharide was taken up more efficiently by APCs than unconjugated protein. This uptake was inhibited in presence of an excess of mannose, suggesting a receptor mediated endocytocis. In contrast to soluble Bet v 1, mice immunized with Bet v 1-mannan showed higher antibody titers and strong Th1/Th17 cytokine production. Transcutaneous immunization with Bet v 1-mannan conjugates elicited a more potent immune response than intradermal immunization. Interestingly, Bet v 1 encapsulated in PLGA nanoparticles showed the opposite. These nanoparticles were immunogenic when administered intradermally, but no antibody response was detected after transcutaneous immunization (FIG. 6).

Using fluorescently labeled Bet v 1-mannan we were able to demonstrate a massive monocytic infiltrate at the application site (FIG. 7). In contrast, the PLGA encapsulated antigen was poorly internalized into the skin and no cellular infiltrate was detected.

We also analyzed the antigen distribution in the skin draining lymph nodes and Bet v 1-mannan was found primarily in medullary macrophages and CD11b+ dendritic cells. These two cell types are known to express high levels of mannose receptor which has a high affinity for polymannose structures.

Based on the results obtained with Bet v 1-mannan nanoparticles, targeting capacity of different polysaccharide-protein conjugates is feasible.

Due to the immune polarizing properties of the CLRs, this approach can be used to generate tailored immune responses in a very effective and patient friendly way.

Conclusion

Carbohydrate coupling can be used for efficient delivery of antigens to APCs via C-type lectin receptors. The P.L.E.A.S.E.® Professional laser poration system allows for efficient delivery of protein neoglycoconjugates and induction of potent immune responses.

REFERENCES

1. Weiss R, Scheiblhofer S, Machado Y, Thalhamer J. Curr Opin Allergy Clin Immunol. 2013, 13(6):669-76.
2. Pasparakis M, Haase I, Nestle F O. Nat Rev Immunol. 2014; 14(5):289-301
3. Weinberger E E, Himly M, Myschik J, Hauser M, Altmann F, Isakovic A, Scheiblhofer S, Thalhamer J, Weiss R. J Control Release. 2013; 165(2).

Example 3

Immunization of C57BL/6 Mice with Peptide Cancer Vaccine for Liver Cancer

C57BL/6 mice were immunized with a multi-peptide cancer vaccine comprising HCV epitopes derived from NS3 and Core viral proteins and universal tumor antigen mTERT epitopes either subcutaneously or by laser-assisted epidermal immunogen delivery. In particular, the peptide cancer vaccine comprised the HCV NS3 peptide: LLYRLGAVQ-NEVTLTHPITK (amino acids 598 to 617 of the HCV NS protein, SEQ ID NO. 1), the HCV Core peptide: GGAARALAHGVRVLEDGVNY (amino acids 145-164 of the HCV Core protein, SEQ ID No. 2) and the mTERT peptide: PTRPVGRNFTNLRFLQQIKS (amino acids 194-

213 of mTERT, SEQ ID NO. 3) (Tagliamonte M. et al., 2015). The peptide cocktail contained 20 µg per each peptide, emulsified with a combination of 50 µg CpG and montanide. The peptide cancer vaccine was either administered alone or in combination with metronomic chemotherapy comprising 240 µg cyclophosphamide (CTX), 100 µg paclitaxel (PTX), and 20 µg docetaxel (DTX). Administration of PBS and adjuvant (Montanide) were used as controls. Immunization groups and protocols are shown in FIG. 13 and were as follows: (PBS) administration of PBS alone; (Adju) administration of adjuvant alone; (Chemo) daily subcutaneous administration of chemotherapy; (Pept sc.) weekly subcutaneous administration of peptide cancer vaccine; (Pept sc+Chemo) weekly subcutaneousadministration of peptide cancer vaccine in combination with daily chemotherapy; (Pept Las) weekly laser-assisted topical administration of peptide vaccine; (Pept Las+Chemo) weekly laser-assisted topical administration of peptide vaccine in combination with chemotherapy.

For laser-assisted epidermal immunogen delivery a P.L.E.A.S.E. portable laser developed by Pantec Biosolutions AG (Bach et al., 2012, Allergy 67: 1365-1374) was used with the following setting: fluence: 11.9 J/cm$^2$, pulse duration: 75 µs; RepRate: 200 Hz; pulses per pore: 2, pore array size: 14 mm$^2$ and pore density 8%. P.L.E.A.S.E.-assisted skin microporation was performed on the ear of anesthetized mice. Sterile control or peptide vaccine solutions were then evenly applied on the microporated ear surface. The solution percolated inside the micropores in less than 10 minutes.

CD4+ and CD8+ T cells in peripheral blood mononuclear cells (PBMCs) were analyzed in the different immunization groups at three time points (FIG. 14). Standard protocols were used to determine CD4+ and CD8+ cells, such as flow cytometry using PE-anti-mouse CD4 or PE/Cy7-conjugated anti-mouse CD8 antibodies. The percentage of CD4+ T cells in PBMCs varied among experimental groups and, in each group, during the immunization protocol. The percentage values of CD4+ T cells never dropped below 40%, and all groups showed an increase in the percentage at second bleeding and a more or less pronounced reduction at third and last bleeding (FIG. 14A).

Similar to CD4+ T cells, but with a mirroring pattern, the percentage of CD8+ T cells in PBMCs varied among experimental groups and, in each group, during the immunization protocol. The percentage values of CD8+ T cells never dropped below 20%. At third and last bleeding, all groups showed approximately 40% of CD8+ T cells. Of note, the group treated with peptides administered with laser, in combination with metronomic chemotherapy (PEP-LASER-CHEMO), showed a percentage of CD8+ T cells steadily around 40% during the whole immunization protocol (FIG. 14B).

According to the pattern of CD4+ and CD8+ T cells during the immunization protocol, the CD4:CD8 ratio in PBMCs varied among experimental groups and, in each group, during the immunization protocol (FIG. 15A). At the third and last bleeding, all groups showed a ratio of approximately 1. Of note, the group treated with peptides administered with laser, in combination with metronomic chemotherapy (PEP-LASER-CHEMO), showed a CD4:CD8 ratio in PBMCs of approximately 1 during the whole immunization protocol. This implies a more balanced ratio between the two effector T cell populations (FIG. 15A).

The percentage of CD4+ and CD8+ T cells in spleens and the respective ratio of CD4+:CD8+ cells was analyzed at the end of the immunization protocol using methods known in the art. The percentages of CD4+ and CD8+ T cells did not significantly vary among experimental groups (FIG. 3B). Percentage of CD8+ T cells is increased in all groups treated with metronomic chemotherapy and, accordingly, the CD4:CD8 ratio drops to approx. 1 (FIG. 15B).

Example 4

Ex-Vivo Re-Stimulation of Splenocytes from Immunized Mice with Vaccine Epitopes

Splenocytes obtained from the different experimental groups of mice immunized as described in Example 3 (i.e., PBS, Adj, Chemo, Pept, Pept+Chemo, Pept laser and Pept laser+Chemo) were re-stimulated ex-vivo for 6 hours with either HCV core, HCV NS3, mTERT peptide or a pool of these peptides. The secretion of IFN gamma was evaluated in both CD8+ and CD4+ T cell populations by intracellular staining using methods known in the art. For example, $1 \times 10^6$ splenocytes, after red blood cell lysis, were resuspended in RPMI medium and stimulated at 37 C in the presence of 1 µL/mL Golgi Plug, with 20 µg of each peptide or PBS as a negative control. Cells were then incubated with PE/Cy7-conjugated anti-mouse CD8. After washing and permeabilization, cells were incubated with APC-conjugated anti-mouse interferon gamma and analyzed by flow cytometry.

Intra-dermal laser-assisted administration provided a significant enhancement in immunogenicity of peptides, which is further boosted when combined with metronomic chemotherapy (FIG. 16).

Epitope-specific T lymphocyte responses to vaccine peptides, i.e. TERT, HCV Core, HCV NS3 or a pool of these epitopes, were evaluated in IFN-gamma positive CD8+ T cells and IFN-gamma CD4+ cells obtained from mice immunized as described in Example 1 (i.e., subcutaneously with the peptide vaccine alone (Pept) or in combination with chemotherapy (Pept+Chemo) and mice immunized with peptide vaccine administered by laser-assisted epidermal immunogen delivery alone (Pept laser) or in combination with chemotherapy (Pept laser+Chemo). Splenocytes from these different experimental groups were re-stimulated as described above.

Intra-dermal laser-assisted administration provided a significant enhancement over the sub-cutaneous administration in breadth and magnitude of epitope-specific T lymphocyte responses to vaccine epitopes. Metronomic chemotherapy significantly enhanced such effect (FIG. 17). Number of IFNg+DC8+ cells are shown on y axis, after re-stimulation of splenocytes Furthermore, IFNγ production, CD8, CD4 and CD25 were determined in the CD8+ T cells population of each experimental immunization group as described above (i.e., Pept, Pept chemo, Pept laser, Pept laser chemo) upon restimulation with vaccine epitopes. IFNγ production was directly correlated with CD8+ T cells and inversely correlated with CD4+ T cells. Surprisingly, a striking direct correlation was observed also with CD4+CD25+ Treg cells (FIG. 18).

The invention claimed is:
1. A method of treating a subject in need of therapeutic treatment comprising administering to the subject a pharmaceutical preparation comprising:
  an antigen linked to a binder of a dermal migratory antigen-presenting cell (APC), which is a ligand specifically recognizing an APC expressing chemokine (C motif) receptor 1 (XCR1) and/or C—C chemokine receptor type 7 (CCR7) or an APC expressing a C-type lectin receptor or a TLR ligand; and an active substance for the therapeutic treatment of subject;

wherein the pharmaceutical preparation is administered via intradermal administration through laser-generated micropores generated by an ablative laser having a wavelength of at least 2500 nm to 10600 nm to a target location;

wherein the subject is suffering from an infectious disease, cancer, or an immune disorder selected from the group consisting of an autoimmune disease and an allergy.

2. The method according to claim 1, wherein the immune modulator is selected from the group consisting of an adjuvant, antigen, an antibody, an antigen-binding fragment thereof, a small molecule, a peptide, a protein, and combinations of any of the foregoing.

3. The method according to claim 1, wherein the immune modulator downregulates the coinhibitory receptor cytotoxic T-lymphocyte-associated protein 4 (CTLA-4), the coinhibitory receptor, programmed death 1 (PD-1), or its ligand, programmed death ligand 1 (PD-L1).

4. The method according to claim 1, wherein the immune modulator is an antibody or antigen-binding fragment thereof, for use in passive immunotherapy.

5. The method according to claim 1, wherein the antigen is selected from the group consisting of a tumor antigen, a self-antigen, a microbial antigen, an allergen, and an antigen comprising an immunorelevant epitope of any of the foregoing.

6. The method according to claim 5, wherein the antigen is administered in an effective amount to elicit local T-cell response at a draining lymph node, and optionally systemic T-cell response.

7. The method according to claim 1, wherein the preparation is repeatedly administered within a priming area.

8. The method according to claim 7, wherein the priming area is in close proximity to the target location.

9. The method according to claim 1, wherein the method comprises:
a) producing a microporated surface comprising a plurality of micropores a predetermined permeation surface of the subject's skin by laser poration; and
b) applying the pharmaceutical preparation topically onto the microporated surface.

10. The method according to claim 9, wherein the microporated surface is about two to ten times smaller than a total inner surface of pores created by the laser poration.

11. The method according to claim 9, wherein the pharmaceutical preparation is applied in the form of an antigen-rich solution or emulsion or dispersion.

12. A method of enhancing an immune response in a subject in need thereof, comprising:
Administering to a subject a pharmaceutical preparation comprising:
an antigen linked to a binder of a dermal migratory antigen-presenting cell (APC), which is a ligand specifically recognizing an APC expressing chemokine (C motif) receptor 1 (XCR1) and C—C chemokine receptor type 7 (CCR7) or an APC expressing a C-type lectin receptor or a TLR ligand; and
an active immune modulator;
wherein the pharmaceutical preparation is administered via intradermal administration through laser-generated micropores generated by an ablative laser having a wavelength of at least 2500 nm to 10600 nm to a target location.

13. A method of inducing activation of $CD8^+$ and $CD4^+$ T cells in a subject in need thereof comprising administering to a subject a pharmaceutical preparation comprising:
an antigen linked to a binder of a dermal migratory antigen-presenting cell (APC), which is a ligand specifically recognizing an APC expressing chemokine (C motif) receptor 1 (XCR1) and C—C chemokine receptor type 7 (CCR7) or an APC expressing a C-type lectin receptor or a TLR ligand; and
an active substance which is an immune modulator for said subject;
wherein the pharmaceutical preparation is administered via intradermal administration through laser-generated micropores generated by an ablative laser having a wavelength of at least 2500 nm to 10600 nm to a target location;
wherein the subject suffers from reduced T cell activation or immune-suppression.

* * * * *